US009017277B2

(12) United States Patent
Lyu et al.

(10) Patent No.: US 9,017,277 B2
(45) Date of Patent: Apr. 28, 2015

(54) SYSTEM AND IMPLANTABLE DEVICE FOR TREATING CHRONIC KIDNEY DISEASE

(75) Inventors: SuPing Lyu, Maple Grove, MN (US); Thomas Edward Meyer, Stillwater, MN (US); Mark Fredrick Daniels, Lino Lakes, MN (US); Bryant J. Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/462,190

(22) Filed: May 2, 2012

(65) Prior Publication Data

US 2012/0289881 A1    Nov. 15, 2012

Related U.S. Application Data

(60) Provisional application No. 61/481,678, filed on May 2, 2011.

(51) Int. Cl.
*A61M 1/14* (2006.01)
*A61M 1/16* (2006.01)
*B01D 63/08* (2006.01)
*B01D 61/28* (2006.01)
*B01D 61/18* (2006.01)

(52) U.S. Cl.
CPC ........ *A61M 1/1678* (2013.01); *B01D 2313/105* (2013.01); *B01D 63/084* (2013.01); *B01D 61/28* (2013.01); *B01D 61/18* (2013.01)

(58) Field of Classification Search
USPC .................. 604/9; 210/645, 646, 321.89, 343
See application file for complete search history.

(56) References Cited

U.S. PATENT DOCUMENTS

| | | | |
|---|---|---|---|
| 3,370,710 A | 2/1968 | Bluemle, Jr. | |
| 3,669,878 A | 6/1972 | Marantz | |
| 3,669,880 A | 6/1972 | Marantz | |
| 3,809,241 A | 5/1974 | Alvine | |
| 3,850,835 A | 11/1974 | Marantz | |
| 3,989,622 A | 11/1976 | Marantz | |
| 4,323,455 A * | 4/1982 | Tanaka et al. | ............ 210/321.75 |
| 4,460,555 A | 7/1984 | Thompson | |
| 4,581,141 A | 4/1986 | Ash | |

(Continued)

FOREIGN PATENT DOCUMENTS

| | | |
|---|---|---|
| EP | 0022370 A1 | 1/1981 |
| WO | 2006023589 A2 | 3/2006 |

(Continued)

OTHER PUBLICATIONS

PCT/US2012/025711 International Search Report mailed Jul. 4, 2012.

(Continued)

*Primary Examiner* — Leslie Deak
*Assistant Examiner* — Sara Sass
(74) *Attorney, Agent, or Firm* — Hahn & Voight PLLC; Roger C. Hahn

(57) ABSTRACT

An implantable dialysis device with a related medical system for intracorporeal dialysis and ultrafiltration of blood, and methods of use are described. The medical system includes an extracorporeal module, a cutaneous module, and an implantable module. Features of the implantable module facilitate delivery and flow of blood and dialysate through the medical system. A filter pack within the implantable module performs dialysis and ultrafiltration of blood. System cleansing is also described.

36 Claims, 49 Drawing Sheets

(56) References Cited

U.S. PATENT DOCUMENTS

| | | | |
|---|---|---|---|
| 4,650,587 A | 3/1987 | Polak | |
| 4,769,037 A * | 9/1988 | Midcalf | 623/23.65 |
| 4,826,663 A | 5/1989 | Alberti | |
| 6,627,164 B1 | 9/2003 | Wong | |
| 6,818,196 B2 | 11/2004 | Wong | |
| 6,878,283 B2 | 4/2005 | Thompson | |
| 7,023,359 B2 | 4/2006 | Goetz et al. | |
| 7,566,432 B2 | 7/2009 | Wong | |
| 7,736,507 B2 | 6/2010 | Wong | |
| 7,776,210 B2 | 8/2010 | Rosenbaum | |
| 2002/0112609 A1 | 8/2002 | Wong | |
| 2003/0143352 A1* | 7/2003 | Yang et al. | 428/36.9 |
| 2003/0155312 A1* | 8/2003 | Ivansons et al. | 210/787 |
| 2004/0143173 A1 | 7/2004 | Reghabi et al. | |
| 2006/0076295 A1 | 4/2006 | Leonard | |
| 2008/0006570 A1 | 1/2008 | Gura et al. | |
| 2009/0127193 A1 | 5/2009 | Updyke | |
| 2009/0131858 A1 | 5/2009 | Fissell | |
| 2009/0173682 A1* | 7/2009 | Robinson et al. | 210/232 |
| 2009/0198170 A1* | 8/2009 | Childers et al. | 604/6.09 |
| 2009/0282980 A1 | 11/2009 | Gura | |
| 2010/0022936 A1 | 1/2010 | Gura | |
| 2010/0078381 A1 | 4/2010 | Merchant | |
| 2010/0078387 A1 | 4/2010 | Wong | |
| 2010/0084330 A1 | 4/2010 | Wong | |
| 2010/0116740 A1* | 5/2010 | Fulkerson et al. | 210/646 |
| 2010/0326911 A1 | 12/2010 | Rosenbaum | |
| 2011/0017665 A1 | 1/2011 | Updyke | |

FOREIGN PATENT DOCUMENTS

| | | |
|---|---|---|
| WO | 2009157877 A1 | 12/2009 |
| WO | 2010052705 A1 | 5/2010 |

OTHER PUBLICATIONS

Roberts M, The regenerative dialysis (REDY) sorbent system, Nephrology, 1998, 275-278 : 4.

Marchant; et. al., In vivo Biocompatibility Studies I: The Cage implant System and a Biodegradable Hydrogel, J. Biomed. Mat. Res., 1983. 301-325 : 17.

Siegenthalar, et. al., Pulmonary fluid status monitoring with intrathoracic impedance, Journal of Clinical Monitoring and Computing, 2010, 449-451 : 24.

Wang, Fundamentals of intrathoracic impedance monitoring in heart failure, Am. J. Cardiology, 2007, 3G-10G : Suppl.

Bleyer, et. al., Sudden and cardiac death rated in hemodialysis patients, Kidney International, 1999, 1553-1559 : 55.

* cited by examiner

SYSTEM AND IMPLANTABLE DEVICE FOR TREATING CHRONIC KIDNEY DISEASE

FIELD OF THE INVENTION

The invention relates to an implantable medical device providing ultrafiltration and hemodialysis for the treatment of pathological conditions such as chronic kidney disease. The systems and methods of the invention include an implantable dialyzer and medical systems having percutaneous or subcutaneous ports, external control components and fluid reservoirs. Related methods of slow continuous blood flow in a medical device, and performing hemodialysis and/or ultrafiltration in the implantable dialyzer are also provided. The invention further relates to the treatment of chronic kidney disease including methods of introducing a dialysate directly into a patient and dialyzing blood intracorporeally.

BACKGROUND

Chronic kidney disease (CKD), also known as chronic renal disease, is a progressive loss in renal function over a period of months, or years. The most severe stage of CKD is End Stage Renal Disease (ESRD), which occurs when the glomerular filtration rate (GFR) is lower than 15 mL/min. In the U.S., the two main causes of CKD are diabetes and high blood pressure, which are responsible for up to two-thirds of the cases. Heart disease is the leading cause of death for all people having CKD. Excessive fluid can accumulate in patients suffering from ESRD. The mortality rate of ESRD patients who receive traditional hemodialysis therapy is 24% per year with an even higher mortality rate among diabetic patients. Fluid accumulates in ESRD patients because the kidneys can no longer effectively remove water and other compounds from the body. The fluid accumulates first in the blood and then accumulates throughout the body resulting in swelling of the extremities and other tissues as edema. This accumulation of fluid causes increased stress on the heart causing significant increases in blood pressure or hypertension, which can lead to heart failure. Hypertension is the single most important predictor of coronary artery and cerebrovascular diseases and is the most predominant comorbidity among patients with ESRD, with a prevalence of approximately 80%. Accordingly, an objective of ESRD treatment is to render patients euvolemic and normotensive effectively. Medicare recognizes the severity of this problem by mandating that each ESRD patient's treatment plan "render the patient euvolemic and normotensive"—specifically, blood pressure (BP) should be "reduced to ≤130/80 with minimal use of medications." Chronic fluid overload and inability to maintain dry weight plays a major role in the generation and prevalence of hypertension among ESRD patients. The ability to provide daily ultrafiltration (UF), and maintain dry weight would contribute to the control of hypertension by decreasing the need for UF during hemodialysis sessions, and could theoretically decrease, the number of hemodialysis (HD) treatments per week. The reduction in hemodialysis treatment time would address some of the pressing medical and economic issues surrounding the treatment of ESRD patients.

Although the population of patients afflicted with CKD grows each year, there is no cure. Current treatments for CKD seek to manage comorbidities and, if possible, slow the progression of the disease. However, as the disease progresses, renal function decreases and eventually renal replacement therapy is employed to compensate for lost kidney function. Renal replacement therapy entails transplantation of a new kidney, or, dialysis. The excess fluid accumulated in patients suffering from CKD is generally removed by direct ultrafiltration or by the ultrafiltration action of a dialysis procedure. These procedures are carried out three times a week in three to five hour, sessions. Dialysis emulates kidney function by removing waste solutes and excess fluid from a patient's blood. During dialysis, the patient's blood that contains high concentration of waste solutes is exposed to a semi-permeable membrane in contact with a solute-deficient dialysate. Solute removal is accomplished via diffusion across the membrane, while fluid removal is accomplished via pressure-driven ultrafiltration. Once the blood is purified, it is then returned to the patient. Although effective at removing wastes from blood, dialyses treatments are administered intermittently and therefore do not emulate the continuous function of a natural kidney. Moreover, there are many inconveniences associated with dialysis, such as the necessity of committing to time consuming, thrice weekly treatments. Many patients eventually elect to forgo treatment on this basis alone. Additionally, several complications are associated with dialysis, resulting from the sporadic nature of conventional treatment regimens. These complications include blood pressure and electrolyte concentration fluctuation, vascular abnormalities, anemia, nausea, and fatigue. In severe cases, removal of the large amounts of fluid may even lead to arrhythmias and heart failure. Once the dialysis session is completed, the fluid begins to accumulate again in the tissues of the patient.

The benefits of dialysis notwithstanding, statistics indicate that three out of five dialysis patients die within five years of commencing treatment. Increasing the frequency and duration of dialysis sessions more closely resembles the continuous kidney function sought to be emulated. In addition, there are several advantages to treating patients suffering from fluid overload with ultrafiltration rather than diuretic drugs. Ultrafiltration offers an efficient fluid removal process without the side effects observed with use of pharmaceuticals, such as kidney failure and drops in blood pressure. Ultrafiltration and/or hemofiltration expose blood to a semi-permeable membrane under transmembrane pressure. The membrane's properties provide that water, salts, and other particles of small molecular weight pass through the membrane, while blood cells, proteins, and other molecules of larger molecular weight do not. An ultrafiltration cartridge is generally made up of a large number of small diameter hollow fiber type membranes. Typically, blood is accessed from the patient via a pair of needles placed in a fistula or a graft, or a catheter placed in an artery or large vein and is pumped into the ultrafiltration cartridge to generate the pressure to carry out the ultrafiltration process. The blood goes through the inner lumens of the hollow fibers, and the filtrate goes to the inter-fiber space and is removed. The treated blood is then returned to the patient.

These conventional ultrafiltration procedures have several disadvantages. As with dialysis, which may be performed at the same time for renal disease patients, a patient's mobility is limited because the processes are carried out extracorporeally using large, fixed machines. The most common complications in performing extracorporeal fluid removal are cardiovascular instability, hypotension, and shock. These events seem to be correlated with ultrafiltration rate. When the rate of ultrafiltration exceeds 0.25 mL/min/kg, the chance of hypotensive episodes increases exponentially. The cause of these complications is the discrepancy between the speed of fluid extraction by the ultrafiltration device and the rate of intravascular refilling from the interstitial and intracellular space within the patient. Long-term blood access necessary for the operation of ultrafiltration and hemodialysis devices can also be problematic. Vascular access devices such as percutaneous catheters used in hemodialysis patients may cause complications such as bleeding, infection, and clotting. Interactions between blood components and the materials found within blood processing systems could induce the activation of several biological systems such as platelets, complement, and coagulation cascades. Accordingly, conventional blood processing systems typically employ the use of anticoagulant drugs, such as heparin, to prevent the formation of blood clots. Prolonged use of anticoagulant drugs presents a significant risk of uncontrolled bleeding in patients.

In continuous hemofiltration or hemodialysis, blood is filtered and dialyzed without interruption. These procedures enable the removal of large volumes of fluid while avoiding the hypotensive episodes caused by intermittent hemodialysis, and are indicated for managing patients with acute renal failure who are hemodynamically unstable, require large volumes of fluid, or both. In continuous hemofiltration, water and solutes up to a certain molecular weight filter from the blood by convection through a permeable membrane, the filtrate is discarded, and the patient must receive infusions of physiologically balanced water and electrolytes. A dialysis circuit can be added to the filter to improve solute clearance. These procedures may be arteriovenous or venovenous. Arteriovenous procedures thus have the benefit of being a simple system in which arterial pressure is sufficient to push blood through the filter into the femoral vein without using a pump. However, filtration rates are typically low for continuous arteriovenous procedures, especially in hypotensive patients. In continuous venovenous procedures, a pump is employed to push blood from one large vein through the dialysis circuit and back into the venous circulation. Using a double-lumen catheter, blood is drawn from and returned to the same vein.

Some examples of prior art devices for dialyzing blood teaching use of various membranes, inlets and outlets are listed below.

U.S. Pat. No. 3,370,710 teaches a blood dialyzing apparatus with a pleated membrane and having a first fluid inlet and outlet pair, and a second fluid inlet and outlet pair.

U.S. Pat. No. 3,809,241 teaches a portable kidney, coil of a portable dialysate delivery system utilizing a self-contained re-circulating source of dialysate solution or a single-pass dialysate proportioning system. The output of the artificial kidney within the dialysate pumping and delivery system is via a tube and an output tube in which dialysate exits. The output of a blood pump enters the artificial kidney via a tube, and the outlet of the blood circuit system from the artificial kidney is at another tube.

US 2008/0006570 teaches a chambered cartridge for treating medical or biological fluids. The cartridge, which may be rigid or flexible, includes at least one inlet and one outlet and a plurality of separators.

US 2006/0076295 teaches a wrist-wearable dialysis system having a dialyzer and a pump having first, second and third inlet channels, first, second and third exit channels and a microfluidic extraction channel connected to the first, second and third inlet channels and the first, second and third exit channels and a flush port.

US 2010/0022936 teaches a component of a wearable ultrafiltration device having a blood inlet tube leading from a first blood vessel, a blood pump, an anticoagulant reservoir for infusing anticoagulants into the blood, a blood filter including a substrate through which the blood is circulated and filtered, a fluid bag for storing the excess fluid and a blood outlet tube leading to a second blood vessel. Hollow fibers are also taught wherein excess fluid is drained from the hollow fibers, which act as a sieve such that excess fluid passes through, but not blood.

Portable devices for hemodialysis or ultrafiltration in the form of wearable devices are generally large and cumbersome. Hence, there is a need for an implantable device that can provide both hemodialysis and/or ultrafiltration to a patient in a configuration of blood and dialysate flow across a membrane that is suitable for small volumes in a portable or implantable dialyzer. The need extends to providing methods for cleaning wherein the device can be used without decrement for a prolonged period, ideally for the expected life of the device, without the need for heparin, citrate or other anti-coagulants. Such a device would lower the very substantial costs to the healthcare system in treating patients with acute or chronic renal failure or CHF by enabling new modalities of outpatient, home or ambulatory treatment. Patients would benefit from fewer anticoagulant-related complications, less medication, less hospitalization and improved quality of life.

There is also a need for a device that provides continuous hemofiltration or continuous hemodiafiltration that would enhance patient mobility and reduce complications related to vascular access and extracorporeal blood processing. Furthermore, there is a need for an implantable hemodiafiltration device capable of operating at a pressure similar to that of a patient's blood pressure, and at a rate similar to that of natural kidney function to provide more consistent and beneficial therapy as compared to existing intermittent treatment regimens. Additionally, an implantable device used for dialysis or ultrafiltration is needed that would eliminate the need for visiting a dialysis clinic for treatments, and improve patient compliance with dialysis prescriptions. An implantable hemodiafiltration device used for dialysis or ultrafiltration operable at a patient's average blood pressure would thus permit blood, treatment schedules that are suitable and adaptable to a patient's lifestyle, thereby promoting patient health and enhancing patient quality of life.

SUMMARY OF THE INVENTION

The invention is directed to an implantable dialyzer and related medical systems. In one embodiment, the implantable dialyzer has a filter pack for hemodialysis and/or ultrafiltration having two or more membranes forming a membrane stack that has alternating dialysate and blood membrane channels interposed between each membrane; a first manifold assembly connected to a first side of the filter pack containing both a blood and a dialysate manifold, each manifold having a specified cross-sectional geometry, wherein the blood manifold is in fluid communication with the blood membrane channels and the dialysate manifold is in fluid communication with the dialysate membrane channels; a second manifold assembly connected to a second side of the filter pack containing both a blood and a dialysate manifold, each manifold having a specified cross-sectional geometry, wherein the blood manifold is in fluid communication with the blood membrane channels and the dialysate manifold is in fluid communication with the dialysate membrane channels; a blood feed-in and a blood feed-out in fluid communication with the blood membrane channels via the blood manifolds; a dialysate feed-in and a dialysate feed-out in fluid communication with the dialysate membrane channels via the dialysate manifolds; and a housing encasing the filter pack. In certain version, the blood and dialysate manifolds have a cross-sectional geometry selected from a substantially C-shape, U-shape, D-shape, circle, rectangle, triangle or semicircle and can also transition to any of these cross-sectional geometries.

In another embodiment, the implantable dialyzer has a filter pack encased in a housing selectively performing hemodialysis and/or ultrafiltration wherein the filter pack exchanges water, urea, NaCl, electrolytes, and waste substances with a dialysate during hemodialysis and removes water during ultrafiltration, and also has a blood feed-in and a blood feed-out of the housing in fluid communication with the filter pack, and a dialysate feed-in and a dialysate feed-out of the housing in fluid communication with the filter pack. The implantable dialyzer housing can be contoured to ergonomically fit a patient's anatomy.

In one embodiment, the implantable dialyzer has one or more membranes configured inside the filter pack, each membrane having a dialysate side in contact with dialysate and a blood side in contact with blood during hemodialysis. In another embodiment, the implantable dialyzer has a membrane stack having two or more membranes forming a membrane stack that has alternating dialysate and blood membrane channels interposed between each membrane. The implantable dialyzer can also have a blood feed manifold in fluid communication with the blood feed-in, a blood return manifold in fluid communication with the blood feed-out, a dialysate feed manifold in fluid communication with the dialysate feed-in, and a dialysate return manifold in fluid communication with the dialysate feed-out. The perimeter shape of each membrane can be relatively offset and identically contoured to fit the contour of the implantable dialyzer housing. The perimeter shape of each membrane can also be independently contoured to ergonomically fit the contour of the implantable dialyzer housing.

In another embodiment, the implantable dialyzer has a shunt A connecting a dialysate manifold in a second manifold assembly defined as a dialysate feed manifold with the blood manifold in a second manifold assembly defined as a blood return manifold and a shunt B connecting the blood manifold in a first manifold assembly defined as a blood feed manifold with the dialysate manifold in the first manifold assembly defined as a dialysate return manifold, a valve V2 disposed on the blood feed manifold, a valve V4 disposed on the blood return manifold, a valve V1 disposed on the dialysate return manifold, a valve V3 disposed on the dialysate feed manifold, an external valve Ve1 disposed on the dialysate feed-in, an external valve Ve2 disposed on the dialysate feed-out, a valve V5 disposed on the shunt A, and a valve V6 disposed on the shunt B. The implantable dialyzer can also have suturing holes disposed on the housing to surgically affix the dialyzer adjacent to suitable vasculature.

Other embodiments of the invention include a method for performing hemodialysis in an implantable dialyzer having the steps of turning on valve V2, turning on valve V4, turning on valve Ve1, and turning on valve Ve2.

Another embodiment contemplates a method for performing ultrafiltration in an implantable dialyzer having the steps of turning on valve V2, turning on valve V4, turning off valve Ve1, and turning on valve Ve2.

In one embodiment, a method for performing blood path soaking in an implantable dialyzer is provided having the steps of turning on valve V2, turning off valve V4, turning off valve Ve1, and turning off valve Ve2.

In yet another embodiment, a method for controlling dialysate path flushing in an implantable dialyzer is provided having the steps of turning off valve V2, turning off valve V4, turning on valve Ve1, and turning on valve Ve2.

In still another embodiment, a method for controlling blood path leaking in an implantable dialyzer is provided having the steps, of turning off valve V2; turning off valve V4, turning on valve Ve1, and turning on valve Ve2.

In an embodiment of the invention, a method for controlling contamination in an implantable dialyzer is provided having the steps of turning off valve V2, turning off valve V4, turning off valve Ve1, and turning off valve Ve2

In another embodiment, a medical system is provided having an implantable dialyzer having a filter pack encased in a housing selectively performing hemodialysis and/or ultrafiltration wherein the filter pack exchanges water, urea, NaCl, electrolytes, and waste substances with a dialysate during hemodialysis and the filter pack removes water during ultrafiltration, a blood feed-in and a blood feed-out of the housing in fluid communication with the filter pack, and a dialysate feed-in and a dialysate feed-out of the housing in fluid communication with the filter pack; percutaneous or subcutaneous ports and conduits, and a detachable external module connected to the implantable dialyzer via the percutaneous or subcutaneous ports and conduits.

In one embodiment, a method is provided for introducing a dialysate into a patient in need thereof, and dialyzing blood intra-corporeally. The method can have the additional steps of feeding blood into an implantable dialyzer from an artery, dialyzing the blood across a membrane using the dialysate, collecting effluent dialysate, and feeding the dialyzed blood out of the dialyzer into a vein. The method can also be performed across the membrane using a pressure differential between an arterial and a venous side. The method can optionally use a pump to provide the necessary transmembrane pressures.

In yet another embodiment, a method for continuous blood flow in a medical device is provided, having the steps of directing blood into one or more blood feed channels, a portion of the blood being directed into one or more blood membrane channels, receiving blood from the one or more blood membrane channels in a blood return channel, directing dialysate into one or more dialysate feed channels, a portion of the dialysate being directed into one or more dialysate membrane channels, and receiving dialysate from the one or more dialysate membrane channels in a dialysate return channel.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 13(*a*) is a circuit diagram for co-current flow. FIG. 13(*b*) is a circuit diagram for counter-current flow.

FIG. 14(*a*) is a counter-current configuration with tapered feed and return manifolds. FIG. 14(*b*) is a co-current configuration with tapered feed and return manifolds. FIG. 14(*c*) is a counter-current configuration with straight feed and return manifolds. FIG. 14(*d*) is a co-current configuration with straight feed and return manifolds. FIG. 14(*e*) is a co-current configuration with variable feed and return manifolds.

FIG. 21(*a*) is a top view of the implantable module embodiment. FIG. 21(*b*) is a bottom view of the implantable module embodiment.

FIG. 22(*a*) is a side view of the implantable module embodiment. FIG. 22(*b*) is a top view of the implantable module embodiment.

FIG. 25(*a*) is a sectional perspective view showing a blood membrane channel of the implantable module embodiment. FIG. 25(*b*) is a sectional perspective view showing a dialysate membrane channel of the implantable module embodiment.

FIG. 27(*a*) is a top view of a blood membrane channel of the implantable module embodiment. FIG. 27(*b*) is a top view of a dialysate membrane channel of the implantable module embodiment.

FIG. 33(*a*) is a top view of the implantable module embodiment. FIG. 33(*b*) is a bottom view of the implantable module embodiment.

FIG. 34(*a*) is a perspective view of the top of the implantable module embodiment with attached inlets. FIG. 34(*b*) is a perspective view of the top of the implantable module embodiment without inlets.

FIG. 35(*a*) is a perspective view of the bottom of the implantable module embodiment with attached outlets as viewed from within module. FIG. 35(*b*) is a perspective view of the outlets of the implantable module embodiment from the perspective of the module.

FIG. 36(*a*) is a perspective view of a dialysate membrane channel of the implantable module embodiment. FIG. 36(*b*) is a perspective view of a blood membrane channel of the implantable module embodiment.

FIG. 37(*a*) is a perspective view of the implantable module embodiment with a casing. FIG. 37(*b*) is a sectional perspective view showing the top of the implantable module embodiment with a casing.

FIG. 38(*a*) is a sectional perspective view showing a blood membrane channel of the implantable module embodiment. FIG. 38(*b*) is a sectional perspective view showing a dialysate membrane channel of the implantable module embodiment.

FIG. 40(*a*) is a sectional perspective view of blood and dialysate channels within a right side of the implantable module embodiment. FIG. 40(*b*) is a sectional perspective view of blood and dialysate manifolds within the right side of the implantable module embodiment.

FIG. 43(a) is a sectional view a front half of the implantable module. FIG. 43(b) is a sectional view of a left side of the implantable module.

FIG. 44(a) is a top view showing a blood side of the membrane filter element. FIG. 44(b) is a bottom view showing a dialysate side of the membrane filter element.

DETAILED DESCRIPTION OF THE INVENTION

Figure 1:
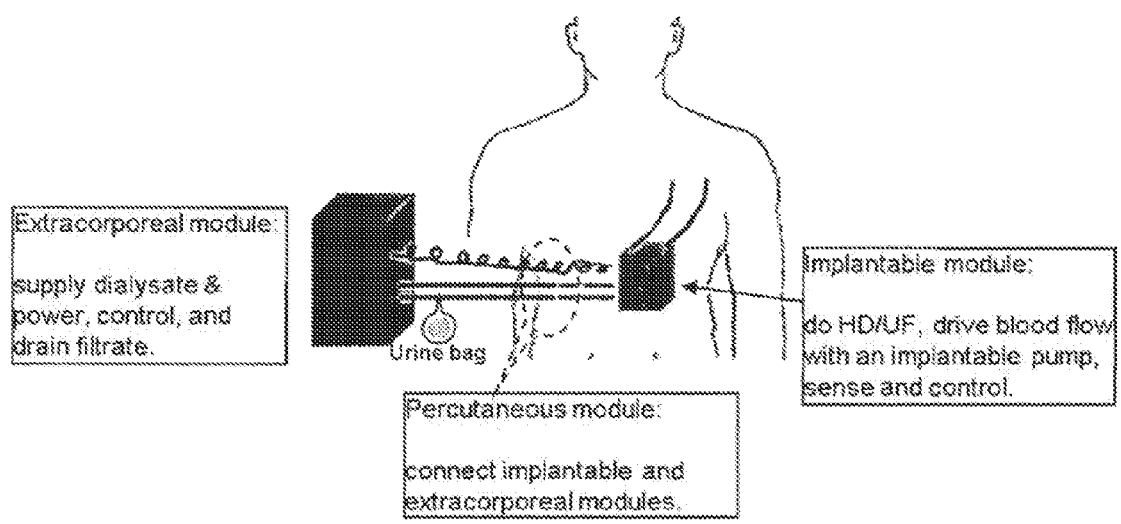
FIG. 1 shows the location and function of each of an extracorporeal module, a cutaneous module, and an implantable module of a hemodialysis system according to the invention.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The terms "administering," "administer," "delivering," "deliver," "introducing," and "introduce" can be used interchangeably to indicate the introduction of a therapeutic or diagnostic agent into the body of a patient in need thereof to treat a disease or condition, and can further mean the introduction of any agent into the body for any purpose.

A "biocompatible material" is a material that has the ability to interface with living biological tissues with an acceptable host response in any of specific medical systems, methods of treatment or delivery contemplated herein. The term does not exclude any response and can include, aggressive or cytotoxic responses. The biocompatible material can consist of synthetic, natural or modified natural polymers intended to contact or interact with the biological systems during application of any of the inventions contained herein.

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail to function.

The terms "communicate" and "communication" include but are not limited to, the connection of system electrical elements, either directly or remotely, for data transmission among and between said elements. The terms also include, but are not limited, to the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase the phrase "consisting of." Thus, the phrase indicates that the limited elements are required or mandatory and that no other elements may be present.

The term "consisting essentially of" includes whatever follows the phrase such as the specified materials or steps, and also materials and steps that do not materially affect basic characteristics.

A "control system" consists of combinations of components that act together to maintain a system to a desired set of performance specifications. The performance specifications can include fluid control components, solutes control components, processors, memory and computer components configured to interoperate.

A "controller" or "control unit" is a device which monitors and affects the operational conditions of a given system. The operational conditions are typically referred to as output variables of the system, which can be affected by adjusting certain input variables.

The term "dialysate" describes a fluid into which solutes from a fluid to be dialyzed diffuse through a membrane.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate may also provide enrichment to the fluid to be dialyzed.

A "membrane" is a material that forms a barrier between two liquids. The membrane is permeable only to certain solutes, and transfers those solutes from one liquid into the other in the presence of a driving force such as a concentration gradient or pressure difference.

The term "filtration" refers to a process of separating solutes from a fluid, by passing the fluid through a filter medium across which certain solutes or suspensions cannot pass. Filtration may be driven by a pressure difference or concentration gradient across a membrane.

"Hemofiltration" is a therapy in which blood is filtered across a semipermeable membrane. Water and solutes are removed from the blood via pressure-driven convection across the membrane. In hemofiltration, solutes small enough to pass through the membrane in proportion to their plasma concentration are removed. The driving force is a pressure gradient rather than a concentration gradient. The rate of solute removal is proportional to the applied pressure that can be adjusted to meet the needs of a clinical situation. In general, the removal of large amounts of plasma water from the patient requires volume substitution. Substitution fluid, typically a buffered solution close to the plasma water composition the patient needs, can be administered pre or post filter (pre-dilution mode, post-dilution mode).

"Hemodialysis" is a technique where blood and a "cleansing fluid" called dialysate are exposed to each other separated by a semipermeable membrane. Solutes within the permeability range of the membrane pass while diffusing along existing concentration gradients. The sieving properties of the membrane exclude all solutes above a certain threshold from crossing the membrane. One common sieving property is "albumin sieving." Albumin is used to measure lymphatic absorption wherein the term "albumin sieve coefficient" can be used to describe a membrane property.

"Hemodiafiltration" is a therapy that combines hemofiltration and hemodialysis.

Osmolarity is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

A "patient" or "subject" is a member of any animal species, preferably a mammalian species, optionally a human. The subject can be an apparently healthy individual, an individual suffering from a disease, or an individual being treated for a disease.

The terms "pressure differential" and "pressure drop" refer to the difference in pressure measurements of a fluid between two points of measurement.

The terms "processor" and "computer processor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture and being capable of carrying out a set of commands, automatically.

The terms "treating" and "treatment" refer to the management and care of a patient having a pathology or condition for which administration of one or more therapeutic compounds is indicated for the purpose of combating or alleviating symptoms and complications of the condition. Treating includes administering one or more formulations of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through, the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving, force, the process is ultrafiltration if the membrane passes small solutes but reject macromolecules.

The term "filter pack," as used herein describes a configuration of filtering membranes.

The term "waste substances," as used herein describes organic and inorganic components that are normally removed by healthy kidneys. The waste substances can be metabolic products such as urea, uric acid, creatinine, chlorides, inorganic sulfate and phosphate, or surplus electrolytes such as over-loaded sodium, potassium, etc. It will be understood the specific "waster substances" can vary between individual depending on diet and environmental factors. Hence, the term is intended to encompass any waste component that is normally removed by a kidney or by dialysis without restriction on the specific type of waste substance.

The term "implantable," as used herein describes a device, component or module intended to complete its function while totally or partially embedded within a patient. Such devices, components, or modules can be introduced surgically or medically into a patient's body, or by medical intervention that remains after the procedure.

The term "manifold" as used in "blood feed manifold," "blood return manifold," "dialysate feed manifold," and "dialysate return manifold," describes both dividing and combining flow configurations where fluid can either enter axially or laterally or both, and can either exit axially or laterally or both.

The term "hydraulic permeability," describes a membrane property characterizing the flow of water through a cross unit of area. Equations describing this property for dialysis can be found in "Replacement of renal function by dialysis edited by Claude Jacobs," $4^{th}$ edition, Kluwer academic publishers, (1996) and are well known in the art.

"Diffusive permeability" is a property of a membrane describing permeation by diffusion. Diffusion is the process of solutes moving from an area of higher concentration to an area of lower concentration The term "porosity," as used herein describes the fraction of open pore volume of a membrane.

The term "bundled hollow fibers," as used herein describes a type of membrane in which hollow fibers are used during dialysis. The hollow fibers are formed after removing glycerin used in hollow, fiber preparation wherein the fibers are covered with spacer yarns, which are filaments designed to create, optimal spacing between the fibers. The collection of fibers serves as a membrane and are assembled or bundled and inserted in the filter of the invention. Other known types of hollow fibers, and methods for their manufacture are contemplated by the invention.

The term "shunt," as used herein describes a passage between channels, such as blood vessels, where the shunt diverts or permits flow from one pathway or region to another.

The term "suturing holes," as used herein is a means for affixing a medical device to tissue where sutures are used to fasten the device.

The term "clamshell," as used herein describes a case or enclosure having two, pieces joined together. For example, the case or enclosure may be joined along a common side by a connection means such as a flexible joint or hinge. Each of the two pieces of the case or enclosure may also be individually shaped to connect together.

The terms "C-shaped," "U-shaped," and "D-shaped" or "D-channel" describe the cross-sectional geometry of a fluid passageway or channel that substantially traces the shape of the alphabetical letter used. For example, a C-shaped cross sectional geometry refers to a channel or passageway that follows the outline of the letter C; a U-shaped channel or passageway has a flattened curvature generally following the outline of the letter U; and a D shaped channel or passageway has a flow path that generally follows the tracing of the letter D. It will be understood the letter descriptions are intended as a guidepost to describe the flow path and are not limited to any particular font or stylization.

The terms "semicircular" or "circular" passageway or channel describe a fluid pathway that has a cross-sectional geometry in the shape being described. It is understood that a substantially circular passageway can include oval, ellipsoidal and other substantially circular shapes. A substantially semicircular passageway includes semicircular oval, semicircular ellipsoid and other generally semicircular shapes.

The terms "tapered inwardly" and "tapered outwardly" as used herein to describe blood feed-out (or flow-out) and feed-in (flow-in) channels and dialysate feed-in and feed-out channels can mean a tapering direction relative to a fluid in-flow or a fluid out-flow. The tapering can be linear or non-linear.

The term "plumbing," as used herein generally describes any system of valves, conduits, channels, and lines for supplying any of the fluids used in the invention.

The term "intracorporeal," as used herein means existing within the body.

The term "extracorporeal," as used herein means situated or occurring outside the body.

The term "effluent dialysate," as used herein describes the discharge or outflow after the dialysate has been used for dialysis.

The term "effluent filtrate," as used herein describes the waste filtered fluid from ultrafiltration.

Figure 52:
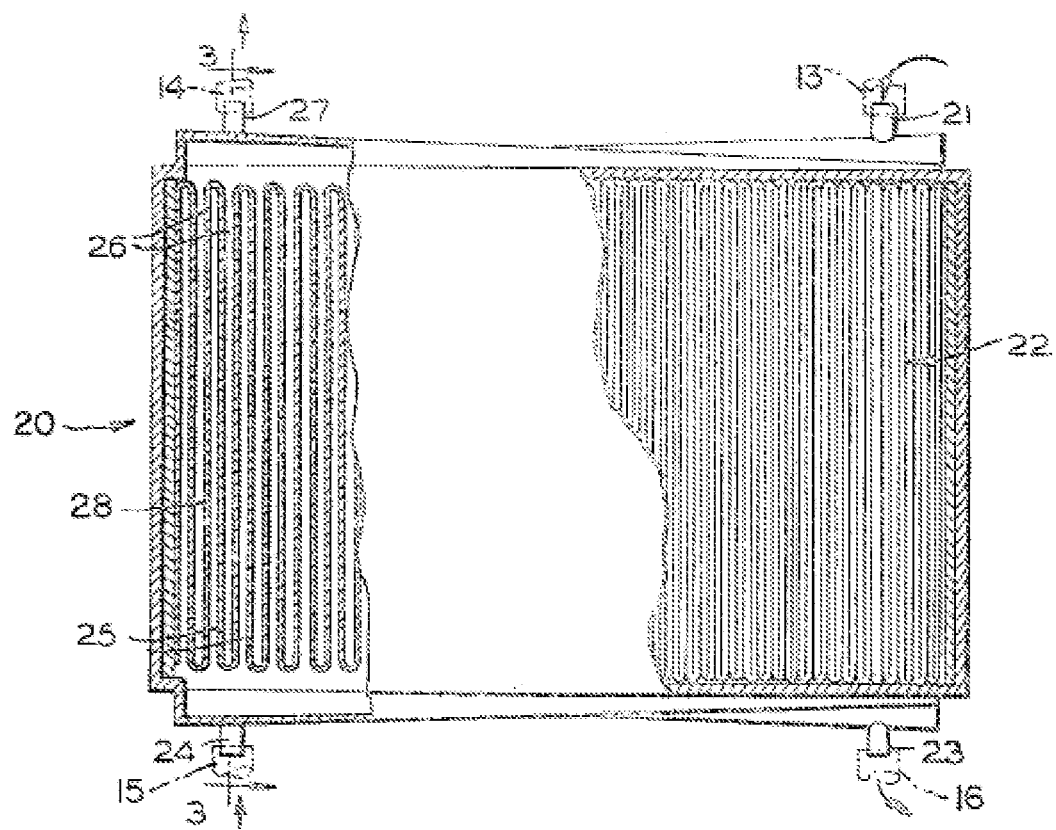
FIG. 52 is a cut-away view of a blood dialyzing apparatus showing the internal features of the apparatus.
Figure 53:
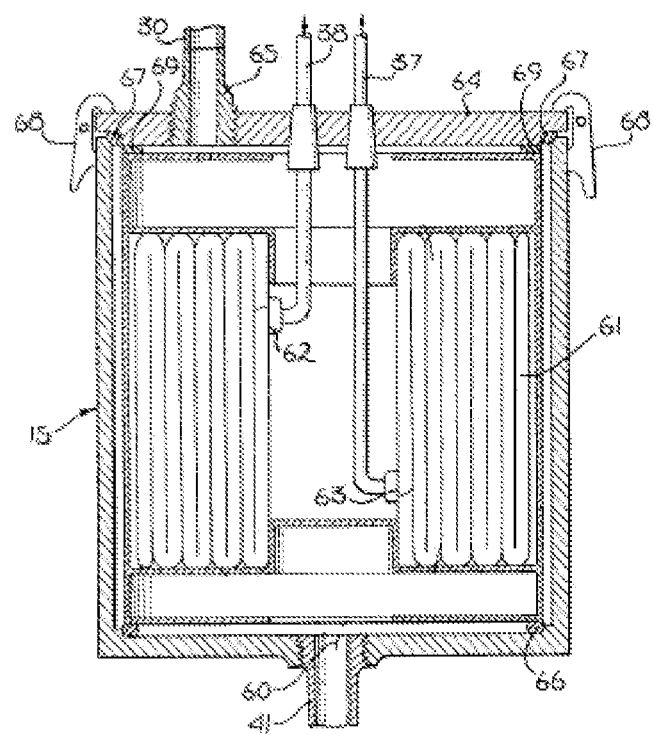
FIG. 53 is a schematic, partial cross-sectional view of a kidney coil holder.
Figure 54:
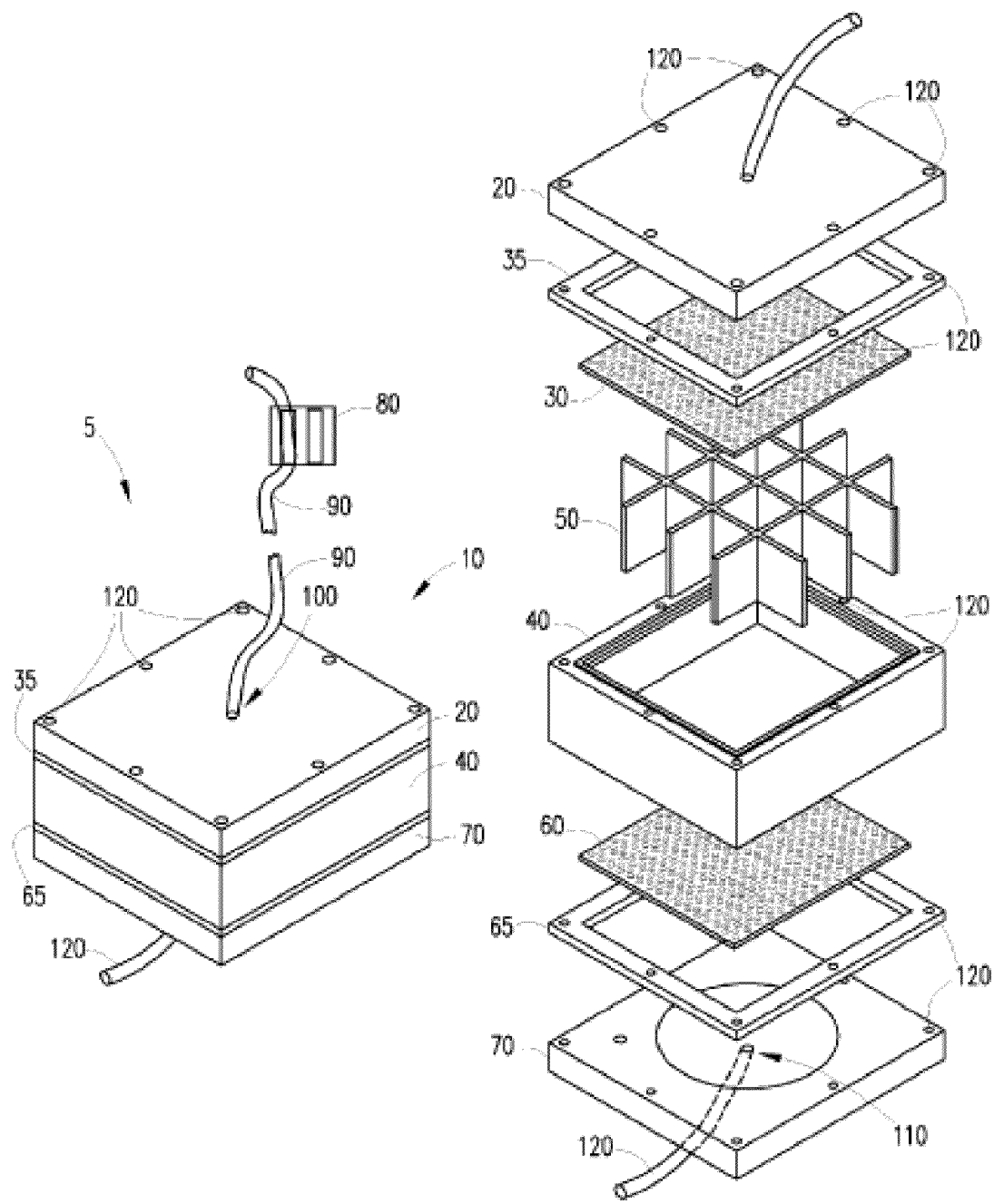
FIG. 54 shows an exploded view of a cartridge for treating biological fluid.
Figure 55:
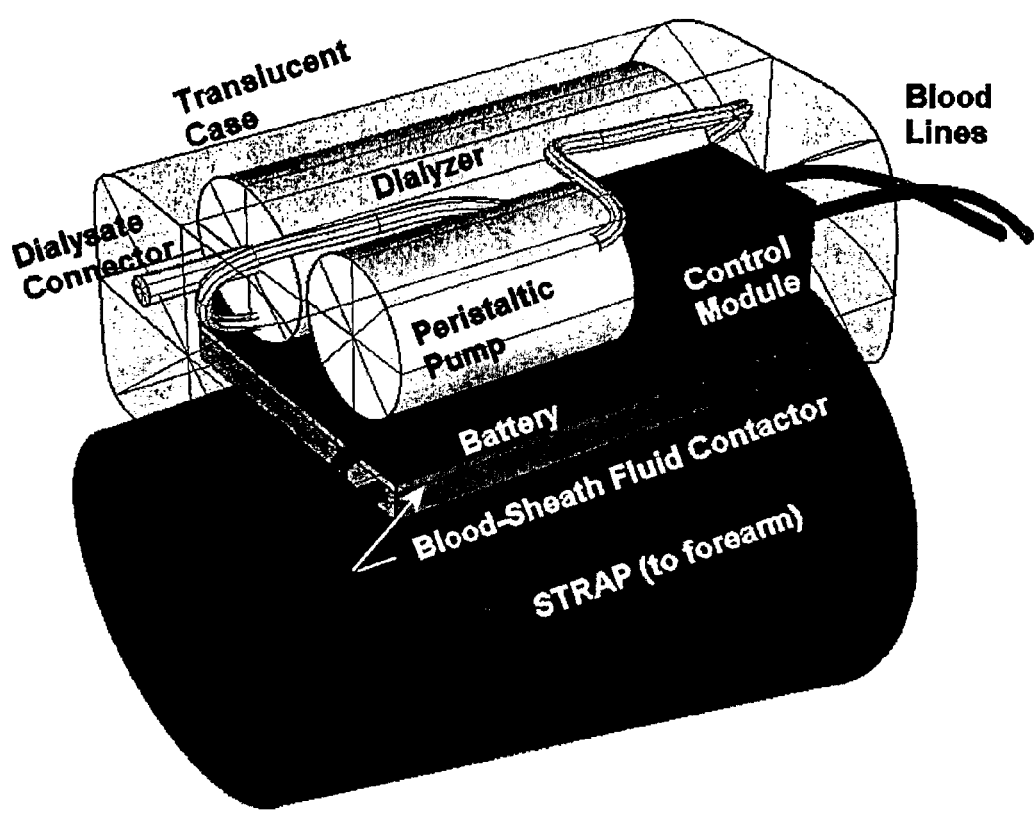
FIG. 55 is a schematic drawing of a wrist-size wearable dialysis system.
Figure 56:
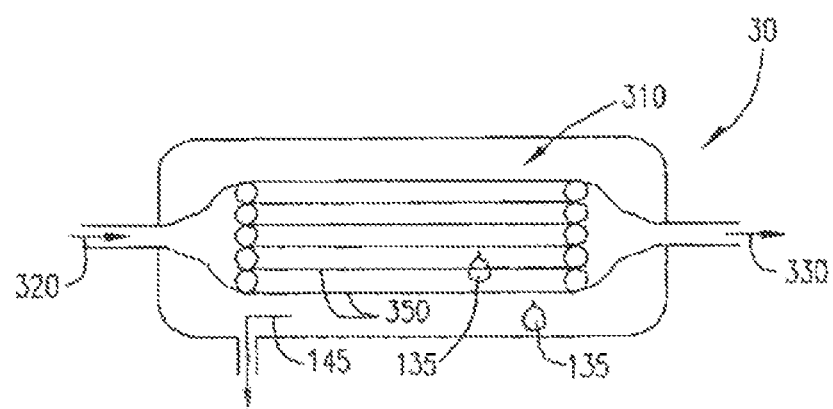
FIG. 56 is a perspective view of a wearable ultrafiltration device.

FIG. 52 is a figure from U.S. Pat. No. 3,370,710 showing a prior art blood dialyzing apparatus with a pleated membrane and having a first fluid inlet and outlet pair, and a second fluid inlet and outlet pair. FIG. 53 is a figure from U.S. Pat. No. 3,809,241 showing a prior art portable kidney coil of a portable dialysate delivery system. FIG. 54 is a figure from US 2008/0006570 showing a prior art chambered cartridge for treating medical or biological fluids. FIG. 55 is a figure from US 2006/0076295 showing a prior art wrist-wearable dialysis system having a dialyzer and a pump. FIG. 56 is a figure from US 2010/0022936 showing a prior art component of a wearable ultrafiltration device of a conventional blood filter comprising a plurality of hollow fibers through which the blood is circulated.

Implantable Dialyzer

In the medical systems of the present invention, one embodiment includes an implantable module or implantable dialyzer, percutaneous or subcutaneous ports and conduits, and an external module. The hemodialysis system includes an implantable module, a cutaneous module and an extracorporeal module as generally shown in FIG. 1. The implantable module is a dialyzer (or a filter) where the blood of the patient exchanges water, urea, NaCl, and other substances with the dialysate. In one embodiment, the implantable dialyzer can access the patient's blood via a pair of vascular grafts wherein the blood is drawn from the artery of the patient, fed into the device through an entry graft, and returned back to the vein through the exit graft. In other embodiments, the implanted dialyzer can access the dialysate supplied by the external module through percutaneous or subcutaneous ports and dialysate conduits. In one non-limiting example, the dialysate from a supply tank flows into an external conduit, passes a percutaneous or subcutaneous port and an implanted conduit, and enters the dialyzer. After cleaning the blood inside the dialyzer filter pack, the dialysate exits the dialyzer, passes through the implanted exit conduit, dialysate exit port, and another external conduit, and finally returns to the external module. In one embodiment, the blood circulation system is implantable while the dialysate circulation system is external. This configuration can be safer than an external blood circulation system as those used for in-center hemodialysis or wearable dialysis devices wherein the medical system performs dialysis at night and ultrafiltration during the day as need. Selectively performing hemodialysis and/or ultrafiltration is defined as control of which process is being performed wherein the filter pack exchanges water, urea, NaCl, and other electrolytes and waste substances with a dialysate during hemodialysis and removes water during ultrafiltration. System cleaning can be initiated as needed using the herein defined control or controls.

In certain embodiments, the implantable module has a geometry and volume to fit the anatomy of the patient for implantation. For example, the implantable dialyzer can have a volume no greater than about 300 cc in order to anatomically fit a patient for which that volume is appropriate. In other embodiment, the implantable dialyzer can have a greater or lesser volume. The implantation location should be close enough to the patient's blood access system to alleviate the need for long or complicated vascular graft paths, which might require high blood pressure to drive blood flow or leading to poor hemocompatibility. The cutaneous ports should be suitable for long term use. The ports may be similar to those used in peritoneal dialysis as known within the art. In one embodiment, the external module has a controller to control a dialysate supply tank when hemodialysis is conducted. Optionally, when ultrafiltration mode is used during daytime, the dialysate tank is disconnected from the patient. The system also contemplates an external container to collect filtrate (urine). Alternatively, the system uses an internal system to drain the filtrate to the bladder. The external module can also serve as a controller and supply tank for cleaning the dialyzer.

In one configuration, the individual components of the implantable dialyzer are a blood entry port that is a feed through-like component allowing blood to flow inside the device, a blood distribution manifold that allows for the blood to be uniformly distributed into all the alternating dialysate and blood membrane channels interposed between each membrane, and filters that are packed in a way in which the gaps between filters are filled with the blood and the dialysate in alternative rows to maximize mass transfer. The total filter area should be large enough to effectively remove the waste build-up within an intended patient. The filters are also configured for ultrafiltration to effectively remove liquid build-up. The implantable dialyzer has a blood collecting manifold to collect the cleaned blood, and a blood exit port that is a feed through-like component to port cleaned blood out of the implantable dialyzer. In certain embodiments, the implantable dialyzer also has two dialysate manifolds, one dialysate entry port and one exit port. Optionally, the implantable dialyzer can have two blood regulation valves, one distal to blood entry and the other proximal to blood exit. Two cross valves, one between the dialysate entry and the blood exit, and the other between the blood exit and the dialysate entry, are also contemplated by the invention. The valves are limited to any specific type of cross valve can be any valve used within the art suitable for biomedical applications. In other embodiments, a blood pump distal to the blood entry port and an implantable rechargeable battery to power the pump and valves are contemplated.

For certain embodiments of the medical system, peripheral components can include two blood grafts connecting the device with the blood, vessels of the patient, two dialysate conduits to connect the device with percutaneous or subcutaneous dialysate ports, an electrical cable to supply power for the pump, valves, and two external dialysate conduits to connect the percutaneous or subcutaneous ports for the dialysate circulation between the external modules and implanted dialyzer.

In one configuration, the blood flow path is from the artery, feed graft, entry feed-port, distribution manifold, filter gaps, collecting manifold, exit feed-port, returning graft, and vein. The driving force for the blood flow can be the heart of the patient. Optionally, if high pressure is needed to drive the blood flow through the path, an implantable blood pump may be used. This pump can be driven by implanted rechargeable batteries, external electrical power supply, an externally supplied magnetic field, or hydraulic power.

Figure 2:
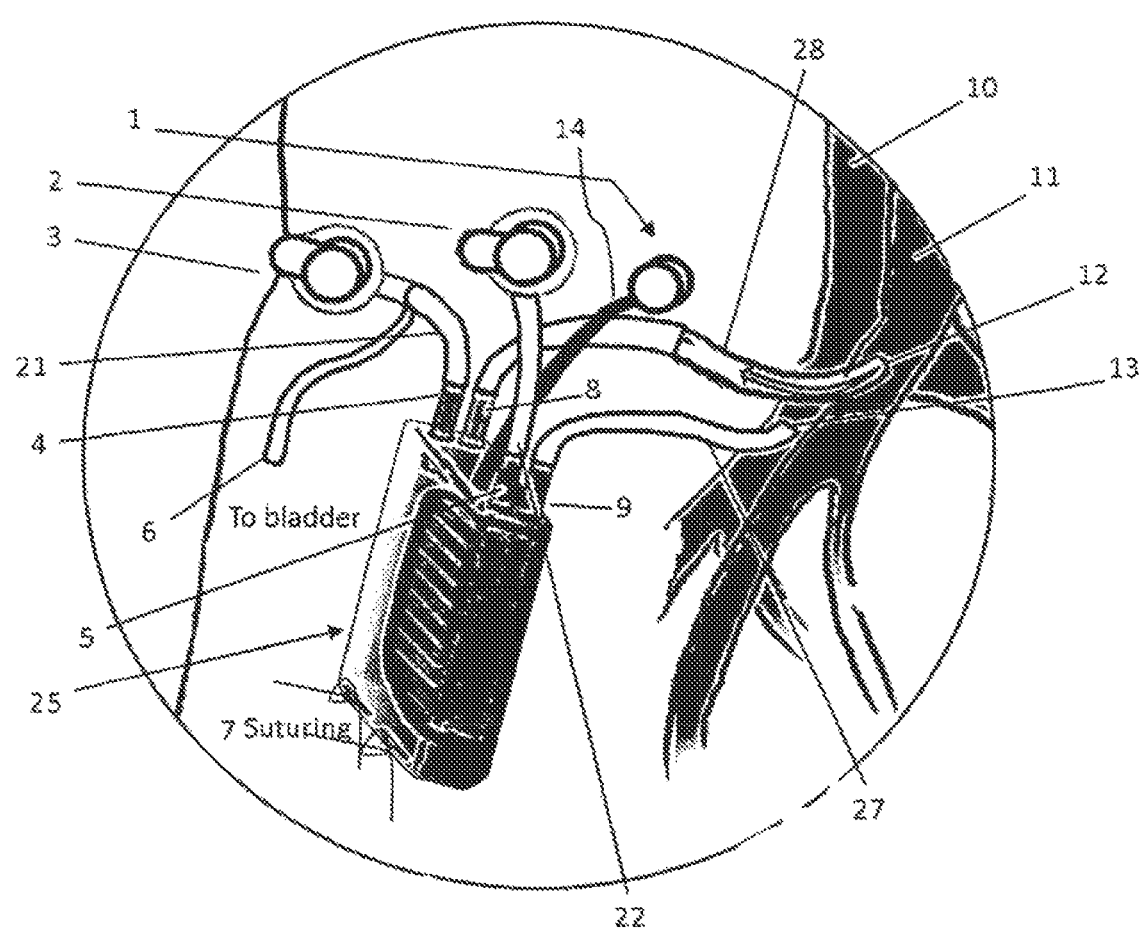
FIG. 2 shows the connections of a cutaneous module and an implantable module of the hemodialysis system implanted within a patient.

Referring to FIG. 2, an implantable dialyzer 25 and cutaneous module of a hemodialysis system are provided. The implantable dialyzer 25 is implanted in close proximity to a patient's vasculature to accommodate vascular access. The cutaneous module includes a percutaneous or subcutaneous dialysate feed port 2, a percutaneous or subcutaneous dialysate return port 3, and a percutaneous electric cable port 1. Percutaneous ports of the system are similar to the ports used in peritoneal dialysis, and are suitable for long term use. Each percutaneous port has an internal and external adapter for connectivity. Subcutaneous ports of the system are implanted below the patient's skin. Either type of port resists inflammation, and is conducive to sterilization and the promotion of healing at the access site on the patient. Internally, the dialysate feed port 2 is connected to a dialysate inlet 5 of the implantable dialyzer by dialysate feed tubing 22. The dialysate return port 3 is connected to a dialysate outlet 4 of the implantable dialyzer 25 by dialysate return tubing 21. An optional drain tube 6 grafted to the patient's bladder connects the dialysate return tubing 21 to the patient's bladder. The dialysate feed tubing 22, dialysate return tubing 21, and optional drain tube 6 are constructed of a biocompatible polymer such as silicone, polyurethane, or Dacron. In one embodiment, the tubes constructing the dialysate feed tubing 22, dialysate return tubing 21, and drain tube 6 are catheters having an outer diameter of about 0.7 to about 1.0 cm, an inner diameter of about 0.5 to about 0.7 cm and a length of about 30 cm. The percutaneous electric cable port 1 can be connected to the implantable dialyzer 25 by an electric cable 14.

An arterial graft 12 is grafted to an artery 11 and connects to a blood inlet 8 of the implantable dialyzer 25 by blood feed tubing 28. A venous graft 13 is grafted to a vein 10 and connects to a blood outlet 9 of the implantable dialyzer 25 by blood return tubing 27. The blood feed tubing 28, and the blood return tubing 27 are constructed of a biocompatible polymer such as polytetrafluoroethylene. In one embodiment, the tubes constructing the blood feed tubing 28, and the blood return tubing 27 are catheters having an outer diameter of about 0.7 cm, an inner diameter of about 0.5 cm and a length of about 20 cm. Suturing 7 fixes the implantable dialyzer to a patient's internal tissue in certain models.

Figure 3:
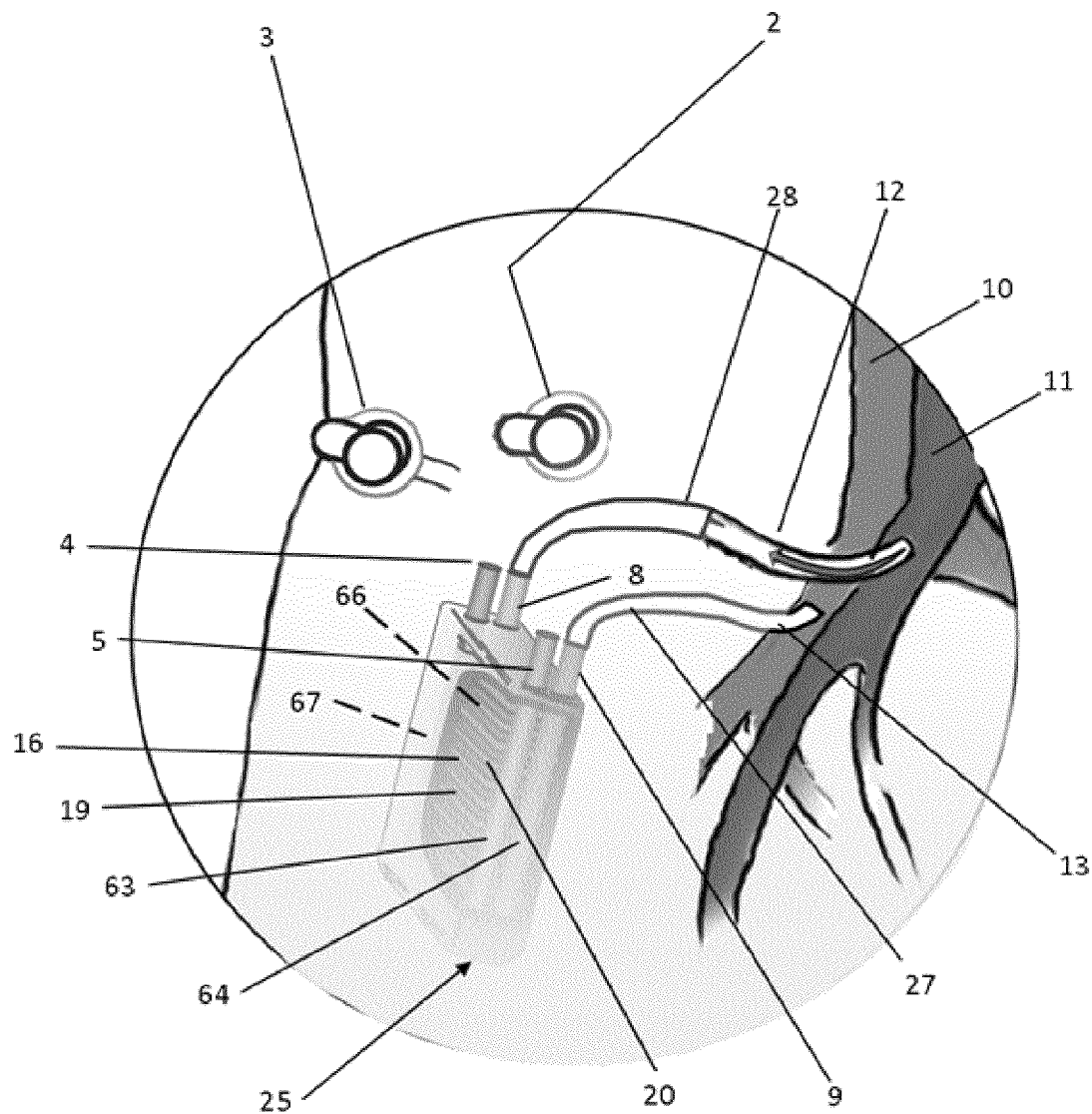
FIG. 3 shows an alternative view of the cutaneous and implantable modules of FIG. 2 implanted within a patient.

FIG. 3 shows additional details of one embodiment the implantable dialyzer 25 wherein the dialysate inlet 5 connects to a dialysate feed manifold 63 within the implantable dialyzer 25. The dialysate feed manifold 63 connects to a plurality of dialysate membrane channels 16 within a membrane stack 20. Additionally, the plurality of dialysate membrane channels 16 each connect to a dialysate return manifold 67. The dialysate outlet 4 connects to the dialysate return manifold 67 within the implantable dialyzer 25. The blood inlet 8 connects to a blood feed manifold 66. The blood feed manifold 66 connects to a plurality of blood membrane channels 19 within the membrane stack 20. Additionally, the plurality of blood membrane channels 19 each connect to a blood return manifold 64, and the blood outlet 9 connects to the blood return manifold 64.

As shown by FIGS. 2 and 3, arterial blood from a patient can be fed into the implantable dialyzer 25 from a patient's artery 11. Blood is returned from the implantable dialyzer 25 to a patient's vein 10. A blood flow path through the implantable dialyzer 25 is described as follows for this embodiment. Arterial blood flows from an artery 11 via an arterial graft 12 which is connected to the blood feed tubing 28. Blood flows through the blood feed tubing 28 and into the blood inlet 8 of the implantable dialyzer 25. The blood inlet 8 connects to the blood feed manifold 66 which distributes the blood to a plurality of blood membrane channels 19 within the membrane stack 20. The blood flows through the blood membrane channels 19 into the blood return manifold 64, and exits the implantable dialyzer 25 through the blood outlet 9. The blood is returned to a patient's vein 9 via the blood return tubing 27 and a venous graft 13.

As also shown by FIGS. 2 and 3, dialysate can be fed into implantable dialyzer 25 via the percutaneous or subcutaneous dialysate feed port 2 in certain embodiments. Dialysate is returned from the implantable dialyzer 25, to the percutaneous or subcutaneous dialysate return port 3. One dialysate flow path through the implantable dialyzer 25 is described as follows. Dialysate flows through the dialysate feed port 2 which is connected to the dialysate feed tubing 22. The dialysate flows through the dialysate feed tubing 22 and into the dialysate inlet 5 of the implantable dialyzer 25. The dialysate inlet 5 connects to the dialysate feed manifold 63 which distributes the dialysate to a plurality of dialysate membrane channels 16 within the membrane stack 20. The dialysate flows through the dialysate membrane channels 16 into the dialysate return manifold 67 and exits the implantable dialyzer 25 through the dialysate outlet 4. The dialysate is returned through the dialysate return tubing 21 and to the dialysate return port 3.

The hemodialysis system performs dialysis by feeding fresh dialysate through the dialysate flow path, and blood from a patient through the blood flow path. The patient's blood is dialyzed by the dialysate within the implantable dialyzer 25 via mass transfer across a filter media. During dialysis, blood waste components such as urea, creatinine, and NaCl are transported by diffusion across the filter media to the dialysate. The composition and flow rate of the dialysate, and the duration of dialysate circulation can be determined by a prescribing physician, technician, or operator. Dialysate is driven through the dialysate flow path by an external pump. Blood is driven through the blood flow path by the patient's arteriovenous blood pressure. Alternatively, an optional blood pump located within the implantable dialyzer 25 can drive blood through the blood path. The optional blood pump may be powered by a rechargeable battery worn externally by the patient, and connected by electric cable 14 to the implantable dialyzer 25 via the percutaneous electric cable port 1. The blood pump may also be powered by a rechargeable battery within the implantable dialyzer 25. Alternatively, the blood pump may be driven by an externally supplied magnetic field, or hydraulic power.

In certain embodiments, the hemodialysis system performs hemodialysis and ultrafiltration by feeding blood from a patient through the blood flow path. During ultrafiltration, filtrate from the blood can be transported by convection across the filter media and collected in the plurality of dialysate membrane channels 16 of the implantable dialyzer 25.

The filtrate is removed via, the dialysate return manifold 67 and percutaneous or subcutaneous dialysate return port 3 of the dialysate flow path. Alternatively, the filtrate may be directed to the patient's bladder via drain tube 6. Blood is driven through the blood flow path by the patient's arteriovenous blood pressure. Alternatively, an optional blood pump located within the implantable dialyzer 25 can drive blood through the blood path. The optional blood pump may be powered by a rechargeable battery worn externally by the patient, and connected by electric cable 14 to the implantable dialyzer 25 via the percutaneous electric cable port 1. The blood pump may also be powered by a rechargeable battery within the implantable dialyzer 25. Alternatively, the blood pump may be driven by an externally supplied electrical source, magnetic field, or hydraulic power.

Figure 4:
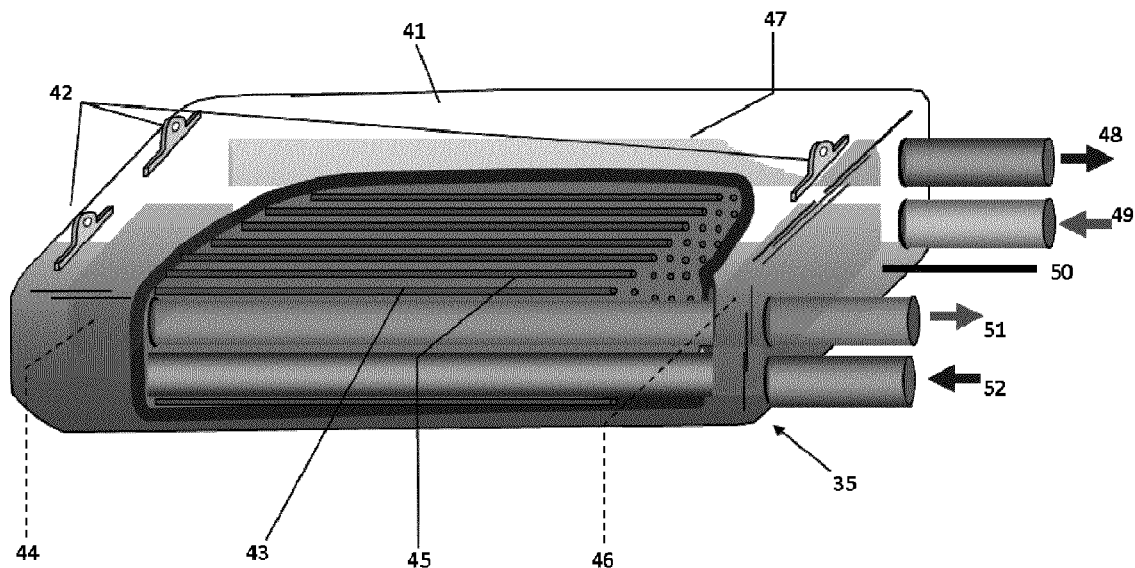
FIG. 4 is a cut-away view of an embodiment of an implantable module of the hemodialysis system having a bundled fiber filter.

One version of an implantable dialyzer 35 having a bundled fiber filter is shown in FIG. 4. A blood inlet 49 directs blood to a blood feed distributor 46 within the implantable dialyzer 35. The blood flow distributor 46 distributes blood to a plurality of fibers 45. Blood within the plurality of fibers 45 is dialyzed by a dialysate flowing through a dialysate compartment 43 surrounding said fibers. Once dialyzed, the blood is collected in a blood return collector 44, and directed out of the implantable module 35 via a blood outlet 51. A dialysate inlet 52 directs dialysate to the dialysate compartment 43. Dialysate within the dialysate compartment 43 dialyzes blood flowing, through the plurality of fibers 45. Dialysate is directed out of the implantable module 35 via a dialysate outlet 48. A casing 41 encapsulates the internal features of implantable module 35. The casing 41 can be constructed of a biocompatible material such as titanium. Unoccupied space within the casing 41 is suitable for housing additional components such, as valves, an optional blood pump, and a rechargeable battery. Suturing holes 42 on the casing, 41 attach the implantable module 35 to a patient's internal tissue via suturing. An electrical cable 50 connects valves within the implantable module 35 to an extracorporeal module.

In one non-limiting embodiment, the implantable module 35 can measure from about 3.0 cm×7.6 cm×12.7 cm and may have an approximate volume of about 300 cm$^3$. However, the size and geometry of the module can depend upon parameters including patient size and internal physical geometry of the surgical implantation site, blood volume intended to be dialyzed, and type of membranes being used. The fibers 45 may be made of polycarbonate, polysulfone, poly(ether sulfone), poly(methyl methacrylate), polyethylene, polyamide, polyacrylonitrile, poly(ethylene vinyl alcohol), and cellulose acetate or modified cellulose. In certain embodiments, the fibers can have a hydraulic permeability greater than or equal to from around 0.5 mL/min·m2·mmHg, a diffusive permeability, greater than or equal to from around 0.00015 cm/s, and an albumin sieve coefficient less than or equal to from around 0.01. In one embodiment, the implantable module 35 can have from about 1088 cm$^2$ of filtration area derived from about 1733' hollow fibers with a packing density of about 0.9. Each hollow fiber can have an outer diameter of about 0.1 cm, an inner, diameter of about 0.02 cm, and a length of about 10 cm. In one non-limiting example, space for an optional blood pump measures from about 2.0 cm×2.5 cm×3.0 cm and space for additional components such as a rechargeable battery and valves can measure from about 2.0 cm×2.5 cm×2.0 cm.

Figure 5:
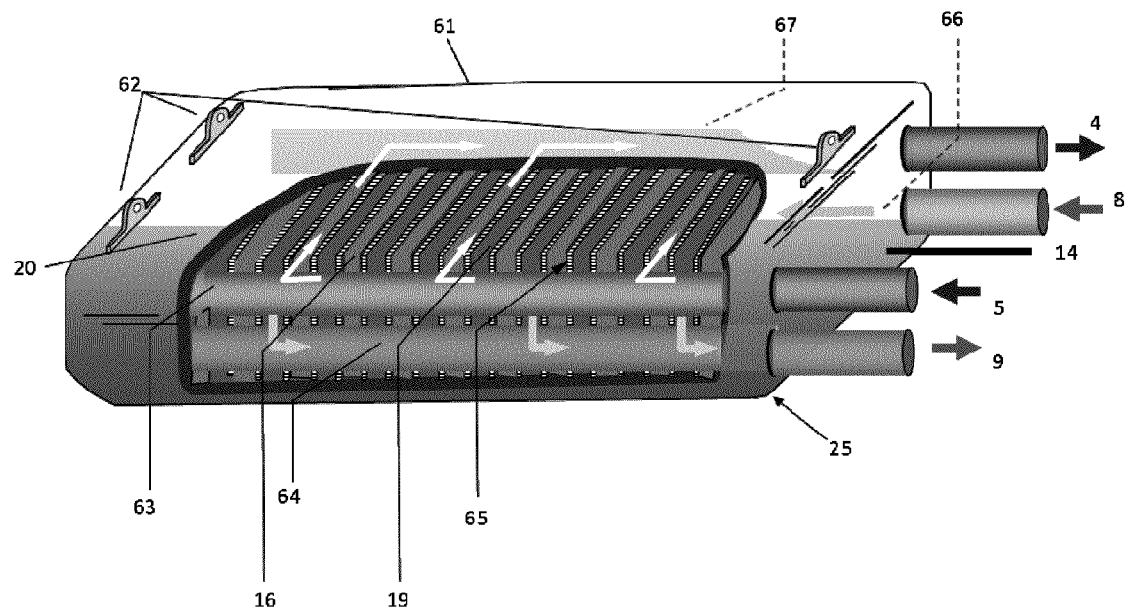
FIG. 5 is a cut-away view of the implantable module of FIGS. 2 and 3 having a stacked membrane filter.

One embodiment of the implantable module 25 is shown in greater detail in FIG. 5. The plurality of dialysate membrane channels 16 and blood membrane channels 19 can interface with a plurality of membrane filter elements 65 within the membrane stack 20. During hemodialysis, blood, flowing, through the blood flow path is dialyzed by dialysate flowing through the dialysate flow-path. Dialysis of the blood can occur via mass transfer across the plurality of membrane filter elements 65 within the membrane stack 20. A casing 61 encapsulates the internal features of the implantable module 25. The casing 61 is constructed of a biocompatible material such as titanium. Unoccupied space within the casing 61 is suitable for housing additional components such as valves, an optional blood pump, and a rechargeable battery. Suturing holes 62 on the casing 61 attach the implantable module 25 to a patient's internal tissue via suturing. An electrical cable 14 can connect valves within the implantable module 25 to an extracorporeal module.

Figure 6:
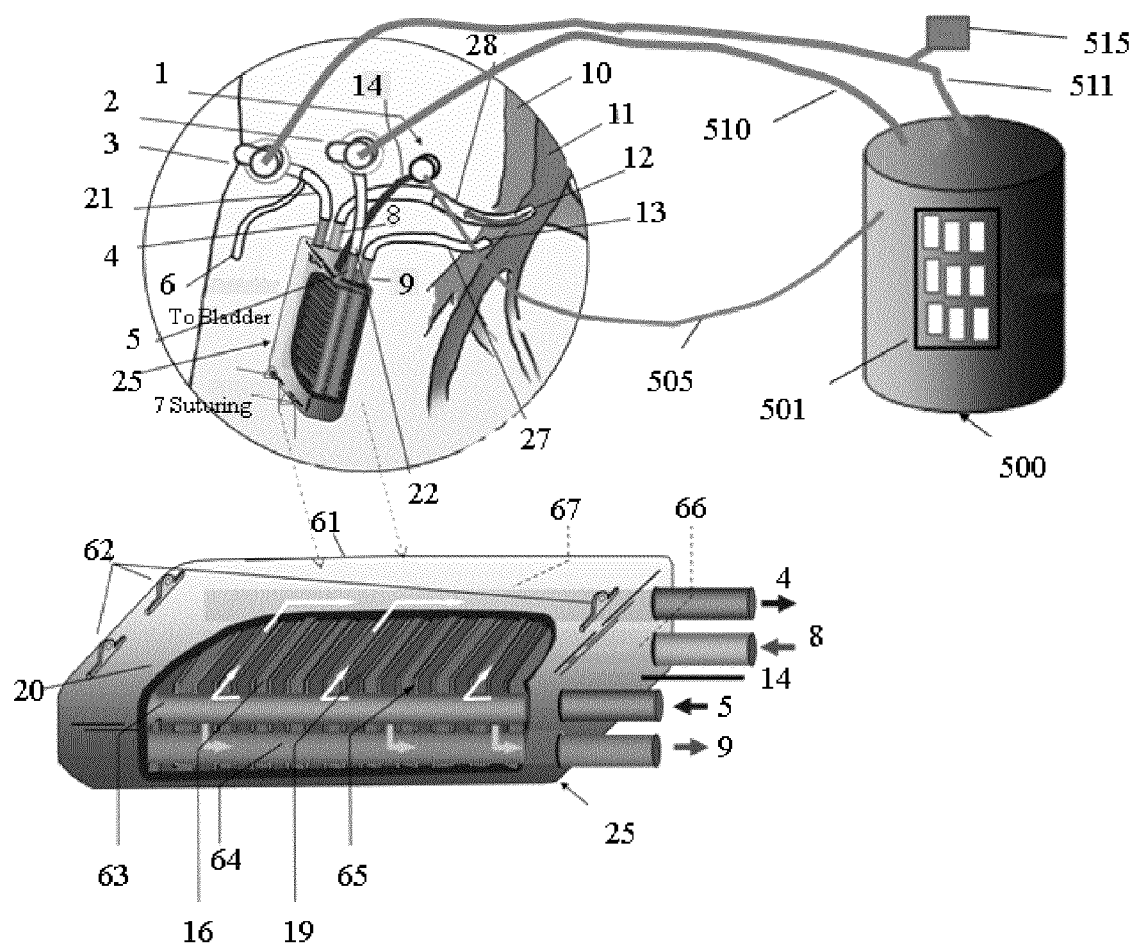
FIG. 6 shows the connections of all three modules of the hemodialysis system.

Referring to FIG. 6, one embodiment of the extracorporeal module 500 is connected to the implantable module 25 via the percutaneous or subcutaneous dialysate feed port 2, the percutaneous or subcutaneous dialysate return port 4, and the percutaneous electric cable port 1. The dialysate feed port 2 is connected to the extracorporeal module 500 by an extracorporeal dialysate feed tubing 510. The dialysate return port 4 is connected to the extracorporeal module 500 by an extracorporeal dialysate return tubing 511. The percutaneous electric cable port 1 is connected to the extracorporeal module 500 by an extracorporeal electrical cable 505. An optional urine collection bag 515 is connected to the extracorporeal dialysate return tubing 511 between the dialysate return port 4 and the extracorporeal module 500. A control unit 501 is located on the extracorporeal module 500 and controls of the functions of the hemodiafiltration system. The control unit 501 includes an input device, a display, a processing unit, a data link, and software.

Figure 7:
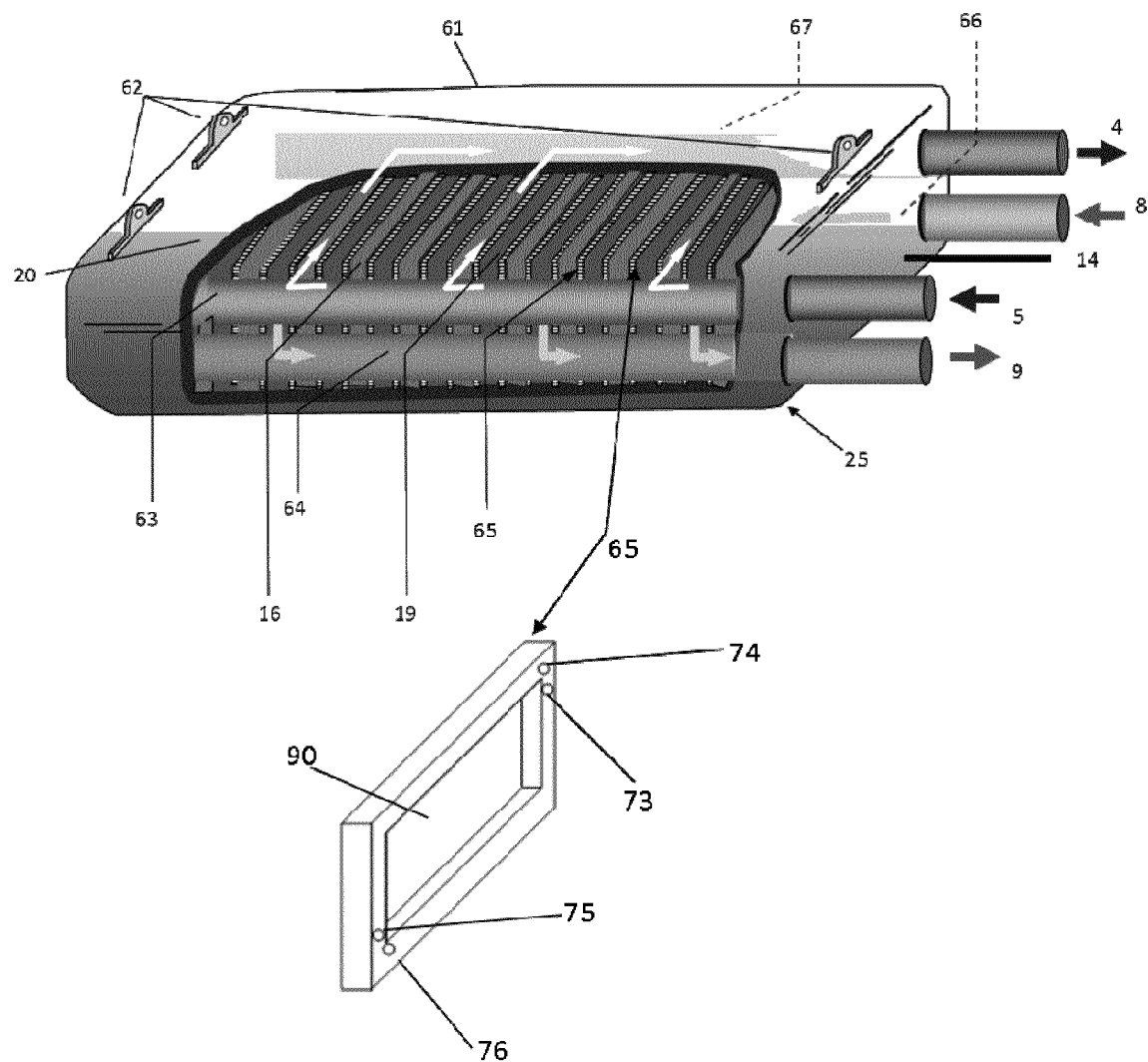
FIG. 7 shows a membrane filter element as it relates to the implantable module of FIG. 5.
Figure 8:
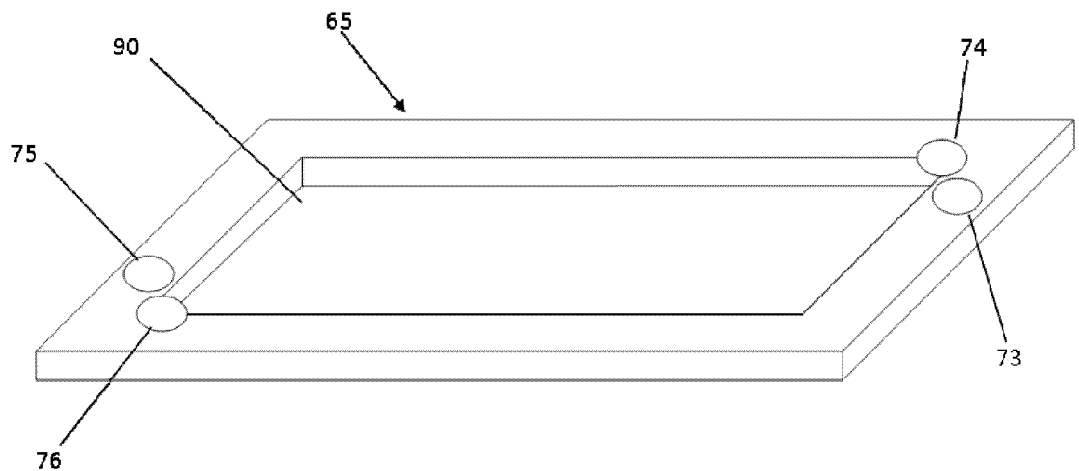
FIG. 8 is a perspective view of the membrane filter element of FIG. 7.

FIG. 7 shows one of a plurality of membrane filter elements 65 in relation to the implantable module 25. Each membrane filter element 65 includes a membrane 90 and is stacked within the implantable module housing 25 to form the membrane stack 20. The features of a single membrane filter element 65 cooperate with the features of adjacent filter elements within the membrane stack 20 as follows. The blood feed manifold 66 is formed by a plurality of stacked blood feed manifold sections 74. The blood return manifold 64 is formed by a plurality of stacked blood return manifold sections 76. The dialysate feed manifold 63 is formed by a plurality of stacked dialysate feed manifold sections 75. Dialysate return manifold 67 is formed by a plurality of stacked dialysate return manifold sections 73. A second view of a membrane filter element 65 having a membrane 90 is shown in FIG. 8 wherein the locations of the blood feed manifold section 74, blood return manifold section 76, dialysate feed manifold section 75, and dialysate return manifold section 73 are shown.

In one non-limiting example, the implantable module 25 can measure from about 3.0 cm×7.6 cm×12.7 cm and may have an approximate volume from about 300 cm$^3$. An embodiment of the implantable module 25 has from about 1020 cm$^2$ of filtration area derived from about 68 membrane filter elements 65 spaced about 0.05 cm. Each membrane filter measures about 0.1 cm×2.5 cm×6.0 cm. Any one of the distribution manifolds can measure about 12.0 cm×1.0 cm×0.5 cm. In one non-limiting example, space for an optional blood pump measures from 2.0 cm×2.5 cm×3.0 cm. Space for additional components such as a rechargeable battery and valves measures from 2.0 cm×2.5 cm×2.0 cm.

Figure 9:
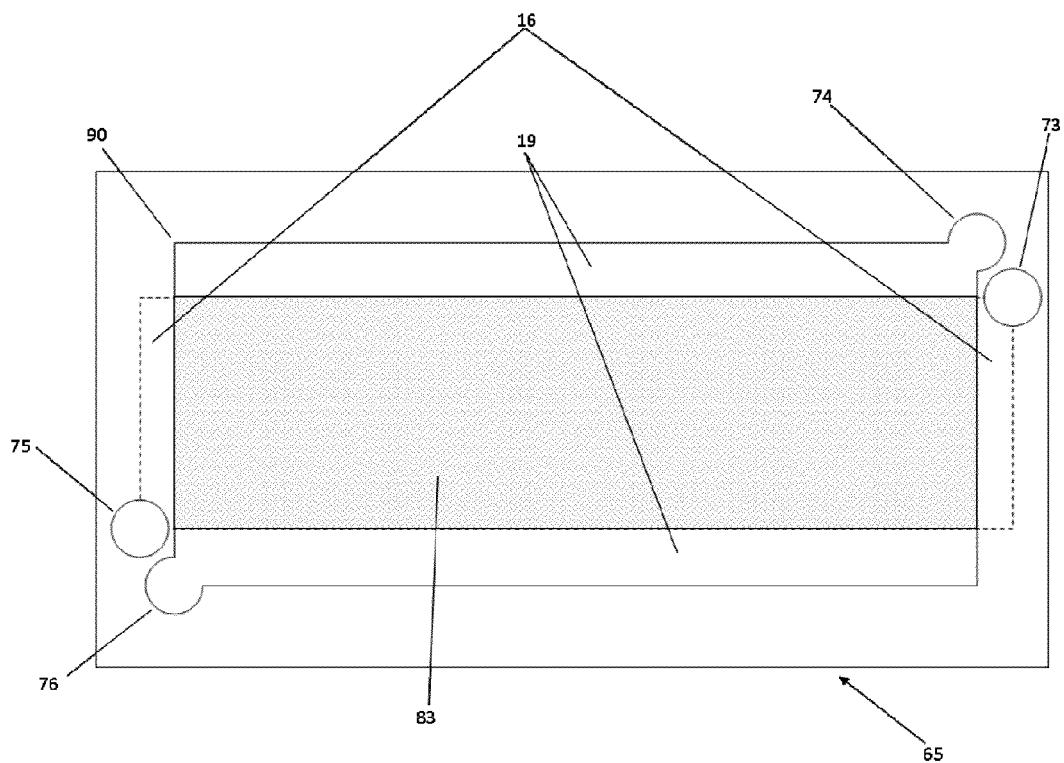
FIG. 9 is a top view of the membrane filter element of FIG. 7.

Features of a membrane filter element 65 are shown in greater detail in FIG. 9. In one embodiment, a blood membrane channel 19 forms a blood flow path on a first side of a membrane 90, and a dialysate membrane channel 16 forms a dialysate flow path on a second side of said membrane 90. The area of overlap of the blood membrane channel 19 and the dialysate membrane channel 16 forms an active membrane area 83 of membrane 90 across which mass transfer occurs between blood and dialysate. The arrangement of each blood and dialysate membrane channels is such that the flows of dialysate and blood therein are directed tangentially across the membrane surface to produce a cross-flow membrane interface. The cross-flow membrane interface enables continuous blood-membrane and dialysate-membrane exposure without significant buildup of solutes on the membrane, thus preserving membrane patency by keeping the filter media in a non-blinded and non-fouled state.

The membranes 90 of the implantable module 25 may be made of polycarbonate, polysulfone, poly(ether sulfone), poly(methyl methacrylate), polyethylene, polyamide, polyacrylonitrile, poly(ethylene vinyl alcohol), cellulose, or MEMS-based silicon. Said membranes, have a hydraulic permeability greater than 0.5 mL/min·m2·mmHg, a diffusive permeability greater than 0.00015 cm/s, and an albumin sieve coefficient less than 0.01.

Figure 10:
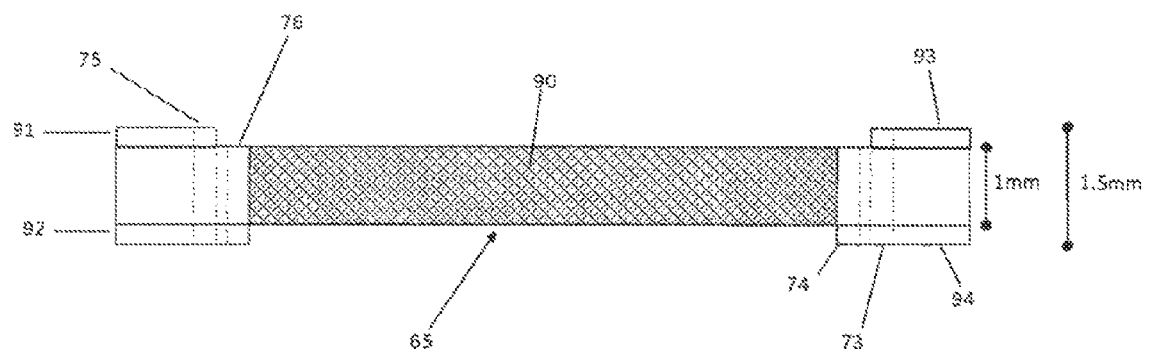
FIG. 10 is a side view of the membrane filter element of FIG. 7.

Non-limiting dimensions and additional features of a membrane filter element 65 are shown in FIG. 10. A first gasket A 91 is positioned above the dialysate feed manifold section 75 and a second gasket B 92 is positioned below both of the dialysate feed manifold section 75 and the blood return manifold section 76 as shown in FIG. 10. A third gasket C 93 is positioned above the dialysate return manifold section 73 and a fourth gasket D 94 is positioned below both of the dialysate return manifold, section 73 and the blood feed manifold section 74 as shown in FIG. 10.

Figure 11:
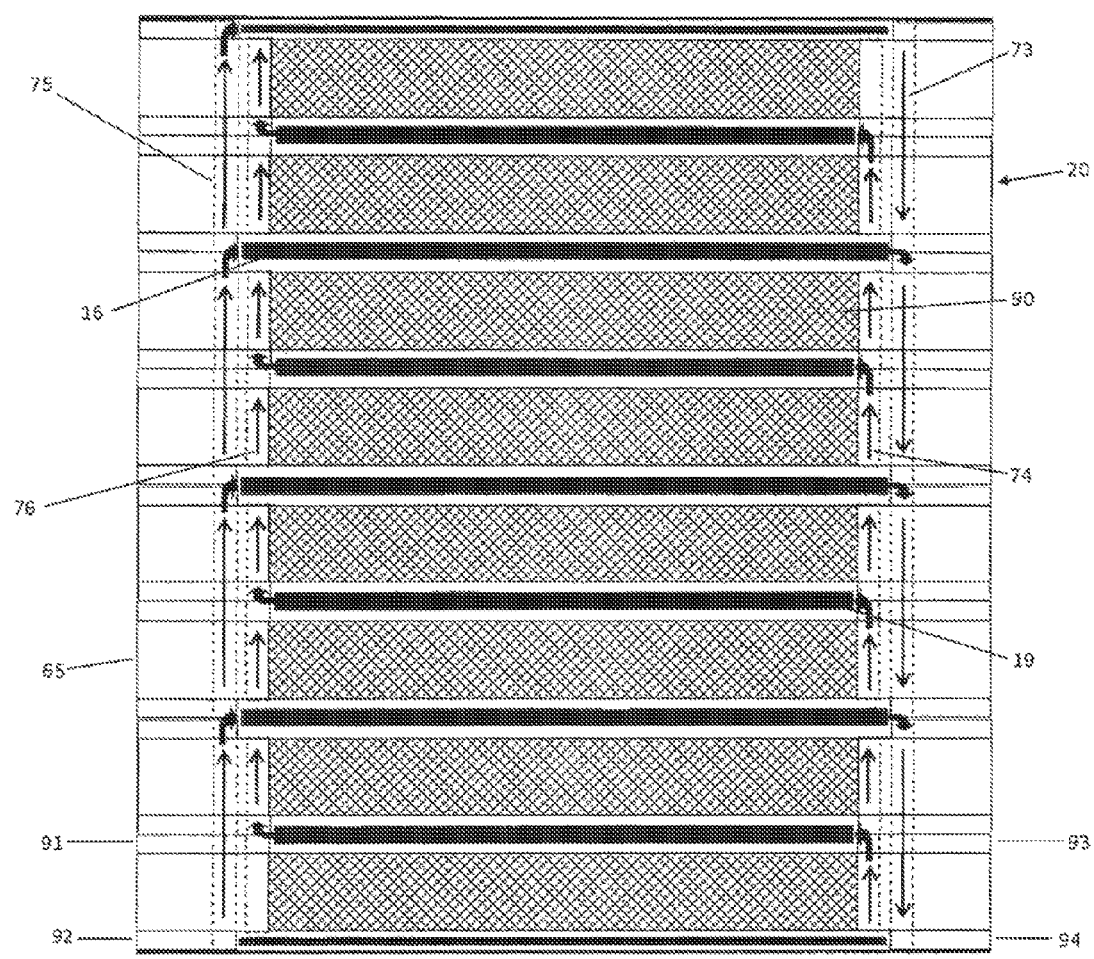
FIG. 11 is a side view of a membrane stack composed of a stack of membrane filter elements from FIG. 7.

FIG. 11 shows a non-limiting example of a plurality of stacked membrane filter elements 65. Gasket A 91 on each, membrane filter element 65 seals with gasket B 92 on an adjacent membrane filter element 65. Gasket C 93 on each membrane filter element 65 seals with gasket ID 94 on an adjacent membrane filter element 65. Said gaskets seal the blood feed manifold section 74, blood return manifold section 76, dialysate feed manifold section 75, and dialysate return manifold section 73 dialysate of each membrane filter element 65 with the corresponding sections on adjacent filter elements as shown in FIG. 11. Thus said sections form the blood feed manifold 66, blood return manifold 64, dialysate feed manifold 63, and dialysate return manifold 67 shown in the preceding figures.

Figure 12:
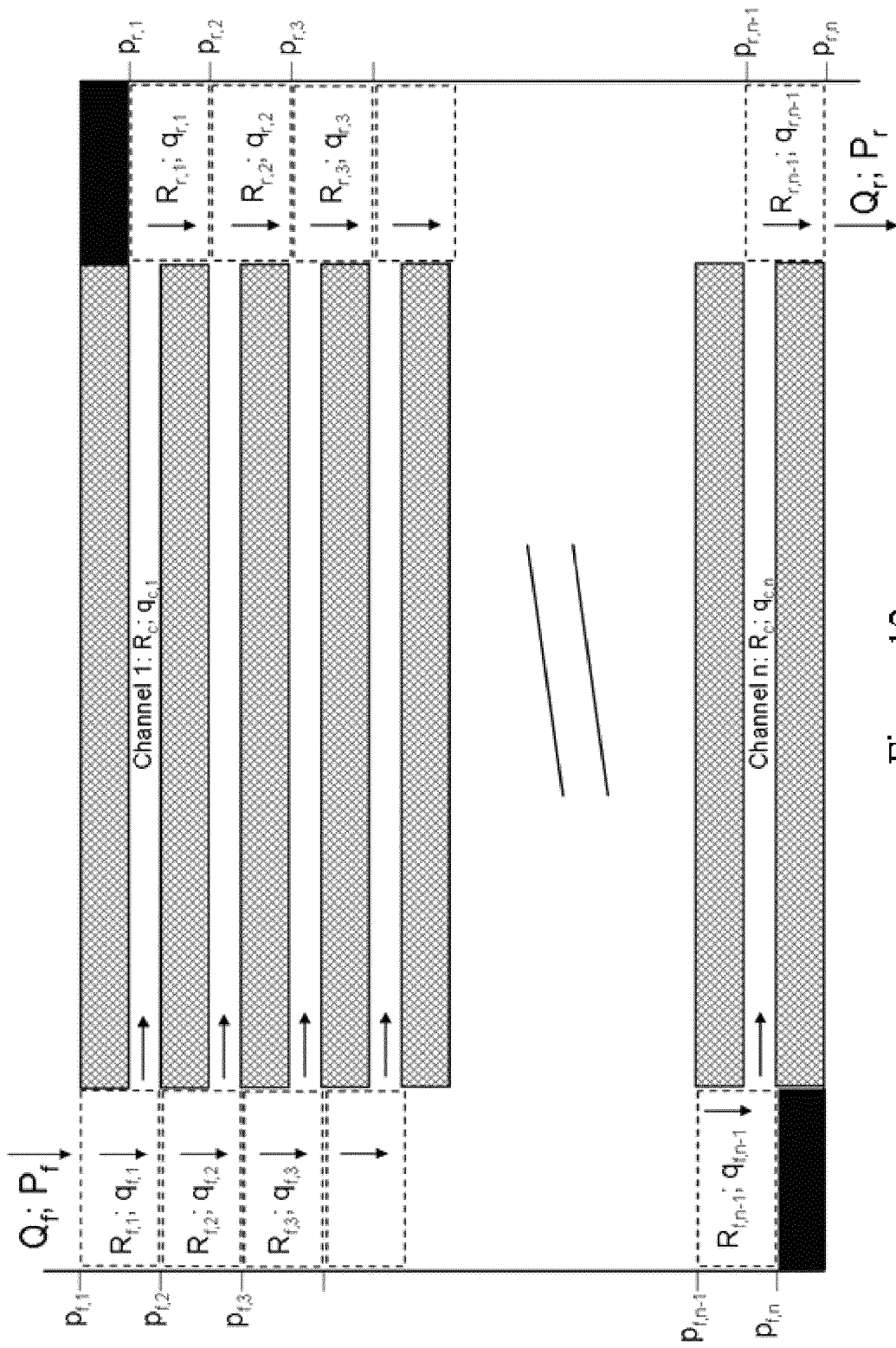
FIG. 12 is a flow diagram showing a simplified flow model through a stacked membrane filter having n stacked membranes.

Fluid properties through a stack of membrane filter elements such as membrane stack 20 in FIG. 11 are modeled by a simplified flow diagram through n stacked membrane filters as shown in FIG. 12. Fluid is fed into the model at rate $Q_f$ and pressure $P_f$. Feed and return manifold sections are separated into elements shown by dashed boxes. For each element, the fluid flows through either membrane channel n at rate $q_{c,n}$, or through corresponding feed manifold section n at rate $q_{r,n}$. Fluid that has passed through membrane channel n exits the membrane channel into corresponding return manifold section n at rate $q_{r,n}$. Fluid exits the model with final flow rate $Q_r$ and pressure $P_r$. Each feed manifold section n has a unique resistance $R_{f,n}$ and flow rate $q_{r,n}$. Each return manifold section n has a unique resistance $R_{r,n}$ and flow rate $q_{r,n}$. The resistance in any membrane channel is $R_c$.

Figure 13:
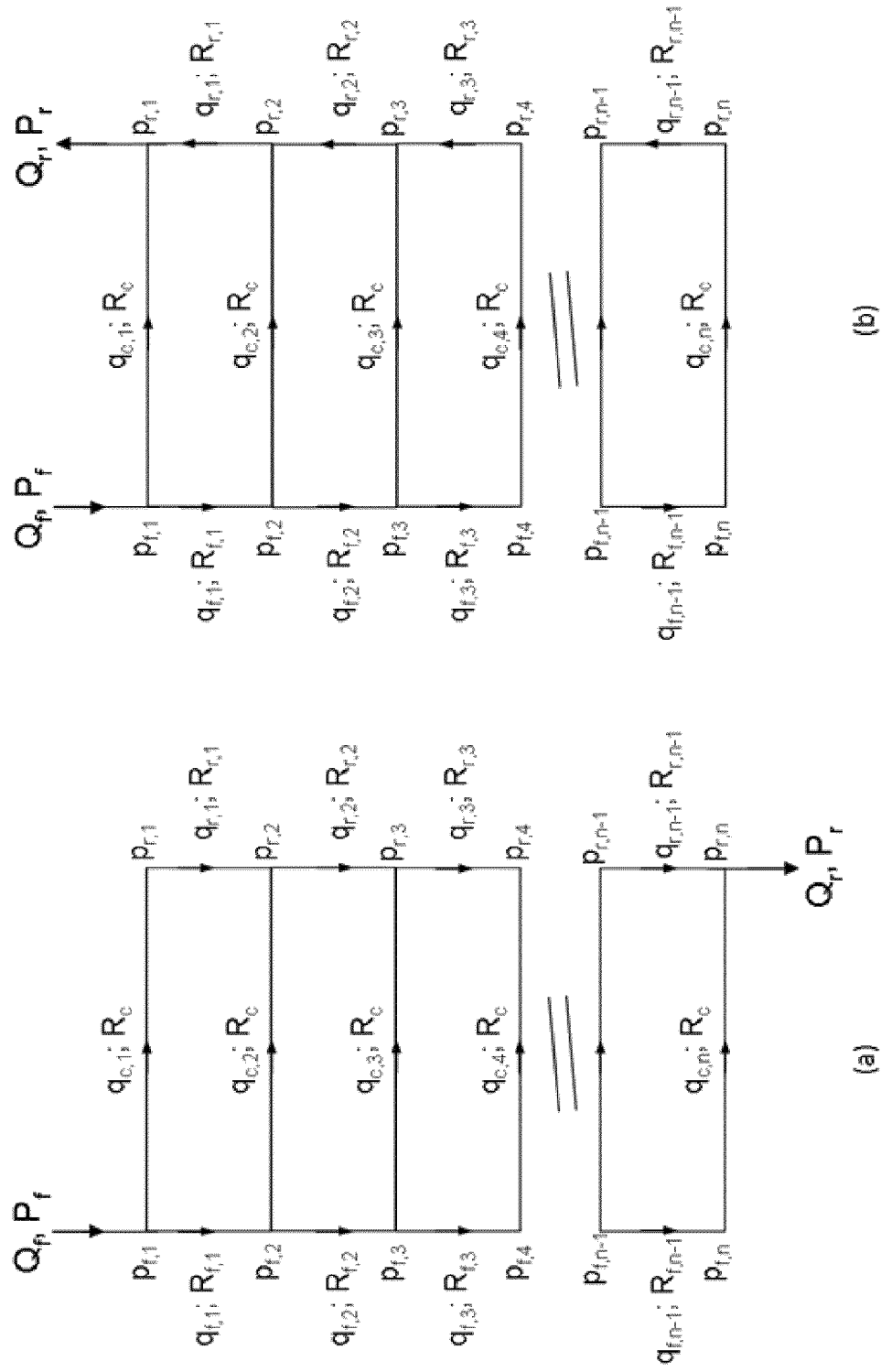
FIG. 13 shows circuit diagrams for flow through a stacked membrane filter having "n" stacked membranes.

The hemodialysis and ultrafiltration functions of the hemodialysis system are governed in part by the design of the fluid channels and filter pack within the implantable module housing. The type and arrangement of filter media influence fluid flow rate, pressure, filtration rate, and diffusive flux within the system. Moreover, these properties all impact diffusive mass transfer across the filter media, and thus determine the effectiveness of hemodialysis performed within the system. FIGS. 12 and 13 show simplified flow models through a filter pack having n stacked membrane filters.

The rate and pressure of blood flow through the hemodialysis system are significant because these properties impact diffusive mass transfer across the filter medium. These properties are largely determined by channel and conduit geometry. Fluid flow between membrane filters is approximated by rectangular slit conduit geometry. Fluid flow through hollow fibers, dialysate feed and return tubing, blood feed and return tubing, and arterial and venous grafts is approximated by circular conduit geometry. Fluid flow through feed and return manifolds is approximated by parabolic geometry. Flow rate and pressure drop through these channel and conduit geometries are estimated by the following equations.

Blood flow in terms of pressure differential is characterized by the equation:

$$\dot{Q} = \frac{\Delta P}{R}$$

where:
$\dot{Q}$ is volumetric flow rate, $\Delta P$ is the difference in pressure, and R is flow resistance.

The change in pressure within in a rectangular channel when w>>h is calculated as:

$$\Delta P = \frac{12\mu L \dot{Q}}{h^3 w}$$

where:
$\Delta P$ is the difference in pressure, $\dot{Q}$ is the volumetric flow rate, h is channel height, w is channel width, L is channel length, and $\mu$ is fluid viscosity.

For a circular channel, pressure differential is calculated as:

$$\Delta P = \frac{8\mu L \dot{Q}}{\pi r^4}$$

where:
$\Delta P$ is the difference in pressure, $\dot{Q}$ is the volumetric flow rate, r is channel radius, L is channel length, and $\mu$ is fluid viscosity.

For a parabolic channel, pressure differential is calculated as:

$$\Delta P = \frac{105\mu L \dot{Q}}{4wh^3}$$

where:
$\Delta P$ is the difference in pressure, $\dot{Q}$ is the volumetric flow rate, h is channel height, w is channel width, L is channel length, and $\mu$ is fluid viscosity.

For purposes of estimating pressure drops throughout the device, blood flow is assumed to have a very small Reynolds number, and is thus characterized by Stokes-type fluid flow. Blood viscosity is assumed to be 0.003 Pa·s. The pressure drop calculated is assumed to be the pressure drop across all system components, with no contribution from connectors.

Table 1 shows the estimated pressure drop to drive blood flow at 500 mL/min through components having various geometries. The total pressure drop indicated in the last line of the table is the sum of all individual pressure drops.

TABLE 1

| Blood conduits | Geometry | ID (cm) | OD or large dimension (cm) | Length (cm) | Pressure drop (Pa) | Pressure drop (mmHg) |
|---|---|---|---|---|---|---|
| Connection between artery and graft | circular | 0.5 | | 3 | 48.89 | 0.37 |
| Feed graft, in | circular | 0.5 | | 20 | 325.95 | 2.45 |
| Feed-port, entry | circular | 0.5 | | 5 | 81.49 | 0.61 |
| Manifold, distribution | parabola | 0.5 | 1 | 12 | 63.00 | 0.47 |
| Filter gap | slit | 0.05 | 2.5 | 6 | 169.41 | 1.27 |
| Filter thickness | cm | 0.10 | | | | |
| Total filter pack length | rectangular | 10.2 | | | | |
| Total number of filter | 68 | | | | | |
| Manifold, collection | parabola | 0.5 | 1 | 12 | 63.00 | 0.47 |
| Feed-port, exit | circular | 0.5 | | 5 | 81.49 | 0.61 |
| Graft, exit | circular | 0.5 | | 20 | 325.95 | 2.45 |
| Connection between vein and graft | circular | 0.5 | | 3 | 48.89 | 0.37 |
| total pressure drop needed for driving blood flow at 500 mL/min | | | | | 1208.07 | 9.06 |

Operating pressure may thus be calculated from the above equations, for a given blood flow rate and filter arrangement. Accordingly, a filter pack composed of stacked membranes is estimated to operate at a pressure lesser than that of a filter pack composed of packed hollow fibers to achieve a given flow rate. Table 2 shows the differences in operating pressures to drive blood flow at various flow rates.

TABLE 2

| Blood Flow Rate (mL/min) | Stacked Membrane Pressure Required (mmHg) | Hollow Fiber Bundle Pressure Required (mmHg) |
|---|---|---|
| 500 | 9.06 | 276 |
| 400 | 7.25 | 220 |
| 200 | 3.63 | 110 |
| 100 | 1.81 | 55 |

Filtration rate plays a significant role in the efficacy of hemofiltration within the system. The system is designed to achieve a rate of filtration that is at least similar to that of existing hemofiltration treatment known within the art. The rate of filtration is generally characterized by the equation:

$$\dot{Q}_f = \frac{\Delta P}{R}$$

where:

$\dot{Q}_f$ is filtration rate (filtrate volumetric flow rate), $\Delta P$ is the difference in pressure, and R is filtration resistance.

Filtration rate, $\dot{Q}_f$, is also given as:

$$\dot{Q}_f = AF\Delta P$$

where:

A is filter area, F is the hydraulic permeability, and $\Delta P$ is the difference in pressure.

Filtration performance may thus be compared across a range of operating parameters, given hydraulic permeability, membrane area, and blood pressure. Table 3 shows filtration performance as a function of hydraulic permeability, filter area, and pressure drop.

TABLE 3

| Hydraulic Permeability mL/(cm² min mmHg) | Membrane Area cm² | Blood Pressure mmHg | Filtration Rate mL/min |
|---|---|---|---|
| 0.0001 | 1000 | 60 | 5.1 |
| 0.0002 | 1000 | 60 | 10 |
| 0.0001 | 2000 | 60 | 10 |
| 0.0001 | 1000 | 300 | 30 |
| 0.0006 | 1000 | 60 | 28 |

It is assumed that blood filtration treatment should remove a volume of liquid equivalent to 3 to 5% of the patient's body weight daily. This can be achieved with a filtration rate of about 4 to 7 mL/min over the course of 8 hours. Table 3 indicates that this filtration rate is achievable at average patient blood pressure over 1000 cm² of filter media having a hydraulic permeability of 0.0001 mL/min·cm2·mmHg.

Dialysis rate plays a significant role in the efficacy of hemodialysis within the system. To operate effectively, the system should achieve a rate of dialysis similar to that of existing hemodialysis treatment.

The rate of dialysis is generally characterized by the equation:

$$\dot{Q}_d = \frac{\nabla C}{R_d}$$

where:

$\dot{Q}_d$ is diffusion flux (dialysis rate), $\nabla C$ is concentration gradient,
and $R_d$ is diffusion resistance.

Diffusion flux, $\dot{Q}_d$, is also given as:

$$\dot{Q}_d = d_{pore} A \frac{D}{t} \nabla C$$

where:

$d_{pore}$ is pore fraction, A is membrane area, D is diffusivity, t is membrane thickness, and $\nabla C$ is concentration gradient.

As shown by the equation, dialysis rate is dependent on concentration gradient and diffusive permeability. Compounding these terms yields a mass transfer coefficient, M. The equation for diffusion flux may thus be expressed as:

$$\dot{Q}_d = AM\nabla C$$

The total filter area is assumed to be 1000 cm². Concentration gradient is estimated by assuming the concentration of a given component within the dialysate. For reference, Table 4 shows the components and compositions of normal blood and urine.

TABLE 4

| Component: | Normal Blood Level (mg/ml): | Normal Urine Level (mg/ml)[E]: | Removal Rate (mg/min)[A]: | Removal Rate (g/day): | Theoretical Ultrafiltration Rate Required (ml/min)[B]: | Theoretical Dialysate Required (L/day)[C]: |
|---|---|---|---|---|---|---|
| Water | | | 1050 | 1500 | 1 | |
| $Na^+$ | 3.20 | 3.00 | 3.15 | 4.5 | 1 | 1 |
| $K^+$ | 0.20 | 1.50 | 1.58 | 2.3 | 8 | 11 |
| $Ca^{2+}$ | 0.10 | 0.15 | 0.16 | 0.2 | 2 | 2 |
| $Mg^{2+}$ | 0.03 | 0.10 | 0.11 | 0.2 | 4 | 5 |
| $Cl^-$ | 3.70 | 6.00 | 6.30 | 9.1 | 2 | 2 |
| $HCO3^-$ | 1.65 | ? | | | | |
| $Lactate^-$ | 0.11 | ? | | | | |
| $HPO4^{2-}$ | 0.03 | 1.20 | 1.26 | 1.8 | 42 | 60 |
| $Urate^-$ | 0.02 | 0.30 | 0.32 | 0.5 | 16 | 23 |
| $SO4^{2-}$ | 0.03 | 1.80 | 1.89 | 2.7 | 63 | 91 |
| $NH4^+$ | 0.002 | 0.20 | 0.21 | 0.3 | 105 | 151 |
| Glucose | 1.00 | 0.00 | 0.00 | 0.0 | 0 | 0 |
| Urea | 0.30 | 18.00 | 19.00 | 27.4 | 63 | 91 |
| Creatinine | 0.01 | 1.00 | 1.05 | 1.5 | 105 | 151 |
| β-2-μglobulin[D] | 0.002 | 0.16 | 0.17 | 0.2 | 85 | 122 |

[A] calculated from urine flow of 1.05 ml/min and average urine compositon
[B] calculated from removal rate and normal blood concentration assuming sieve coef. of 1 and no reabsorption
[C] calculated from removal rate and blood concentration assuming ideal dialysis membrane ($V_D = V_F(C_1/C_0 - 1)$)
[D] Nissenson et al, "Continuously functioning artificial nephron system", Hemodialysis Int., vol. 9, 2005.
[E] Encyclopedia Britannica Online Components of interest in hemodialysis include urea, creatinine, and NaCl. Concentration of these components within a patient's blood is typically used by physicians to determine dialysis and filtration treatment schedules and dosing prescriptions. Specifically, the concentration of creatinine within a patient's blood may be used as a glomerulus filtration rate surrogate. Creatinine and urea concentrations can be used to estimate system performance and patient residual kidney function. Table 5 shows the estimated time needed per day to remove the daily buildup of various blood components based on, a linear approximation.

TABLE 5

| Membrane area cm² | Urea | | | | Creatinine | | | | NaCl | | | |
|---|---|---|---|---|---|---|---|---|---|---|---|---|
| | Mass transfer coefficient cm/s | Blood concentration (mM) | Daily build-up (g/day) | Dialysis time needed Hour/day | Mass transfer coefficient cm/s | Blood concentration (mM) | Daily build-up (g/day) | Dialysis time needed Hour/day | Mass transfer coefficient cm/s | Blood concentration (mM) | Daily build-up (g/day) | Dialysis time needed Hour/day |
| 1000 Commercial cellulose | $1 \times 10^3$ | 10 | 10 | 5 | $0.5 \times 10^3$ | 0.3 | 1.5 | 24 | $0.75 \times 10^3$ | 142 | 3 | 4 |
| 1000 MEMS (1% porosity) | $0.9 \times 10^3$ | 10 | 10 | 5 | $0.65 \times 10^3$ | 0.3 | 1.5 | 18 | $0.75 \times 10^3$ | 142 | 3 | 4 |
| 2000 Commercial cellulose | $1 \times 10^3$ | 10 | 10 | 3 | $0.5 \times 10^3$ | 0.3 | 1.5 | 12 | $0.75 \times 10^3$ | 142 | 3 | 2 |

Based on information derived from the forgoing data, the stacked membrane arrangement is estimated to effectively operate using parameters that are conducive to daily nocturnal hemodialysis, with blood flow driven by pressure comparable to that of a patient's average blood pressure.

Implantable ultrafiltration and hemodialysis membranes have been developed, such as those described in U.S. Pat. App. Pub. 2009/0131858, Fissell et al. ("Fissell"), the subject matter of which is incorporated herein by reference. Nanoporous membranes suitable for ultrafiltration and hemodialysis and operable at a pressure of 30 mmHg having a hydraulic permeability dependent on membrane pore size are contemplated by the invention. Membranes having pores of dimensions 500 microns or less in length and 500 nanometers or less in width, with length to width ratios of at least 2:1 can also be used in the invention. A membrane conforming to these parameters has been constructed and yielded an albumin sieve coefficient of 0.24, and can be used optionally in the invention.

FIG. 13 shows the difference between co-current and counter-current flow types by comparison of diagrams (a) and (b). FIG. 13(a) shows the simplified flow diagram through n stacked membrane filters of FIG. 12. FIG. 13(b) shows a simplified flow diagram for counter-current, flow though n stacked membrane filters similar to FIG. 12.

Figure 14:
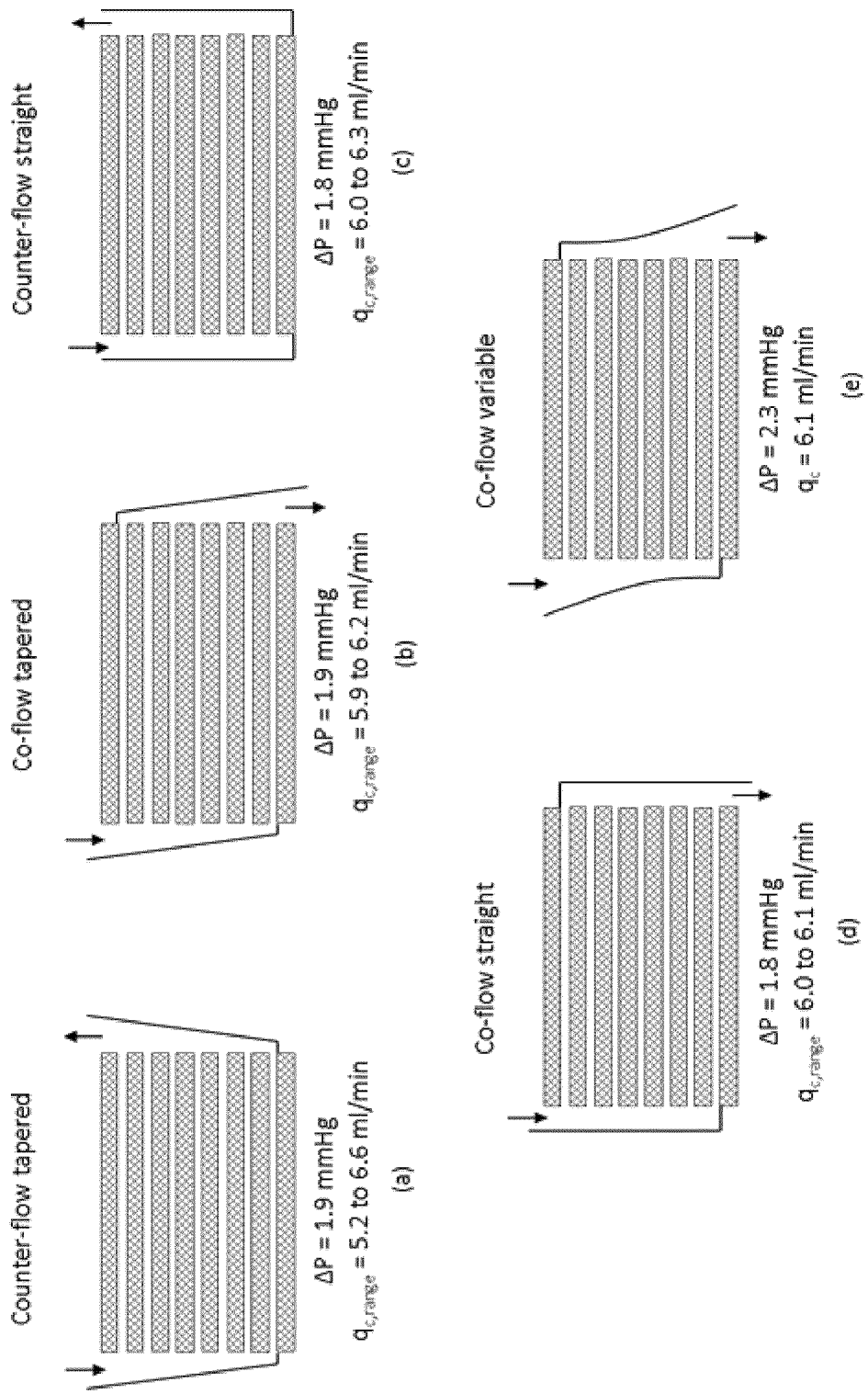
FIG. 14 shows illustrations of flow configurations through a stacked membrane filter having stacked membranes.

Simplified fluid flow diagrams through 66 stacked membranes are shown in FIG. 14. The configurations shown are combinations of co-current or counter-current flows through filter packs having feed and return manifolds with various cross-sectional areas or geometries. The flow paths within the manifolds are defined by the shape and cross-sectional geometry or area of the manifolds. Counter-current flow of blood and dialysate can maintain a large concentration gradient between the two fluids by exposing solute-deficient dialysate to solute-rich blood in all membrane channels. In certain embodiments, diffusive mass transfer relies upon concentration gradient as a driving force, thus counter-current flow is advantageous, however, other embodiments not solely relying on diffusive mass transfer are contemplated and hence, other flow configurations may be advantageous. FIG. 14(a) shows a counter-current flow configuration having tapered feed and return manifolds. FIG. 14(b) shows a co-current flow configuration having tapered feed and return manifolds. FIG. 14(c) shows a counter-current flow configuration having straight feed and return manifolds. FIG. 14(d) shows, a co-current flow configuration having straight feed and return manifolds. FIG. 14(e) shows a co-current flow configuration having feed and return manifolds with variable cross-sectional areas or geometries. In one embodiment, the implantable device of the invention can have a linearly tapered configuration in either a counter-flow or co-flow arrangement as described in FIGS. 14(a) and (b). In another embodiment, the implantable device of the invention can have a straight flow configuration in either a counter-flow or co-flow arrangement as described in FIGS. 14(c) and (d). In still another embodiment, the implantable device of the invention can have a variably shaped flow configuration in either a co-flow arrangement as described in FIG. 14(e) or a counter-flow arrangement (not shown). Calculations of the total pressure drop, ΔP, through the membrane stack, and the range of flow rates, $q_{c,range}$, through the membrane channels are indicated for each configuration. In one non-limiting example, the calculations assume a feed flow of about 200 mL/min, and a fluid feed pressure of about 100 mmHg. The non-limiting calculations further assume 33 membranes channels spaced about 0.483 mm apart, and fluid flow through feed and return manifolds having a D-shaped or semicircular cross section with a largest dimension of about 0.551 cm. Where the feed and return manifolds are tapered; they are assumed in this non-limiting example to have a semi-circular cross section of width $D_i$, at membrane channel i according to the equation:

$$D_i = 0.073923(1.573 - 1.573i) + 5.506 \text{ mm}$$

where:

$$D_1 = 5.506 \text{ mm and } D_{33} = 1.785 \text{ mm}$$

Similar calculations can be performed by those of ordinary skill in the art to obtain different dimensions and values as desired.

Figure 15:
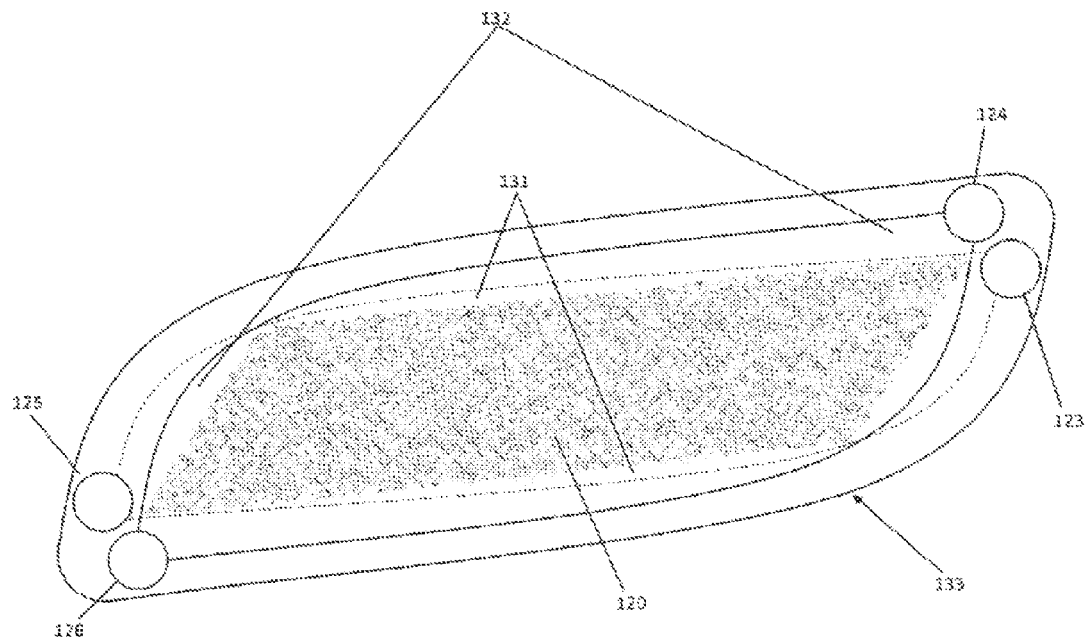
FIG. 15 is a top view of an embodiment of a curved membrane filter element.

Features for one embodiment of a curved membrane filter element 133 for use in a curved implantable module are shown in FIG. 15. The curved implantable module includes a plurality of curved membrane filter elements 133 stacked within said curved implantable module. When stacked, curved membrane filter elements 133 form some of the internal features of the curved implantable module. A blood feed manifold of the curved implantable module can be formed by a plurality of stacked blood feed manifold sections 124. A blood return manifold of the curved implantable module can be formed by a plurality of stacked blood return manifold sections 126. A dialysate feed manifold of the curved implantable module can be formed by a plurality of stacked dialysate feed manifold sections 125. A dialysate return manifold of the curved implantable module can be formed by a plurality of stacked dialysate return manifold sections 123. A blood membrane channel 132 forms a blood flow path on a first side of a membrane having two sides, and a dialysate membrane channel 131 forms a dialysate flow path on a second side of said membrane. The area of overlap of blood membrane channel 132 and dialysate membrane channel 131 forms an active membrane area 120 across which mass transfer occurs between blood and dialysate.

Figure 16:
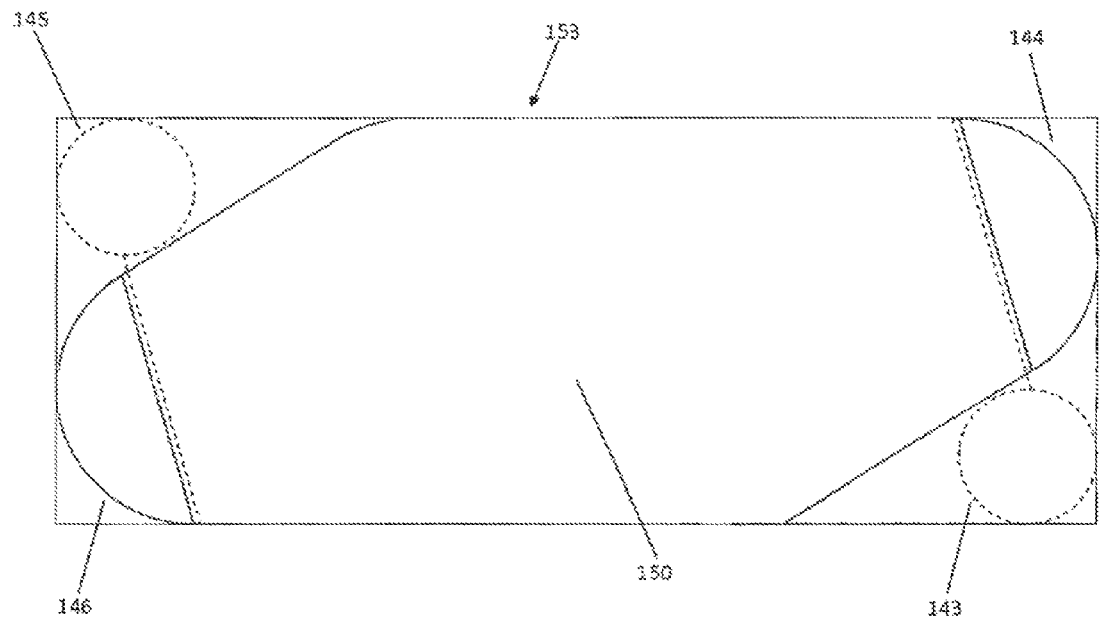
FIG. 16 is a top view of another embodiment of a membrane filter element.

Referring to FIG. 16, another embodiment of a membrane filter element 153 is shown having semicircular blood feed manifold section 144 and semicircular blood return manifold section 146. A blood membrane channel forms a blood flow path on a first side of membrane 150, and a dialysate membrane channel forms a dialysate flow path on a second side of said membrane 150. An area of overlap of a blood membrane channel and a dialysate membrane channel forms an active membrane area across which mass transfer occurs between blood and dialysate.

Figure 17:
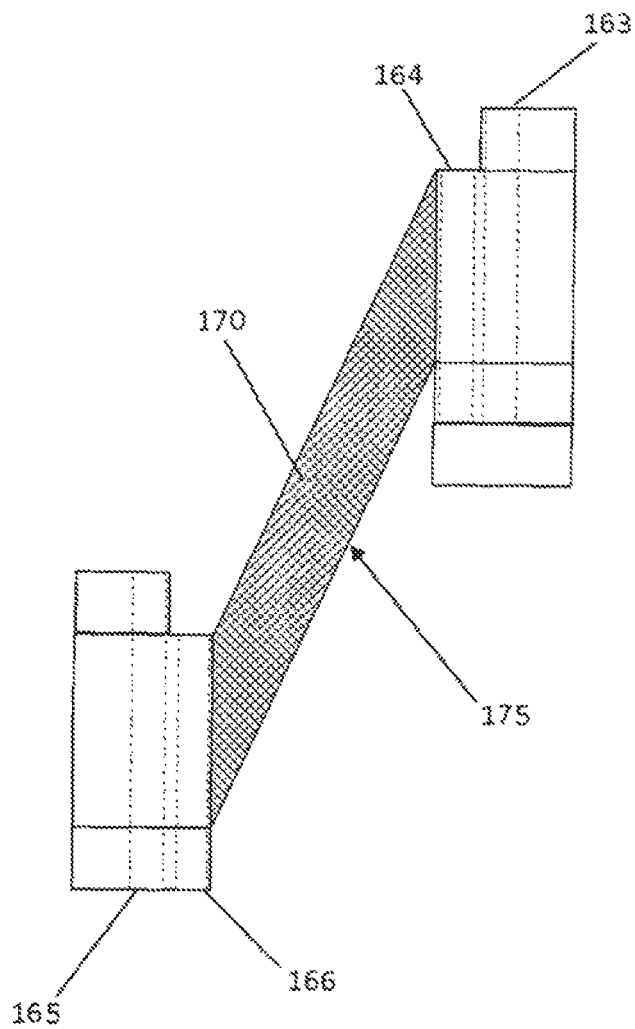
FIG. 17 is a side view of an angled membrane filter element.

An angled embodiment of membrane filter element 65 as shown in FIG. 10 is illustrated in FIG. 17. Angled membrane filter element 175 includes membrane 170; blood feed manifold section 164, blood return manifold section 166, dialysate feed manifold section 165, and dialysate return manifold section 163.

Figure 18:
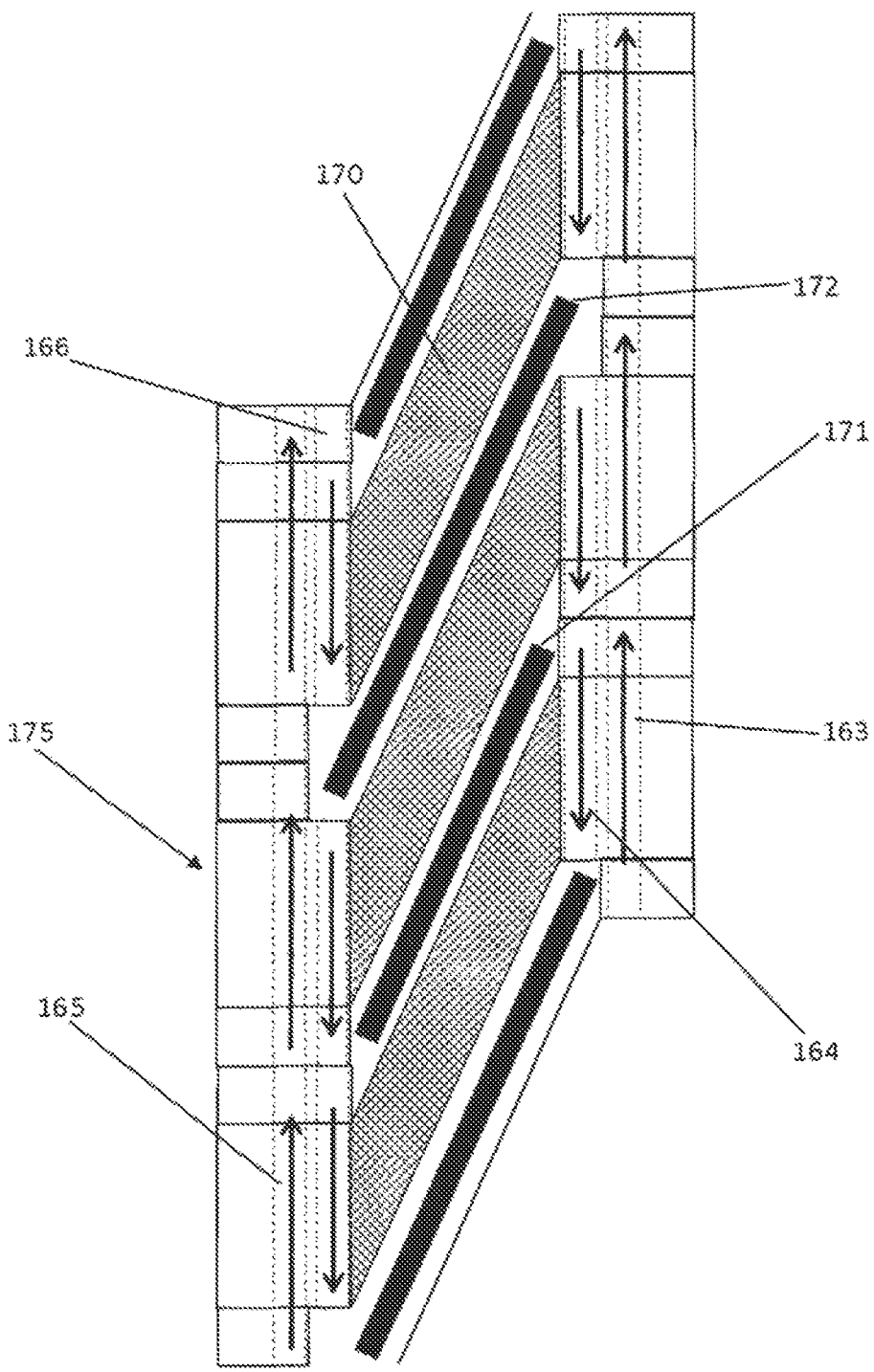
FIG. 18 is a side view of a membrane stack composed of a stack of angled membrane filter elements from FIG. 17.

FIG. 18 shows a plurality of stacked angled membrane filter elements 175. A blood feed manifold is formed by a plurality of stacked blood feed manifold sections 164. A blood return manifold is formed by a plurality of stacked blood return manifold sections 166. A dialysate feed manifold is formed by a plurality of stacked dialysate feed manifold sections 165. A dialysate return manifold is formed by a plurality of stacked dialysate return manifold sections 163.

Additional shapes and orientations of membrane filter elements are contemplated by the invention. Furthermore, the shapes and orientations of membrane filter elements need not be consistent, and the shape and orientation of an individual filter element may be varied relative to an adjacent element. Similarly, the implantable module housing may also vary in shape. The housing shape can be formed in any symmetrical or asymmetrical shape suitable for implantation within a patient, and can be contoured to include any combination of undulations and curves. The housing can be shaped independently of the membrane filter elements therein, or the housing can be shaped to accommodate the shapes and orientations of membrane filter elements. One skilled in the art will recognize that by using different shapes and orientations of filter elements and module housings, an implantable module tailored to ergonomically fit the anatomy of a patient may be obtained.

Figure 19:
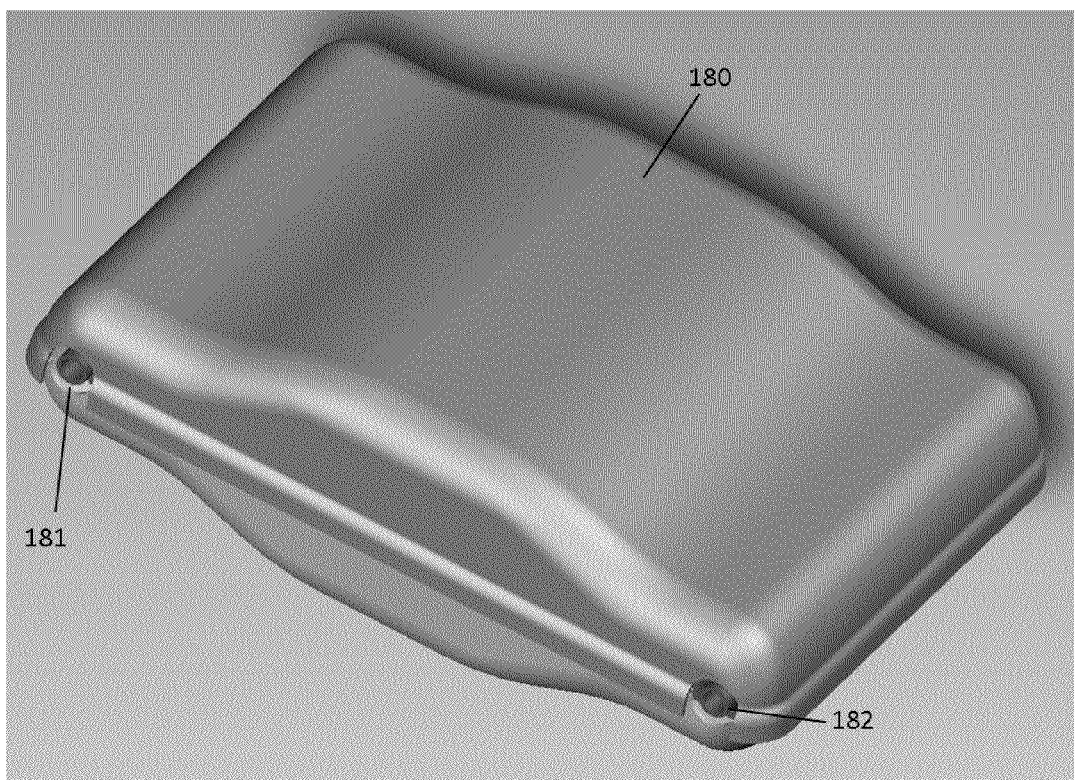
FIG. 19 is a perspective view of an implantable module embodiment with a casing.

Referring to FIG. 19, external features of a one non-limiting embodiment of an implantable module are shown. Internal features of the implantable module can be encased by casing 180. Casing 180 allows for protrusion of a blood inlet, 181 and a blood outlet 182. Not visible in the view of FIG. 19 are a dialysate inlet and a dialysate outlet. The implantable module of FIG. 19 is shown without casing 180 in FIG. 20. A dialysate inlet 183 and a dialysate outlet 184 are shown in addition to blood inlet 181 and blood outlet 182. A location for a membrane stack 200 within the implantable module is indicated. A location for a components space 185 within the implantable module is indicated.

Figure 20:
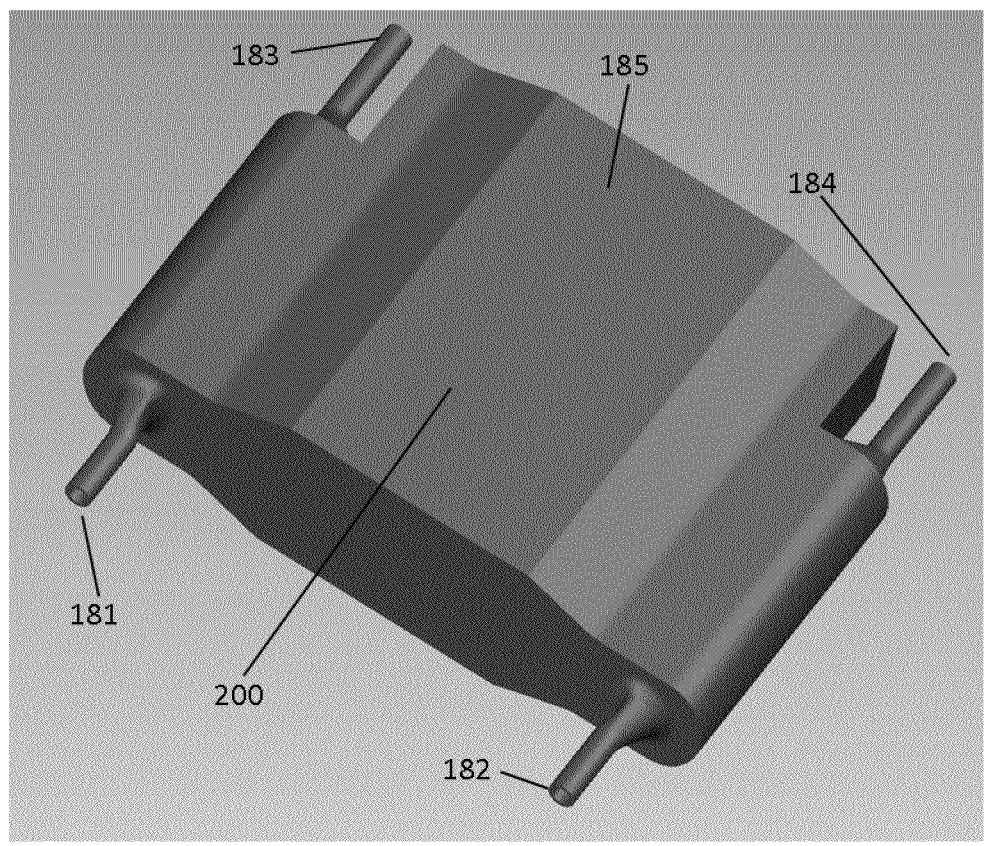
FIG. 20 is a perspective view of the implantable module embodiment of FIG. 19 without a casing.
Figure 21:
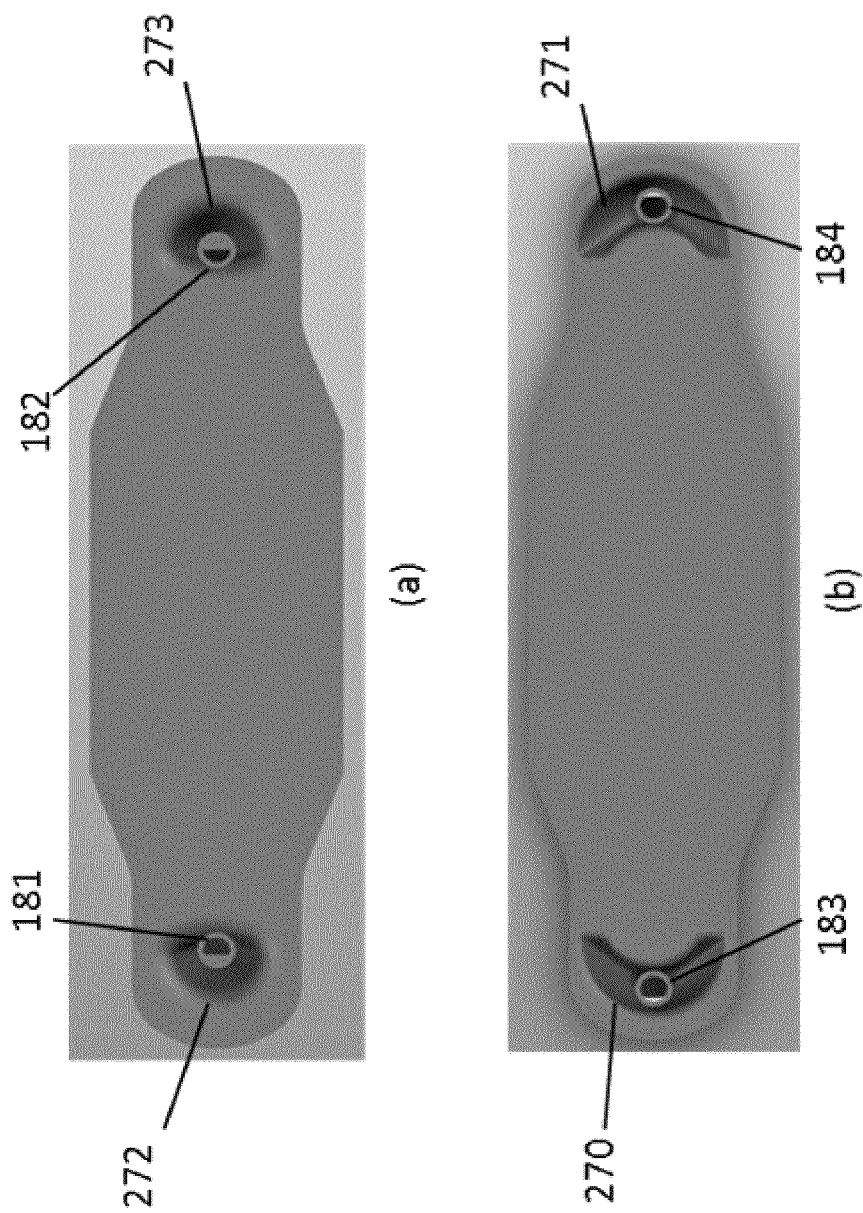
FIG. 21 shows inlets and outlets of the implantable module embodiment of FIG. 20.

In one version, a top side of the implantable module of FIG. 20 is shown in FIG. 21(a). A bottom side of the implantable module of FIG. 20 is shown in FIG. 21(b). As shown in FIG. 21, blood inlet 181 and blood outlet 182 each have a circular cross section. As also shown in FIG. 21, dialysate inlet 183 and dialysate outlet 184 each have a circular cross section. Other cross-sections such as semicircular, rectangular, rhombus, trapezoidal, oval, ellipsoidal, and triangular are contemplated, and are contemplated by the invention without any limitation to shape. The cross-sectional geometries, of each of a blood feed manifold 272, a blood return manifold 273, a dialysate feed manifold 270, and a dialysate return manifold 271 are also shown, and can also have any of the cross-sectional geometries such as semicircular, rectangular, rhombus, trapezoidal, oval, ellipsoidal, and triangular. The geometries of the manifolds are shaped to minimize the volume of the implantable module. The cross-sectional geometry of the blood feed manifold 272 and the blood return manifold 273 can form a D-channel or be shaped as semicircle. The cross-sectional geometry of the dialysate feed manifold 270 and the dialysate return manifold 271 can be U-shaped. In certain embodiments, the cross-sectional geometries of each inlet and outlet transition to and from the manifold to which they are attached as shown in FIG. 21.

Figure 22:
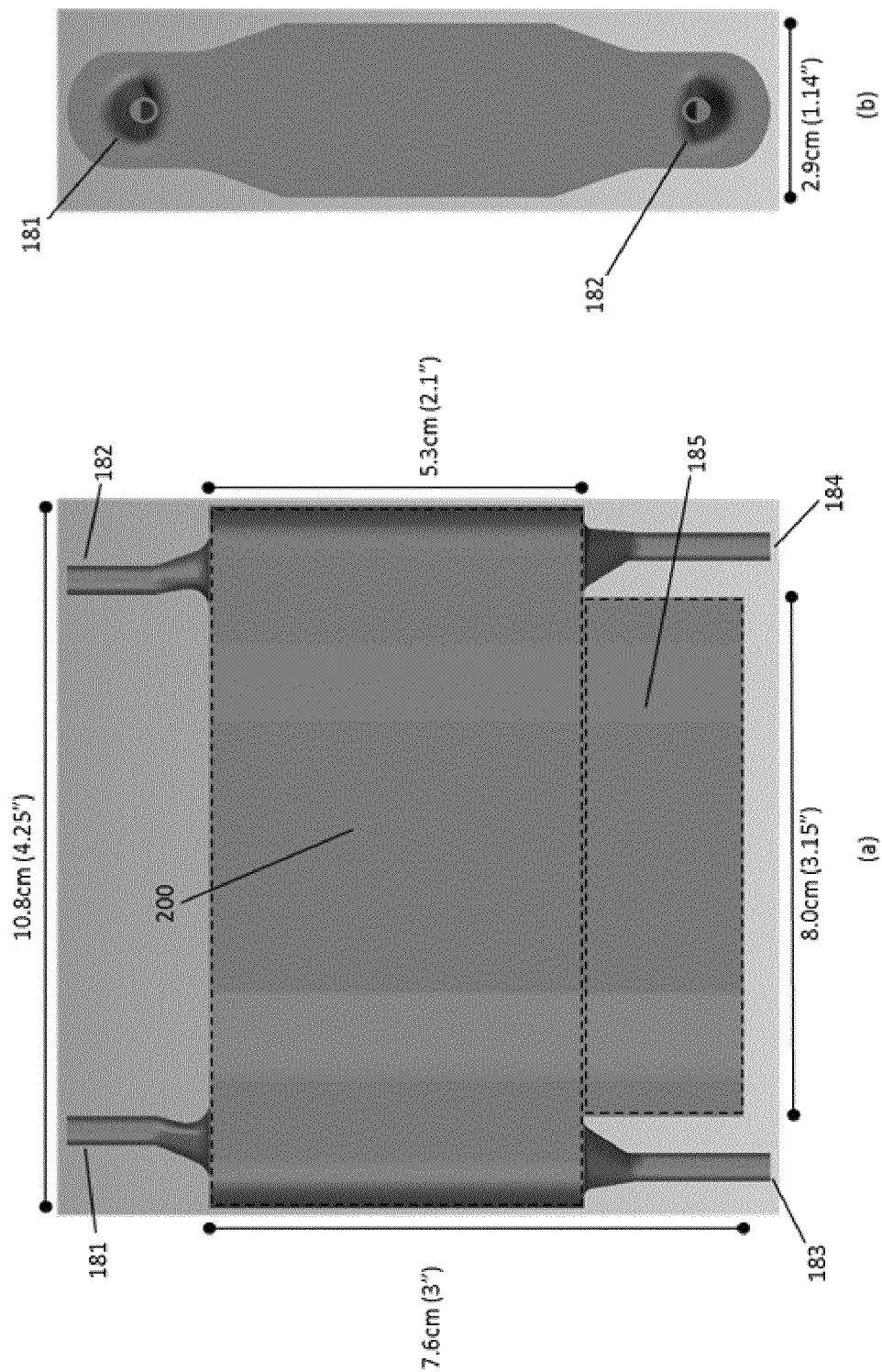
FIG. 22 shows dimensions of the implantable module embodiment of FIG. 20.

Non-limiting examples of possible dimensions of the implantable module of FIG. 20 are shown in FIG. 22. The implantable module has a total volume of approximately about 240 mL. Dashed lines indicate the locations of membrane stack 200 and components space 185. The space for one embodiment of the membrane stack 200 has an approximate volume of 166 mL and the components space 185 has an approximate volume of 53 mL. It is understood that the implantable device can be designed to have varying volumes as desired.

Figure 23:
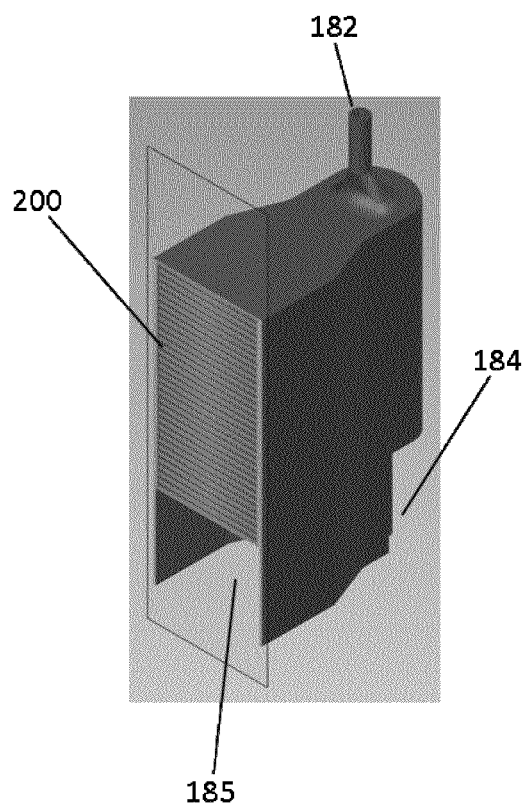
FIG. 23 is a sectional perspective view showing a membrane stack of the implantable module embodiment of FIG. 20.
Figure 24:
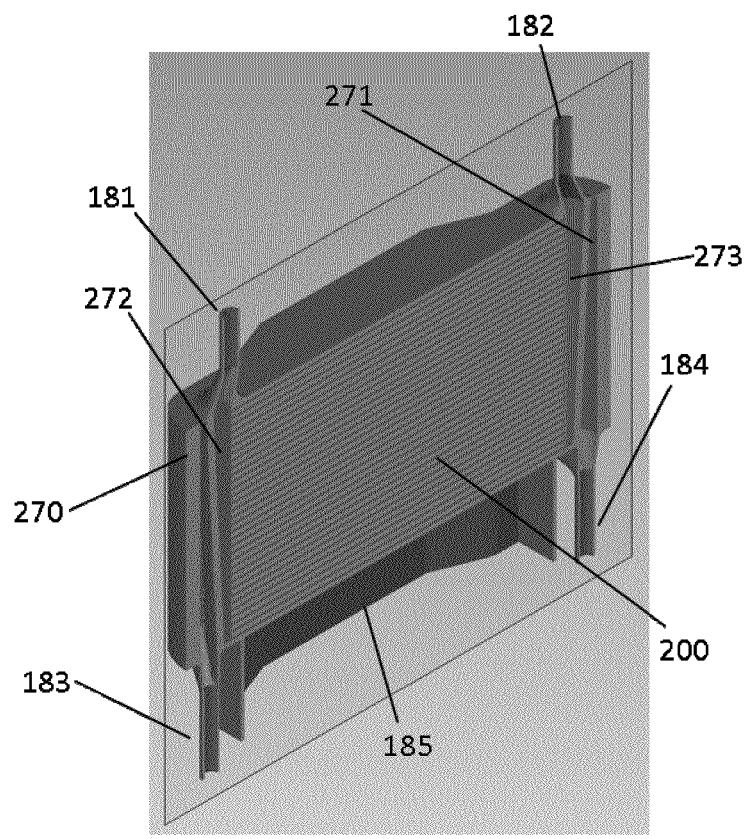
FIG. 24 is another sectional perspective view showing feed and return manifolds and the membrane stack of the implantable module embodiment of FIG. 20.

One non-limiting cross section of the implantable module of FIG. 20 is shown in FIG. 23, wherein the arrangement of membrane stack 200 and components space 185 is shown. Another cross section of the implantable module of FIG. 20 is shown in FIG. 24, wherein the arrangement of membrane stack 200, components space 185, blood feed manifold 272, blood return manifold 273, dialysate feed manifold 270, and dialysate return manifold 271 are shown. In both of FIGS. 23 and 24, a simplified view of individual membrane filter elements is viewable in membrane stack 200.

Figure 25:
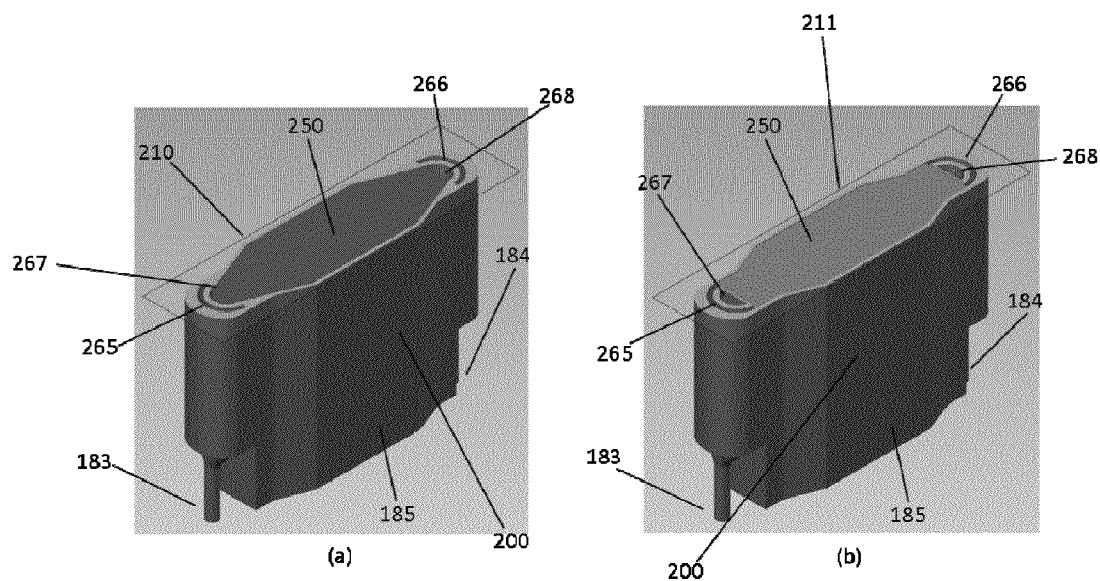
FIG. 25 shows additional sectional views of the implantable module embodiment of FIG. 20.

Additional cross sections of a non-limiting embodiment of the implantable module are shown in FIG. 25. FIG. 25(a) is a cross-sectional view of the implantable module revealing a blood membrane channel 210 on a first side of a membrane 250 in membrane stack 200. Blood within blood membrane channel 210 flows from a blood feed manifold section 267, across a membrane 250 in membrane stack 200, and into a blood return manifold section 268. FIG. 25(b) is a cross-sectional view of the implantable module revealing a dialysate membrane channel 211 on a second side of a membrane 250 in membrane stack 200. Dialysate within dialysate membrane channel 211 flows from a dialysate feed manifold section 265, across a membrane 250 in membrane stack 200, and into a dialysate return manifold section 266.

Figure 26:
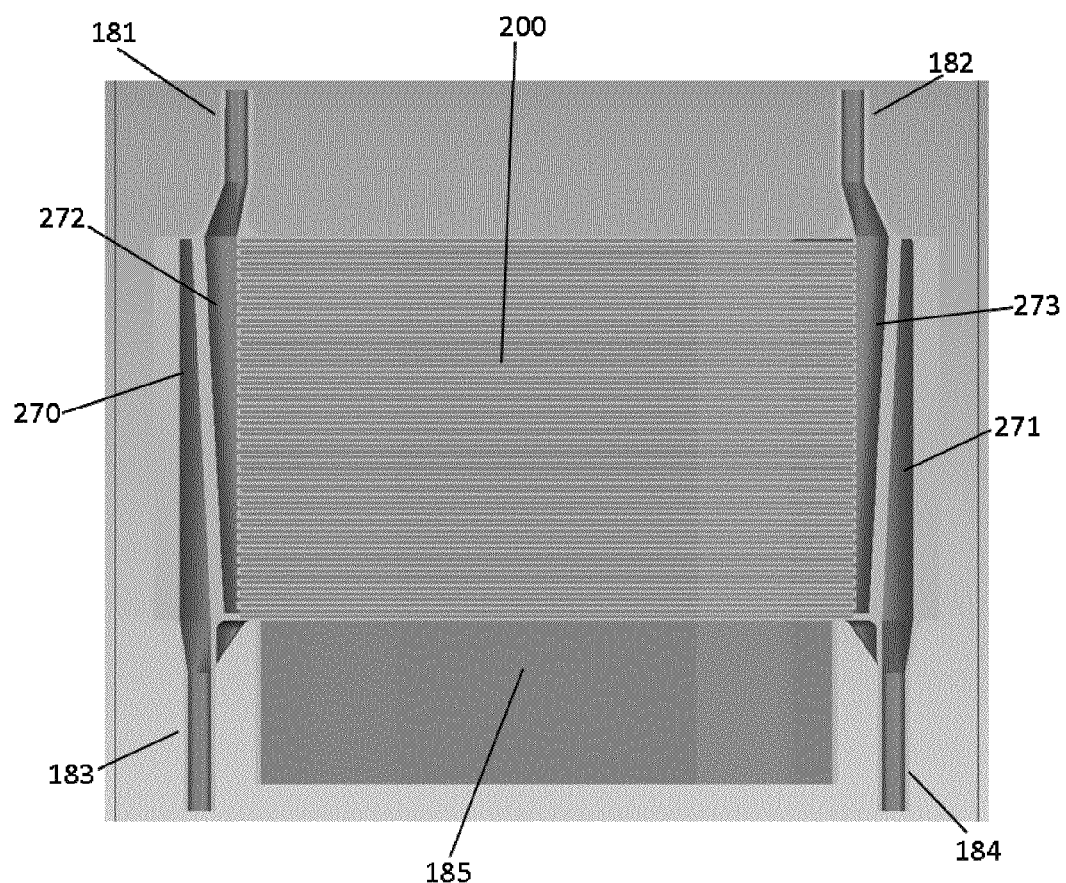
FIG. 26 is a sectional front view showing the manifolds and membrane stack of the implantable module embodiment of FIG. 20.

Referring to FIG. 26, one possible cross-sectional view of the implantable module is shown. The feed and return manifolds in this embodiment are tapered to maintain uniform flow velocity through the membrane channels in the membrane stack 200. The blood feed manifold 272 linearly or non-linearly tapers from wide to narrow in the direction of flow into the implantable module, and the blood return manifold 273 linearly or non-linearly tapers from narrow to wide in the direction of flow out of the implantable module. In other embodiments, the area of the cross-section of the blood manifold decreases in the direction of flow into the membrane stack and the area of the cross-section of the dialysate manifold increases in the direction of flow out of the implantable module in the first manifold assembly. In still other embodiments, the area of the cross-section of the dialysate manifold decreases in the direction of flow into the membrane stack and the area of the cross-section of the blood manifold increases in the direction of flow out of the implantable module in the second manifold assembly. The tapering can be linear or non-linear. In other embodiments, the manifolds are not tapered. The manifolds may have a cross-sectional geometry that is constant. Additionally, the manifolds may have a cross-sectional geometry that is variable. The dialysate feed manifold 270 linearly or non-linearly tapers from wide to narrow in the direction of flow into the implantable module, and the dialysate return manifold 271 linearly or non-linearly tapers from narrow to wide in the direction of flow out of the implantable module.

Referring further to embodiments having a stacked membrane filter pack, a plurality of feed and return manifold configurations are contemplated. In addition to having various cross-sectional shapes, the cross-sectional area of feed and return manifolds along the length of the membrane stack may be constant, variable, linearly tapered, or non-linearly tapered. Furthermore, independent of manifold cross-sectional geometry and area, the direction of flow throughout the manifolds, and therefore the membrane stack, may be arranged to provide co-current or counter-current flows of dialysate relative to blood.

An example of a non-limiting embodiment includes a manifold configuration in which the cross-sectional area of the feed manifolds of both blood and dialysate linearly tapers from wide to narrow in the direction of flow into the implantable module, and the cross-sectional area of the return manifolds of both blood and dialysate linearly tapers from narrow to wide in the direction of flow out of the implantable module. Another example includes a manifold configuration in which the cross-sectional area of the feed manifolds of both blood and dialysate non-linearly tapers from wide to narrow in the direction of flow into the implantable module, and the cross-sectional area of the return manifolds of both blood and dialysate non-linearly tapers from narrow to wide in the direction of flow, out of the implantable module. Further, the linearity or non-linearity of manifold tapering, need not be consistent across each manifold. For example, the tapering of a feed manifold may be defined by a first linear or non-linear equation while the tapering of the corresponding return manifold, or any other manifold, may be defined by a second linear or non-linear equation.

Another example of a non-limiting embodiment includes a manifold configuration in which the cross-sectional area of the feed manifolds of both blood and dialysate is variable throughout the direction of flow into the implantable module, and the cross-sectional area of the return manifolds of both blood and dialysate is variable throughout the direction of flow out, of the implantable module. The variability of manifold cross-sectional area need not be consistent across each manifold.

Yet another example of a non-limiting embodiment includes a manifold configuration in which the cross-sectional area of the feed and return manifolds of both blood and dialysate is constant resulting in straight manifolds.

Additionally, other embodiments contemplate any combination of the types of manifolds described. For example, a manifold pair can have a configuration different from the other wherein each can be variable, tapered, or straight. Another embodiment may include linearly tapered dialysate feed and return manifolds with variable blood feed and return manifolds. Another embodiment may include a linearly tapered dialysate feed manifold, a non-linearly tapered dialysate return manifold, a constant blood, feed manifold, and a variable blood return manifold. Yet another embodiment may include a variable dialysate feed manifold, a straight dialysate return manifold, a blood feed manifold tapered according to a first linear equation, and a blood return manifold tapered according, to a second linear equation. All permutations of manifold configurations are contemplated.

One skilled in the art will recognize that different types of flow within a given manifold configuration embodiment may be obtained by changing the fluid inlet and outlet connections to the implantable module. The roles of a feed and return manifold pair may be switched by changing the feed and return tubing connections to the implantable module. For example, in an embodiment where a dialysate feed manifold is tapered from wide to narrow in the direction of flow into the implantable module, and the corresponding dialysate return manifold is tapered from narrow to wide in the direction of flow out of the implantable module, the connections to the inlet and outlet of the implantable module may be switched to obtain a dialysate feed manifold that is tapered from narrow to wide in the direction of flow into the implantable module, with the corresponding dialysate return manifold tapered from wide to narrow in the direction of flow out of the implantable module. One skilled in the art will further appreciate that switching the inlet and outlet connections of dialysate without switching the inlet and outlet connections of blood will change the flow of dialysate relative to blood. Similarly, the flow of blood relative to dialysate may be changed by switching the inlet and outlet connections of blood without switching the inlet and outlet connections of dialysate. One skilled in the art will further recognize that any permutation and combination of the described manifold and flow configurations may be employed to obtain desired flow, dialysis, and ultrafiltration profiles.

Figure 27:
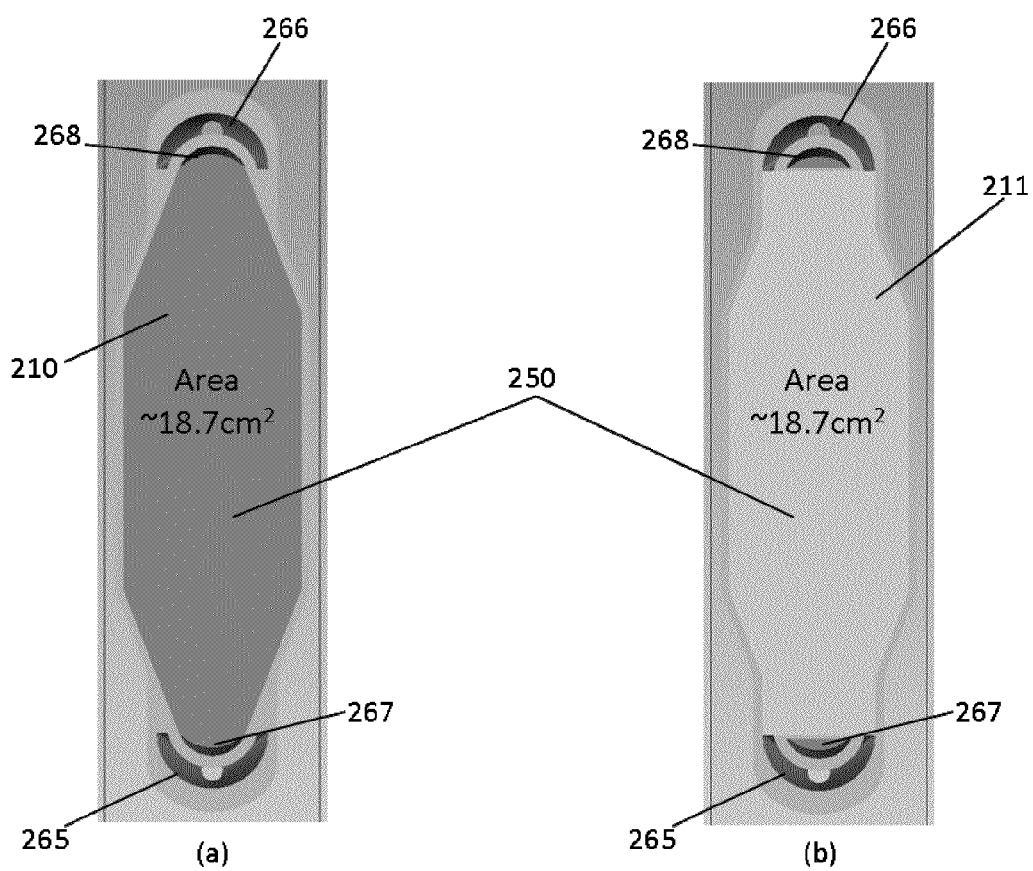
FIG. 27 shows top views of the channels of the implantable module embodiment of FIG. 20.

FIG. 27 indicates an area of surface interface with a membrane 250 of both a blood membrane channel 210 and a dialysate membrane channel 211 of the implantable module. In this embodiment, the surface interface area of a blood membrane channel 210 with a membrane 250 can be about 18.7 cm$^2$. The surface interface area of a dialysate membrane channel 211 with a membrane 250 can also be about 18.7 cm$^2$.

Figure 28:
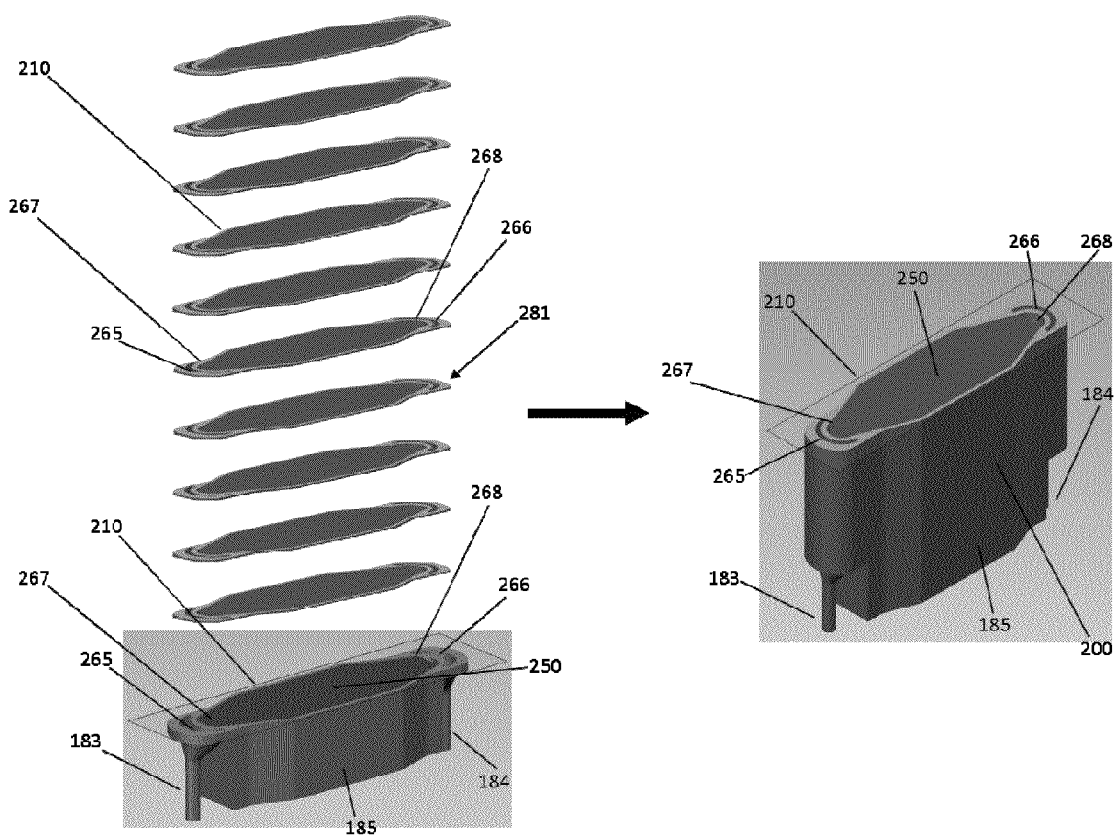
FIG. 28 shows a method of manufacture of the implantable module embodiment of FIG. 20. An exploded view of the parts of the implantable module embodiment is shown transitioning to a sectional perspective view of the constructed implantable module embodiment.

One non-limiting method of manufacture of the implantable module of FIG. 20 is simplified into a two-step illustration shown in FIG. 28. Individually machined membrane filter elements 281 incorporate a membrane 250, a blood feed manifold section 267, a blood return manifold section 268, a dialysate feed manifold section 265, and a dialysate return manifold section 266. A plurality of individually machined membrane filter elements 281 are stacked and fixed together. The membrane filter elements 281 may be welded; glued, bonded, or clamped together by means known to those of skill in the art. Alternatively, casing 180 shown in FIG. 19 may be used to hold the membrane filter elements 281 together. Each membrane filter element 281 is individually machined to create the tapered manifolds shown in FIG. 26, thus the size of the manifold sections for each element can be unique.

Figure 29:
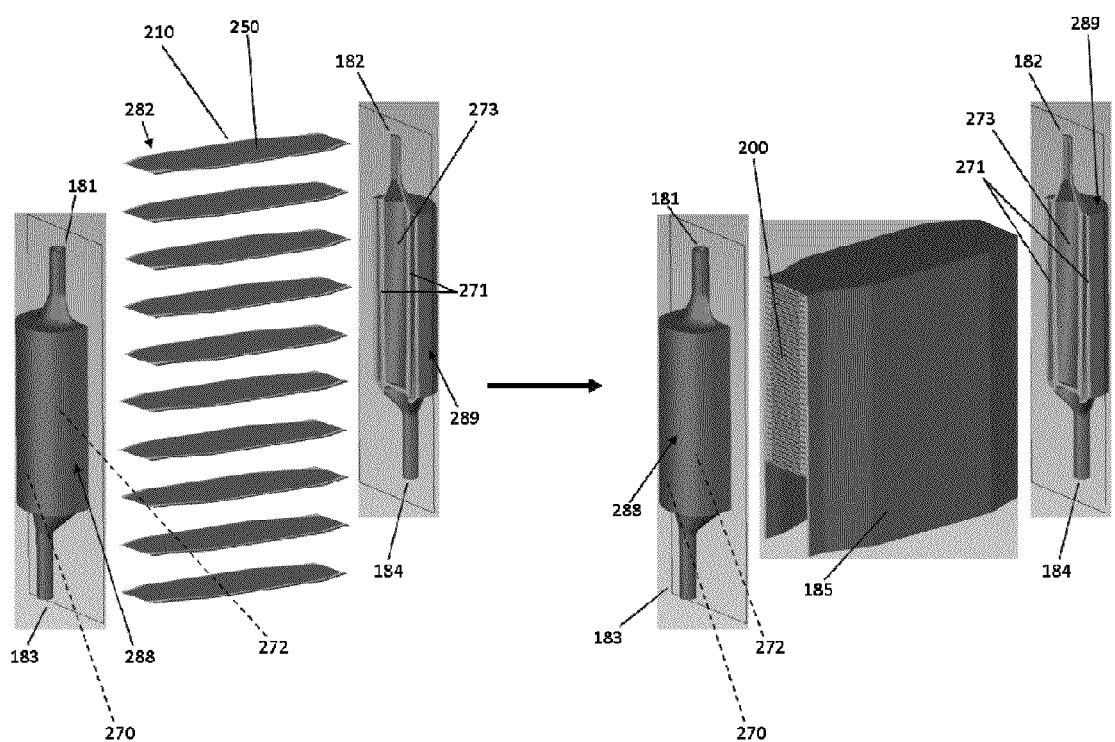
FIG. 29 shows another method of manufacture of the implantable module embodiment of FIG. 20. An exploded view of the parts of the implantable module embodiment is shown transitioning to a partially-exploded perspective view of the constructed implantable module embodiment.

One non-limiting method of manufacture of the implantable module is simplified into a two-step illustration shown in FIG. 29. Identical membrane filter elements 282 incorporate a membrane 250. A manifold assembly A 288 incorporates blood inlet 181, dialysate inlet 183, blood feed manifold 272, and dialysate feed-manifold 270. A manifold assembly B 289 incorporates blood outlet 182, dialysate outlet 184, blood return manifold 273, and dialysate return manifold 271. A plurality of identical membrane filter elements 282 are stacked and fixed together for form membrane stack 200. The membrane filter elements 282 may be welded, glued, bonded, or clamped together by any suitable means known to those of skill in the art. Manifold assembly A 288 is fixed to a first side of membrane stack 200 as shown in FIG. 29. Manifold assembly B 289 is fixed to a second side of membrane stack 200 as shown in FIG. 29. The manifold assemblies A and B, 288 and 289 may be welded, bonded, or clamped to membrane stack 200. Alternatively, casing 180 shown in FIG. 19 may be used to hold membrane stack 200, manifold assembly A 288, and manifold assembly B 289 together.

Figure 30:
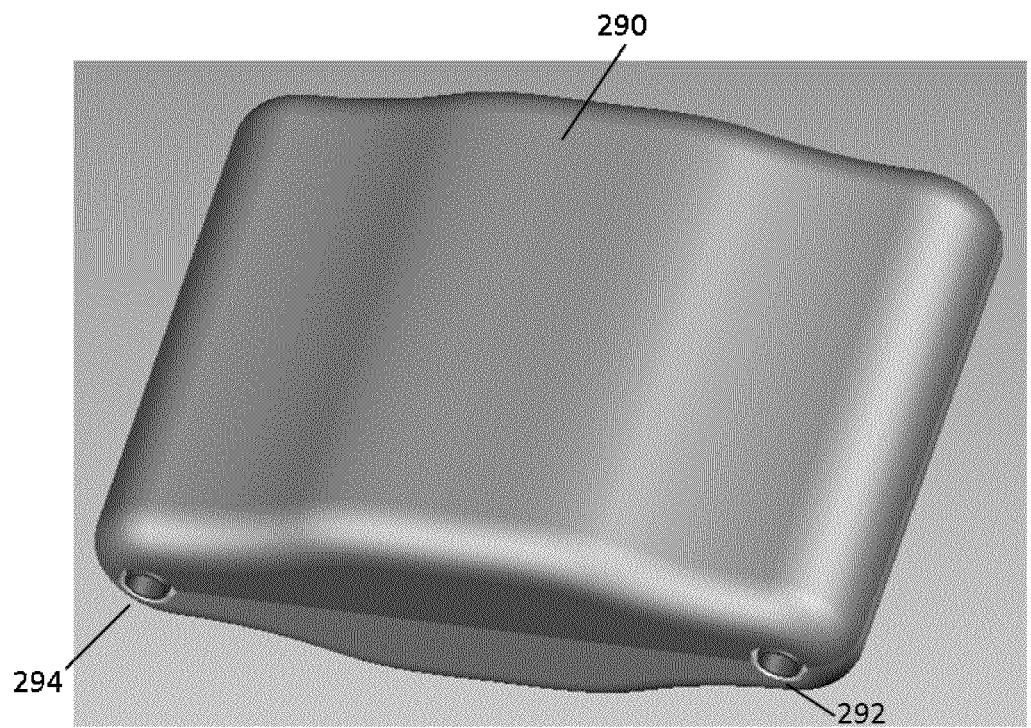
FIG. 30 is a perspective view of another implantable module embodiment with a casing.
Figure 31:
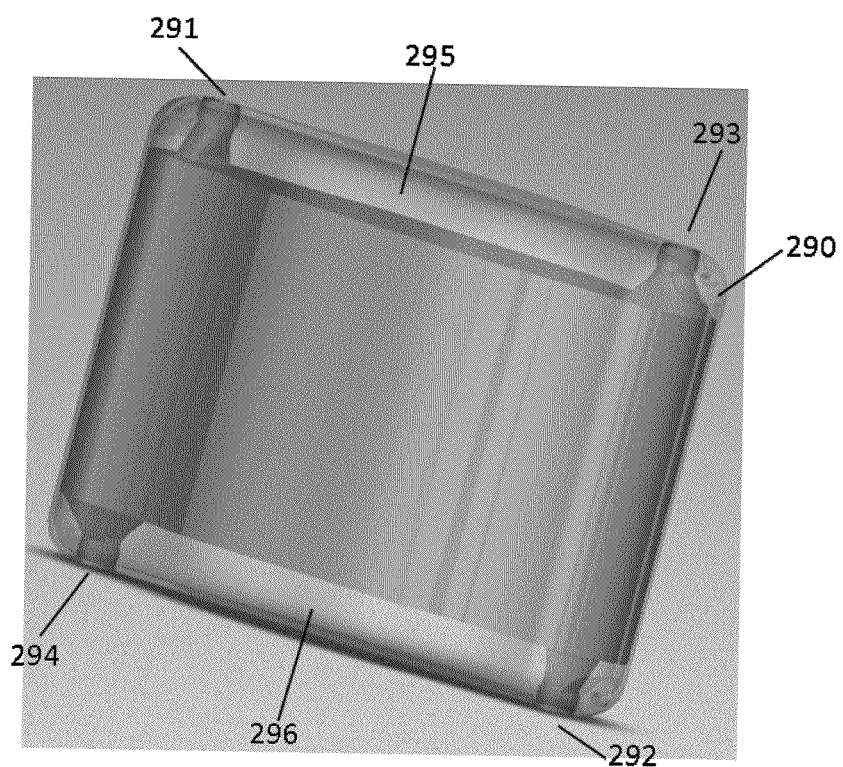
FIG. 31 is a partially-transparent perspective view of the implantable module embodiment of FIG. 30.
Figure 32:
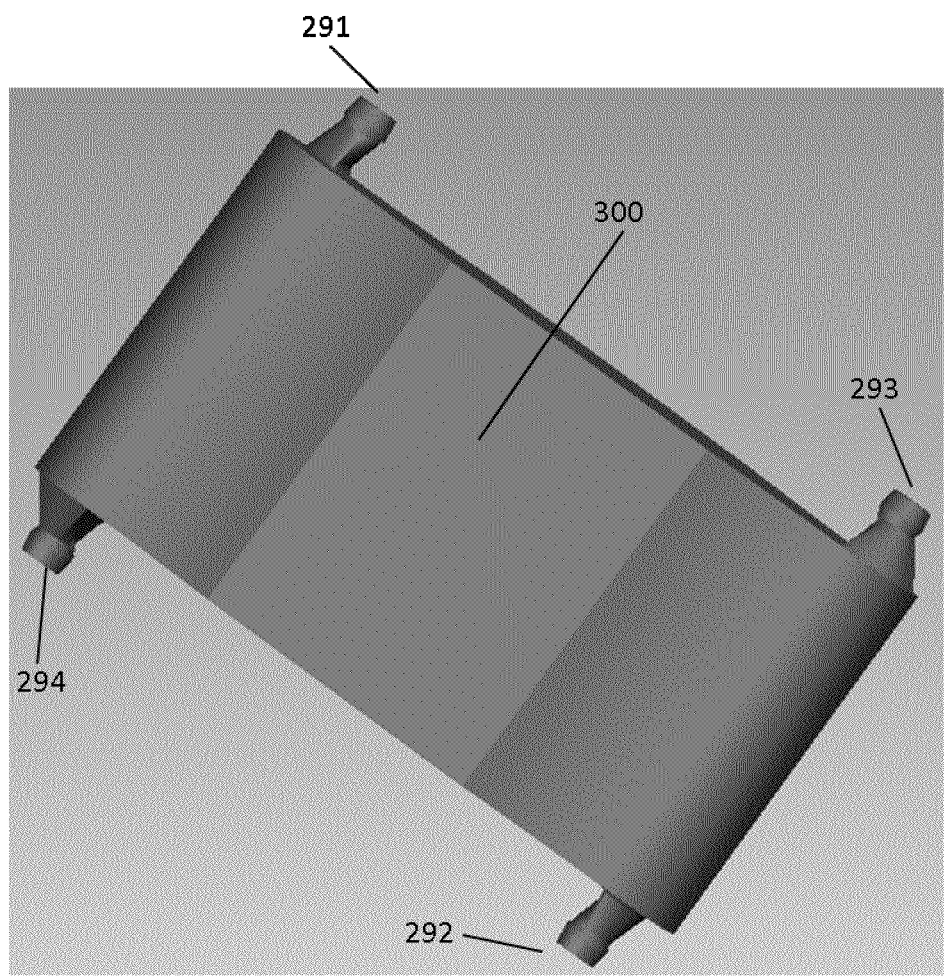
FIG. 32 is a perspective view of the implantable module embodiment of FIGS. 30 and 31 without a casing.

Referring to FIG. 30, external features of another embodiment of an implantable module are shown. Internal features of the implantable module are encased by casing 290. Casing 290 allows for protrusion of a blood outlet, 292 and a dialysate outlet 294. Not visible in the view of FIG. 30 area blood inlet and a dialysate inlet. FIG. 31 shows a transparent view of casing 290 revealing a blood inlet 291, a dialysate inlet 293, a first location for components space A 295, and a second location for components space B 296. In another version, the implantable module is shown without casing 290 in FIG. 32. A location for a membrane stack 300 within the implantable module is indicated in addition to blood inlet 291, blood outlet 292, dialysate inlet 293, and dialysate outlet 294.

Figure 33:
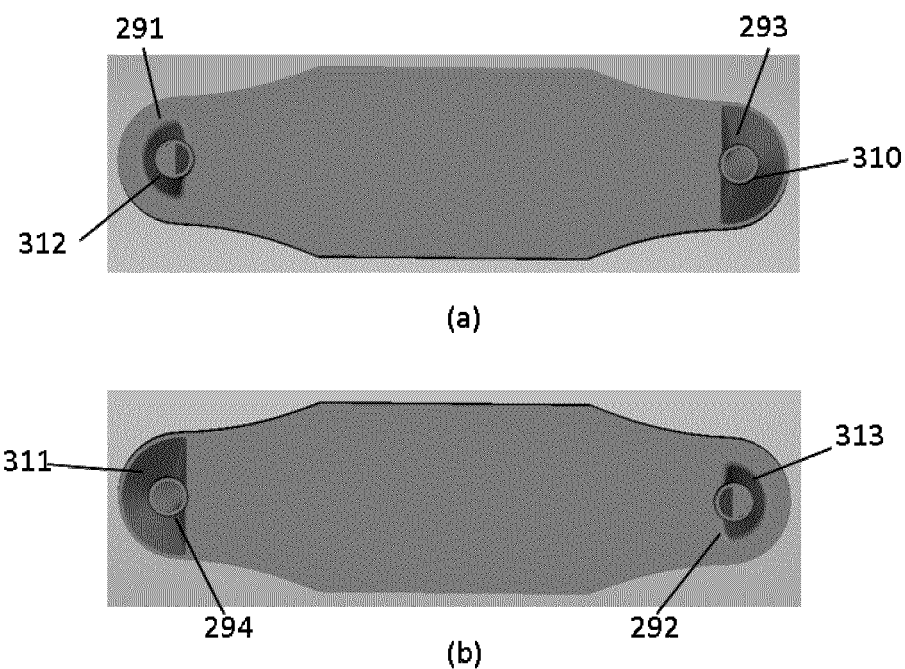
FIG. 33 shows inlets and outlets of the implantable module embodiment of FIG. 32.

A top side of one embodiment of an implantable module is shown in FIG. 33(a). A bottom side of the implantable module is shown in FIG. 33(b). As shown in FIG. 33, blood inlet 291 and blood outlet 292 each have a circular cross section. As also shown in FIG. 33, dialysate inlet 293 and dialysate outlet 294 each have a circular cross-section. The cross-sectional geometries of each of a top-most part of the blood feed manifold 312, a bottom most part of a blood return manifold 313, a top-most part of a dialysate feed manifold 310, and a bottom most part of a dialysate return manifold 311 are shown. In certain embodiments, the cross-sectional geometry of blood feed manifold 312 and blood return manifold 313 can trace a D-shape to form a D channel, or passageway. In other embodiments, the D channel or passageway can be defined for a dialysate return or feed manifold. The blood and dialysate manifolds can also form any one of a substantially C-shape, U-shape, semicircular, rectangular, triangular or circular shape. In other embodiments, the cross-sectional geometry of the manifold may transition from a cross-section having any one of a substantially C-shape, U-shape, D-shape, semicircular, rectangular, triangular or circular shape to another different cross-sectional geometry that is a substantially C-shape, U-shape, D-shape, semicircular, rectangular, triangular or circular shape. In still other embodiments, the manifolds may linearly or non-linearly taper from a top-most to a bottom-most part or vice versa.

Figure 34:
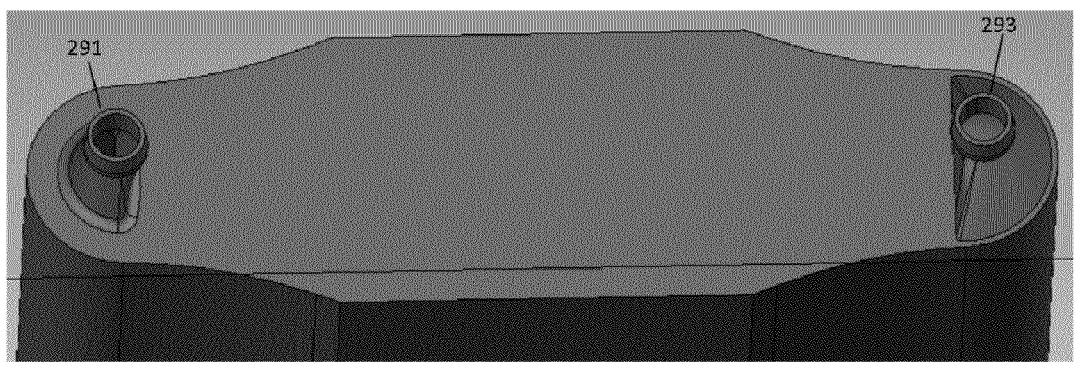
FIG. 34 shows perspective views of the top of the implantable module embodiment of FIG. 32.
Figure 34:
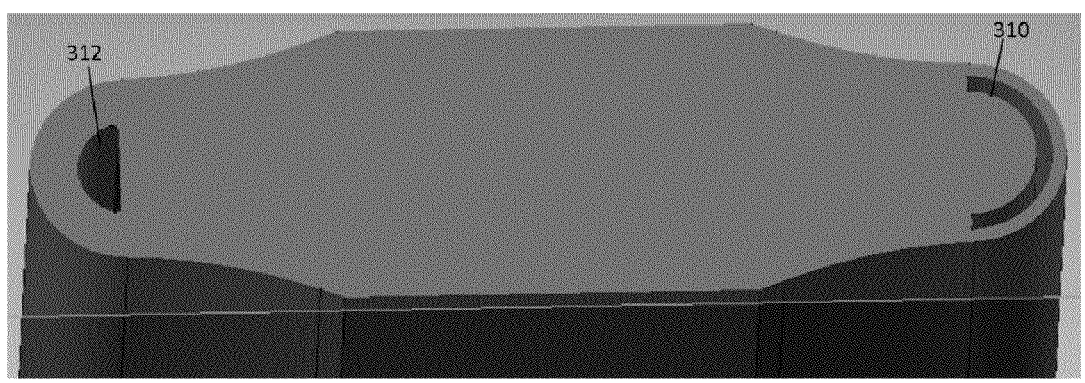

FIG. 34 shows the top side of one non-limiting embodiment of the implantable module in greater detail. FIG. 34(a) shows the top side of the implantable module with blood inlet 291 and dialysate inlet 293 attached. FIG. 34(b) shows the top side of the implantable module without blood inlet 291 and dialysate inlet 293. The transition of cross-sectional geometry from blood inlet 291 to a substantially semicircular shape blood feed manifold 312 is shown where a top-most opposite side of a blood return manifold 313 (see FIG. 35a below) is not depicted. The transition of cross-sectional geometry from dialysate inlet 293 to dialysate feed manifold 310 in a C-shape is shown where a top-most opposite side of a dialysate return manifold 311 (see FIG. 35a below) is not depicted. Where a C-shaped cross-geometry is contemplated, a U-shaped geometry can also be used depending, on the desired shape of the device or housing. Similarly, the substantially semicircular shape of blood feed manifold 312 can be adapted to fit a desired shape of the device or housing where the cross-sectional geometry of the semicircular canal can be flexed, flattened or compressed.

Figure 35:
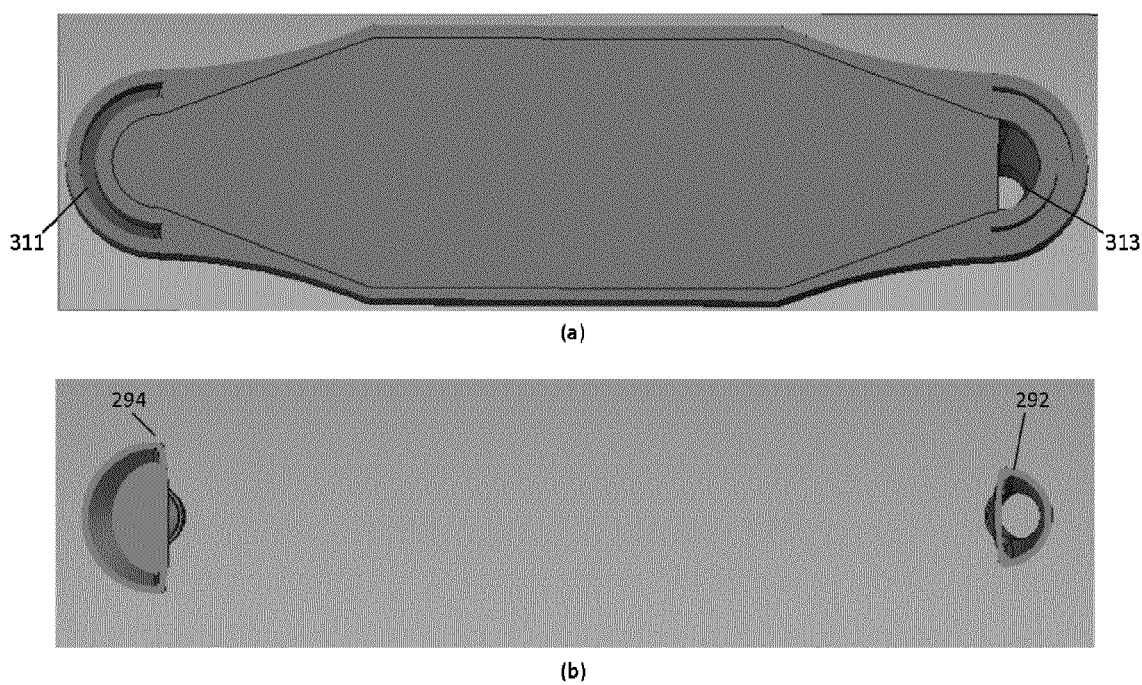
FIG. 35 shows perspective views of the bottom of the implantable module embodiment.

FIG. 35 shows the bottom side of the non-limiting implantable module in greater detail. FIG. 35(a) shows the bottom side of the implantable module without the blood outlet 292 and dialysate outlet 294 wherein the bottom-most section of the C-shaped dialysate feed manifold 310 (see FIG. 34b above) is shown as thin channel endings (not labeled). The cross-sectional geometry of blood return manifold 313 is semicircular wherein an opposite bottom-most portion of the semicircular blood feed manifold 312 (see FIG. 34b above) is depicted as a thin C-shaped canal (not labeled) wherein the blood feed manifold 312 tapers to the thin C-shaped canal from the top-most to the bottom-post part. Other embodiments include a bottom-most portion of the blood feed manifold 312, which is not tapered or transitioned to a different cross-sectional geometry, and remains a semicircular canal for the length of the manifold. Similarly, in other embodiments the bottom-most opposite ends of the dialysate feed manifold 310 can maintain a C-shape throughout the length of the manifold and not end as thin channel endings.

FIG. 35(b) shows blood outlet 292 and dialysate outlet 294 detached from the implantable module. The transition of cross-sectional geometry from a top-most part of the blood return manifold 313 (not depicted in FIG. 34a) to a bottom-most portion of the blood return manifold 313 to blood outlet 292 is shown. Similarly, the transition of cross-sectional geometry from a top-most dialysate return manifold 311 (not depicted in FIG. 34a) to a bottom-most part of the dialysate return 311 to dialysate outlet 294 is also shown.

Figure 36:
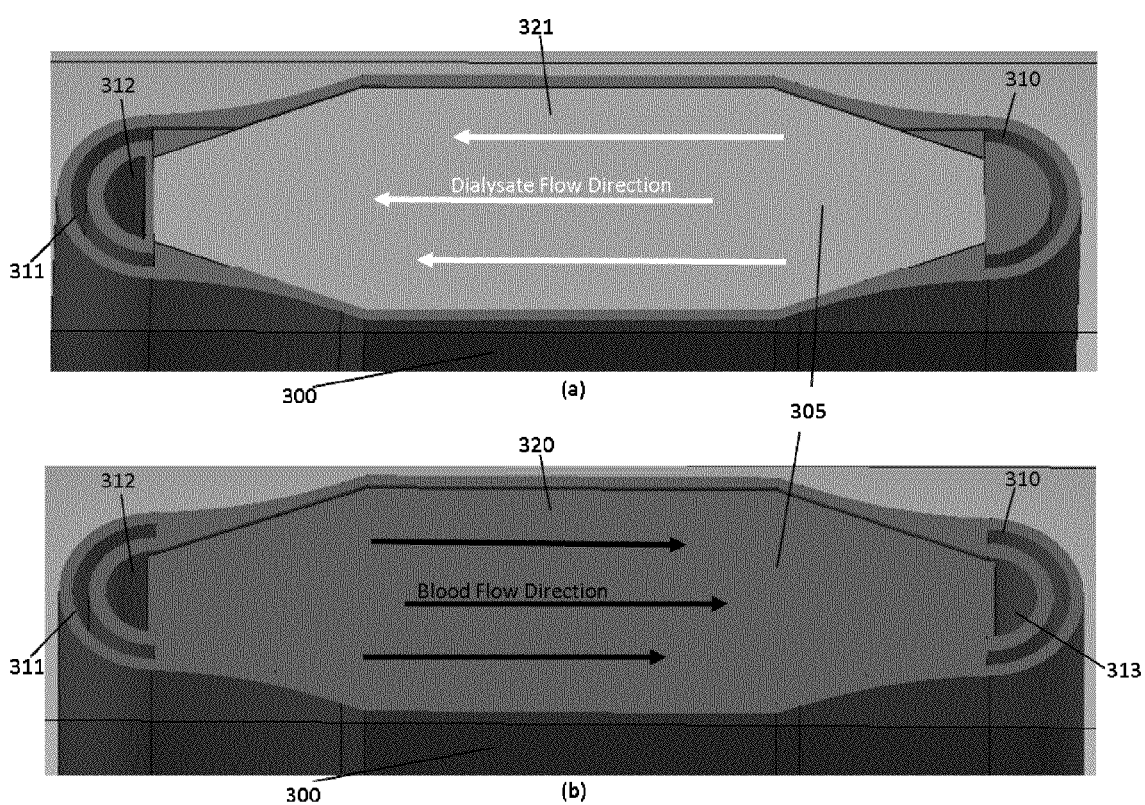
FIG. 36 shows perspective views of channels of the implantable module embodiment.

Non-limiting cross sections of the implantable module are shown in FIG. 36. FIG. 36(a) is a cross-sectional view of the implantable module revealing a dialysate membrane channel 321 on a first side of a membrane 305 in membrane stack 300. A direction of dialysate flow within dialysate membrane channel 321 is indicated flowing from dialysate feed manifold 310, across a membrane 305 in membrane stack 300, and into dialysate return manifold 311. FIG. 36(b) is a cross-sectional view of the implantable module revealing a blood membrane channel 320 on a second side of a membrane 305 in membrane stack 300. A direction of blood flow within a blood membrane channel 320 is indicated flowing from blood feed manifold 312, across a membrane 305 in membrane stack 300, and into blood return manifold 313.

Figure 37:
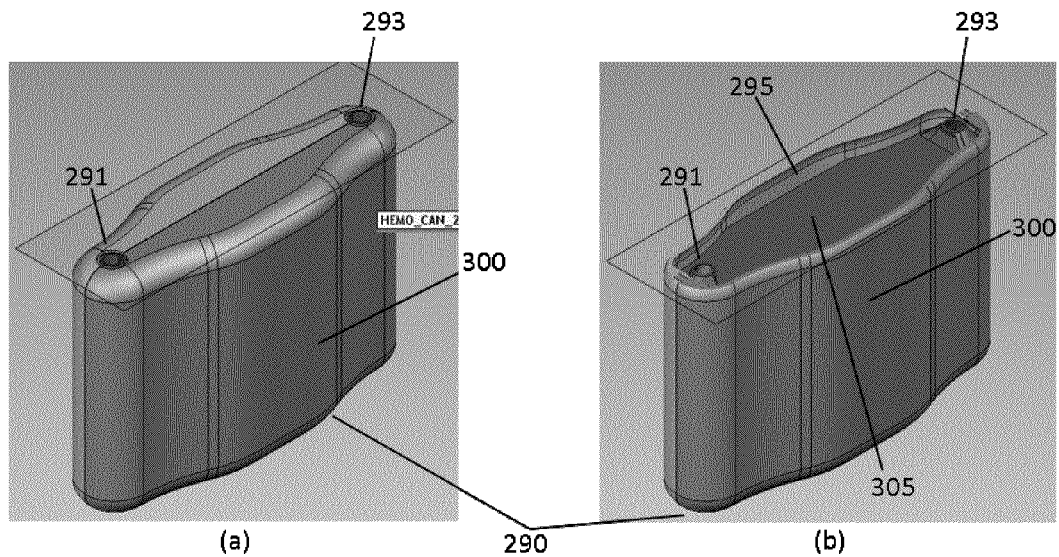
FIG. 37 shows perspective views of the front side of the implantable module embodiment.

Additional views of the implantable module are shown in FIG. 37. FIG. 37(a) shows blood inlet 291 and dialysate inlet 293 protruding from casing 290. FIG. 37(b) shows a cross section of the implantable module revealing a top side of the implantable module and the locations of components space A 295, blood inlet 291, and dialysate inlet 293 on said top side.

Figure 38:
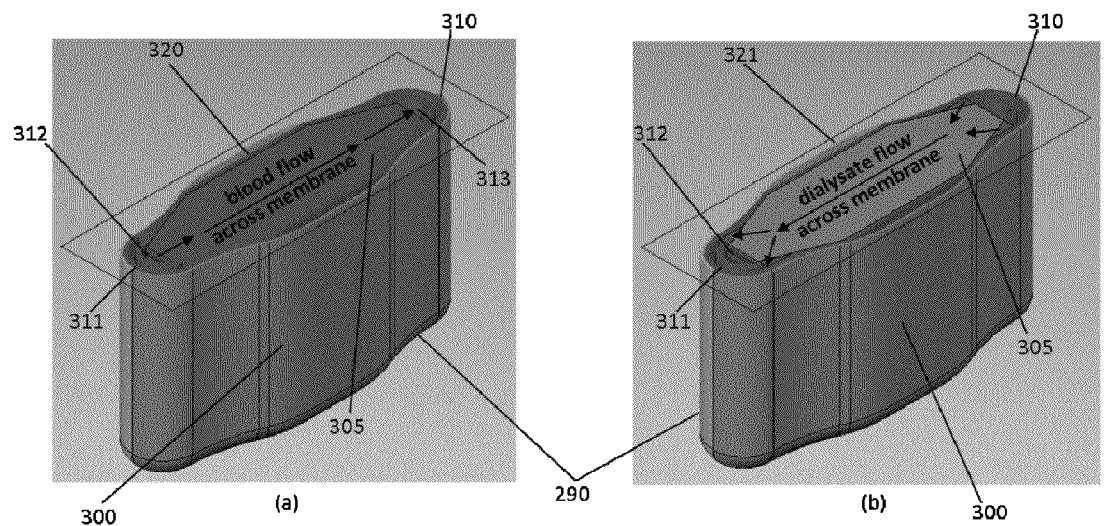
FIG. 38 shows sectional views of the implantable module embodiment.

Non-limiting cross sections of an implantable module are shown in FIG. 38. FIG. 38(a) is a cross-sectional view of the implantable module revealing a blood membrane channel 320 on a first side of a membrane 305i n membrane stack 300. A direction of blood flow within blood membrane channel 320 is indicated flowing from blood feed manifold 312, across a membrane 305 in membrane stack 300, and into blood return manifold 313. FIG. 38(b) is a cross-sectional view of the implantable module revealing a dialysate membrane channel 321 on a second side of a membrane 305 in membrane stack 300. A direction of dialysate flow within dialysate membrane channel 321 is indicated flowing from dialysate feed manifold 310, across a membrane 305 in membrane stack 300, and into dialysate return manifold 311.

Figure 39:
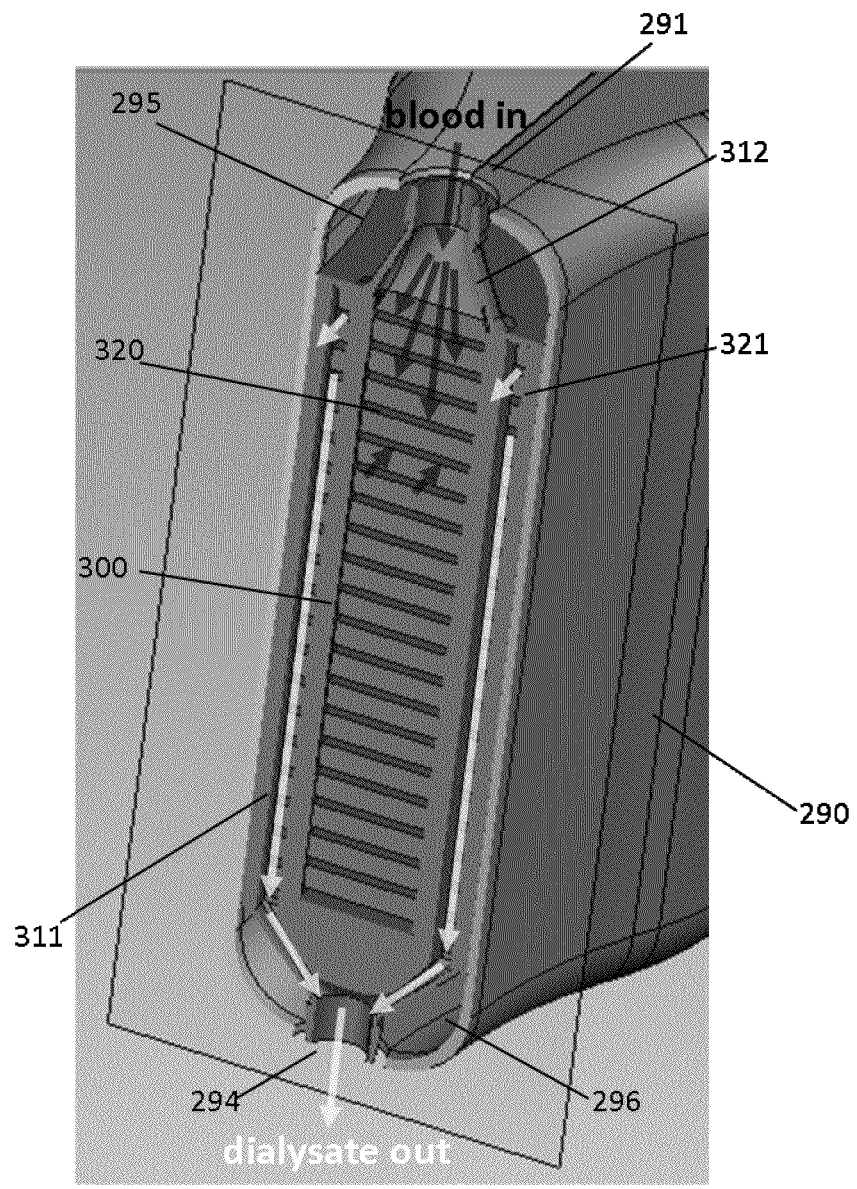
FIG. 39 is a sectional perspective view of blood and dialysate channels and manifolds within a left side of the implantable module embodiment.
Figure 40:
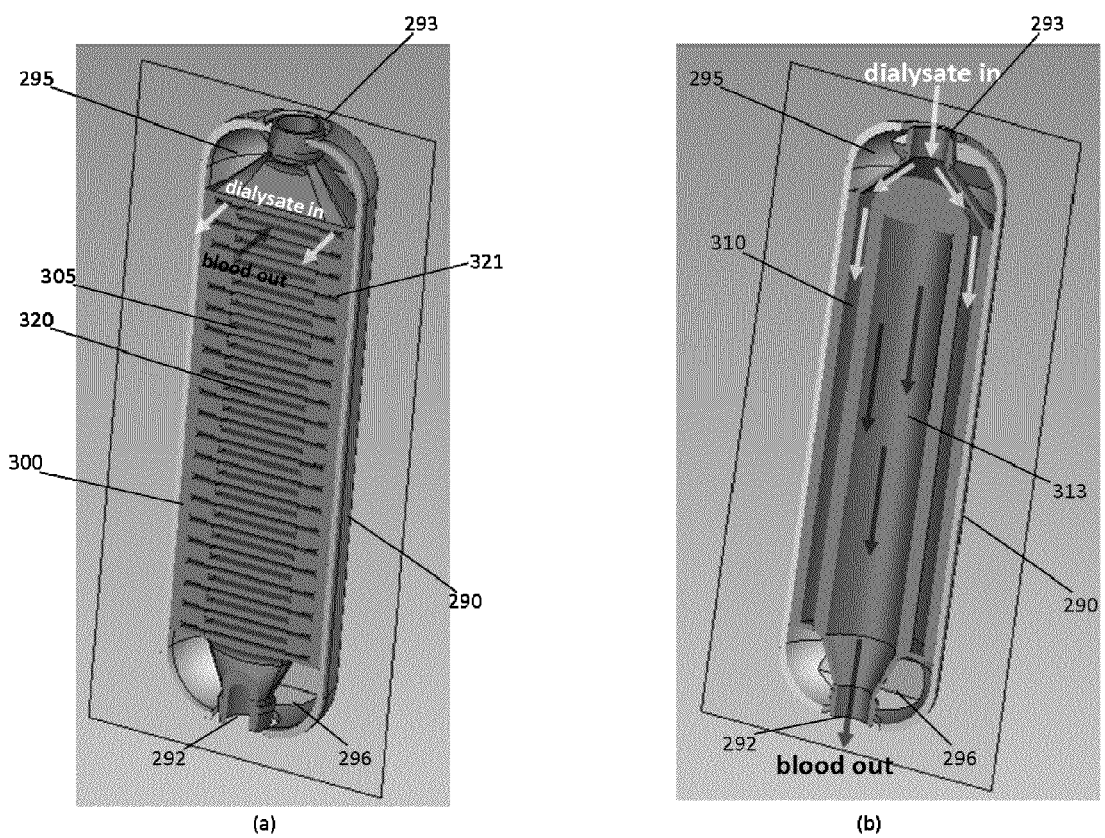
FIG. 40 shows sectional views of the implantable module embodiment.

FIGS. 39 and 40 show segmented blood and dialysate distribution and collection circuits within a certain embodiment of an implantable module. As shown in FIG. 39, blood enters the implantable module through blood inlet 291 and is distributed by the blood feed manifold 312 into a plurality of blood membrane channels 320. Dialysate exits the membrane stack 300 from a plurality of dialysate membrane channels 321, is combined into the dialysate return manifold 311, and exits the implantable module via dialysate outlet 294. As shown in FIGS. 40(a) and (b), dialysate enters the implantable module through dialysate inlet 293 and is distributed by dialysate feed manifold 310 into a plurality of dialysate membrane channels 321. Blood exits the membrane stack 300 from a plurality of blood membrane channels 320, is combined into the blood return manifold 313, and exits the implantable module via blood outlet 292. In this embodiment, the blood and dialysate manifolds are not tapered. Hence, the cross-sectional geometries of the manifolds do not transition along the length of the membrane stack except when transitioning to any one of the blood feed-in, blood feed-out; dialysate feed-in and dialysate feed-out.

Figure 41:
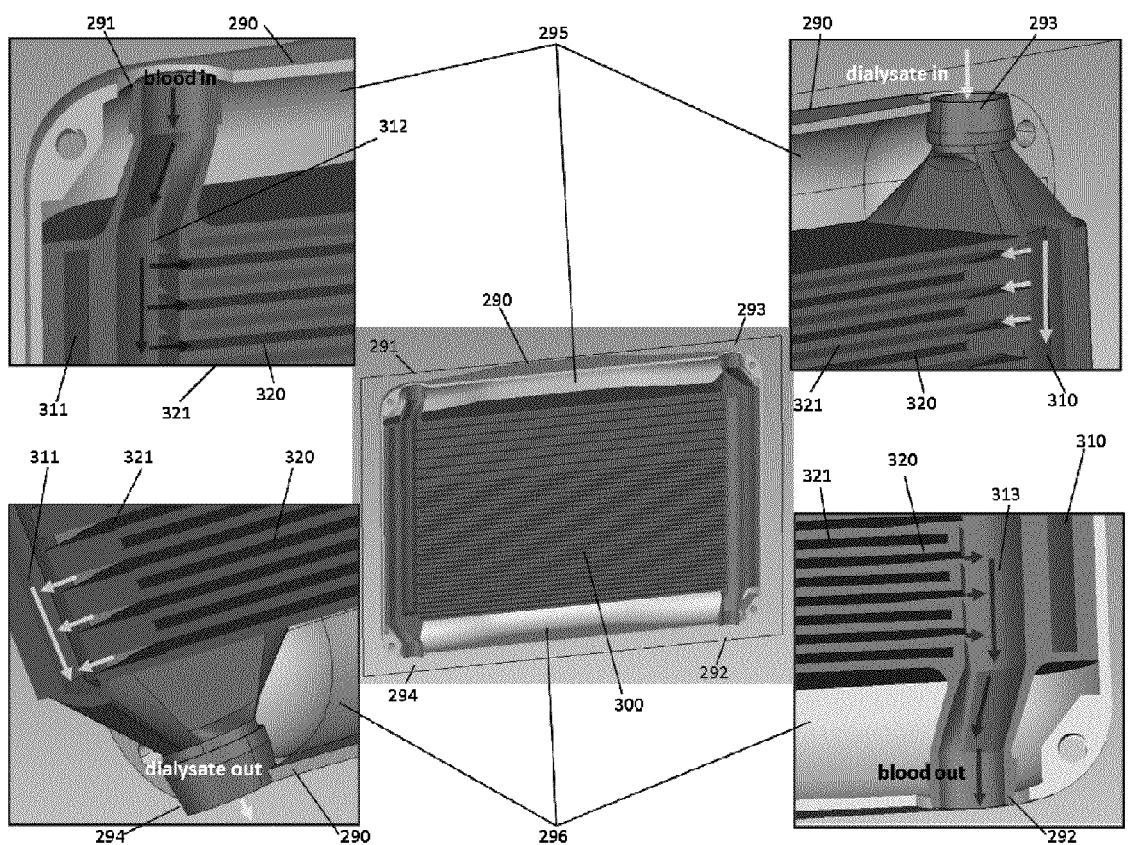
FIG. 41 shows a sectional perspective view of a back half of the implantable module embodiment. Details of regions of the implantable module embodiment are shown in magnifications.

FIG. 41 shows complete blood and dialysate distribution and collection circuits and the separation of distribution and collection manifolds within one embodiment of the implantable module. Blood enters blood inlet 291, is distributed by the blood feed manifold 312 into a plurality of blood membrane channels 320 within the membrane stack 300, is collected in the blood return manifold 313, and exits the implantable module through blood outlet 292. Dialysate enters dialysate inlet 293, is distributed by the dialysate feed manifold 310 into a plurality of dialysate membrane channels 321 within the membrane stack 300, is collected in the dialysate return manifold 311, and exits the implantable module through dialysate outlet 294.

Figure 42:
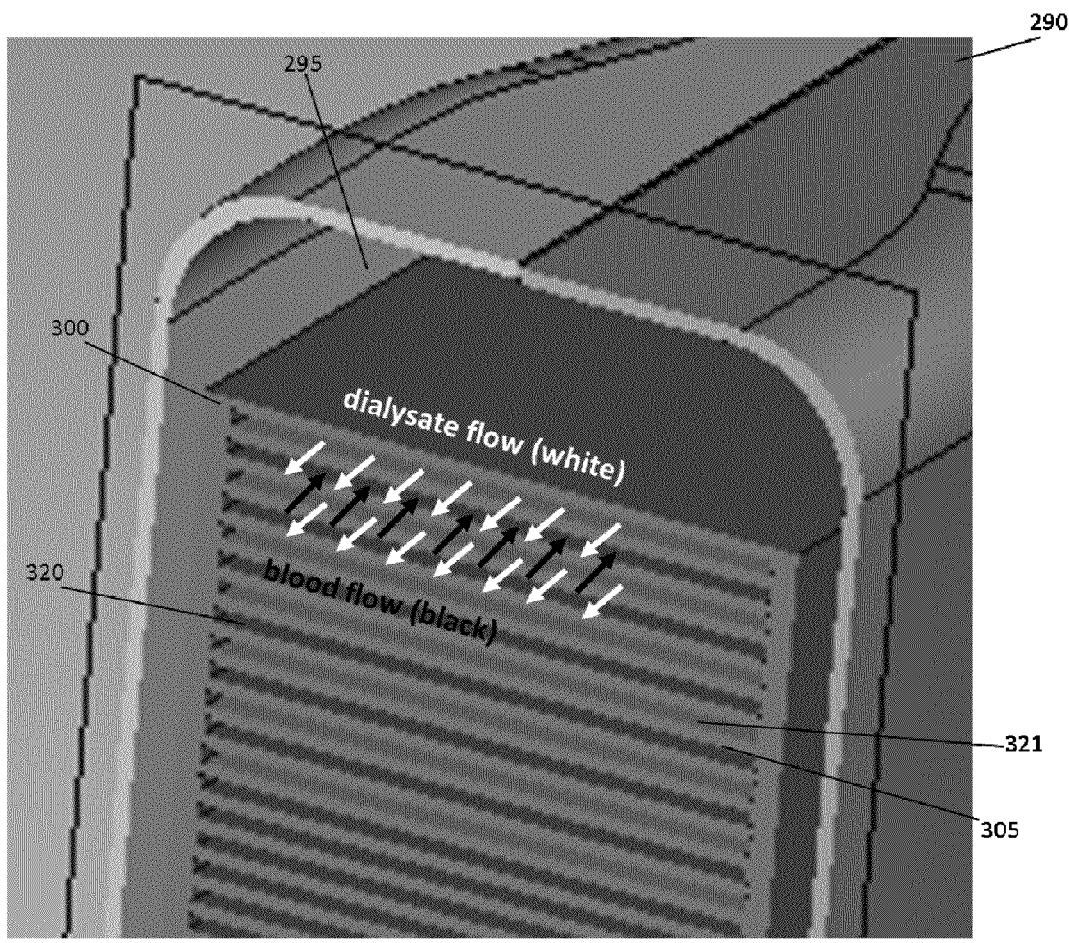
FIG. 42 is a sectional perspective view showing blood and dialysate membrane channels of the implantable module embodiment.

FIG. 42 illustrates the counter-current flow configuration of the membrane stack 300 within one embodiment of the implantable module. Blood flows in one direction in a plurality of blood membrane channels 320 while dialysate flows in an opposite direction in a plurality of dialysate membrane channels 321. The counter-current flow configuration promotes mass transfer between blood and dialysate across a plurality of membranes 305 within membrane stack 300.

Figure 43:
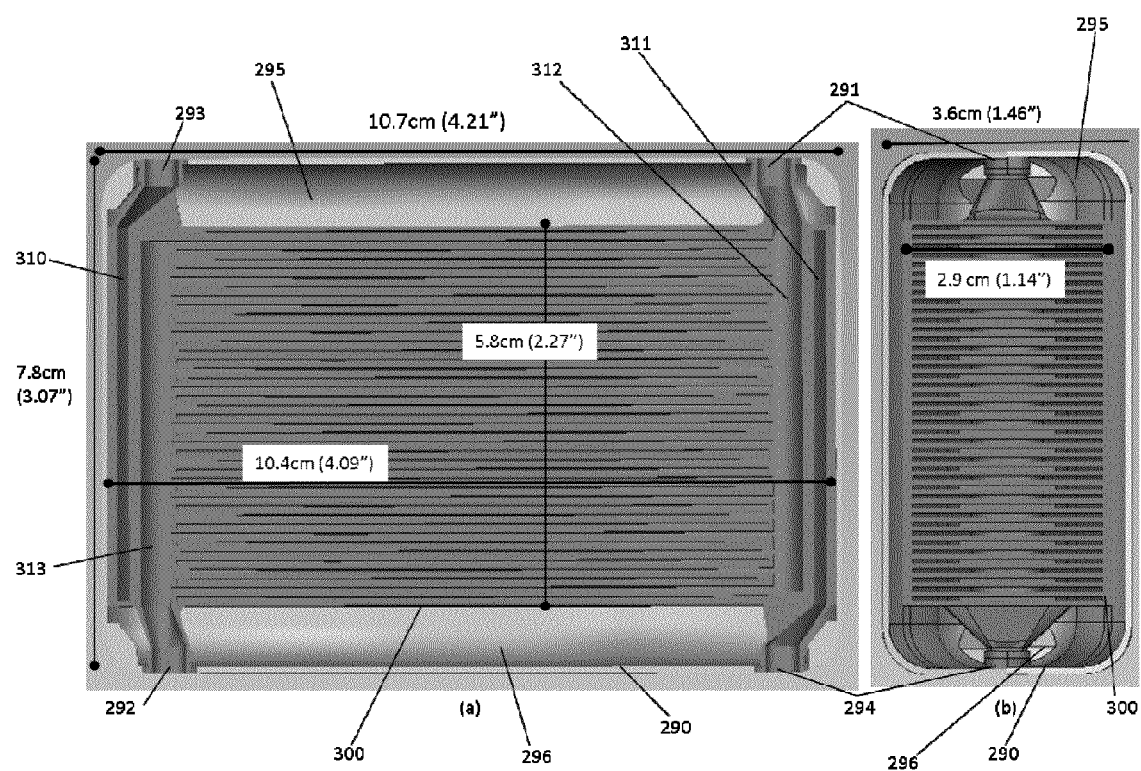
FIG. 43 shows dimensions of the implantable module embodiment.

Non-limiting dimensions of the implantable module are shown in FIG. 43 depicting one possible embodiment of the invention. FIG. 43(a) shows a front half of the implantable module and FIG. 43(b) shows a sectional view of a left side of the implantable module.

Figure 44:
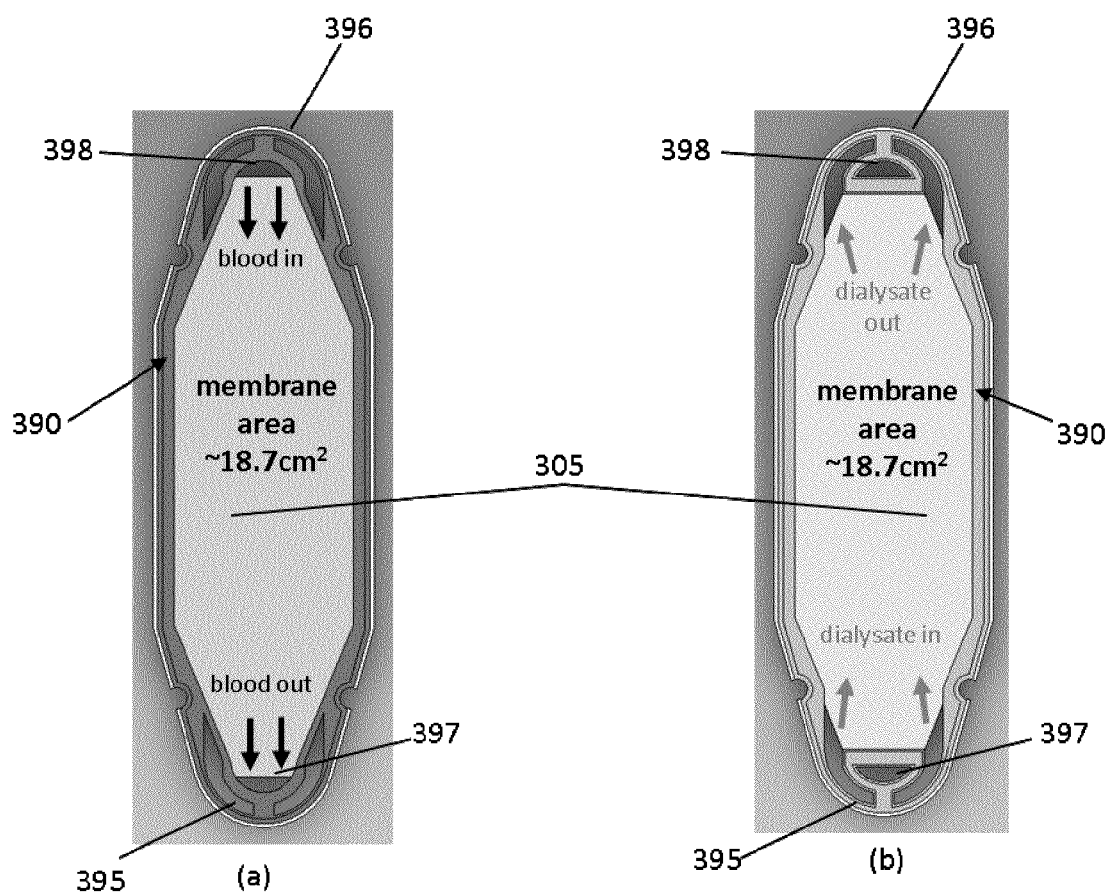
FIG. 44 shows a membrane filter element of the implantable module embodiment.

Referring to FIG. 44, a single membrane filter element 390 within another embodiment of the implantable module is depicted. FIG. 44(a) shows a first side of the single membrane filter element 390 on which interface of blood and the membrane occurs. Blood from blood feed manifold section 398 is delivered across membrane 305 and returned to blood return, manifold section 397. FIG. 44(b) shows a second side of the single membrane filter element 390 on which interface of dialysate and the membrane occurs. Dialysate from dialysate feed manifold section 395 is delivered across membrane 305 and returned to dialysate return manifold section 396.

Figure 45:
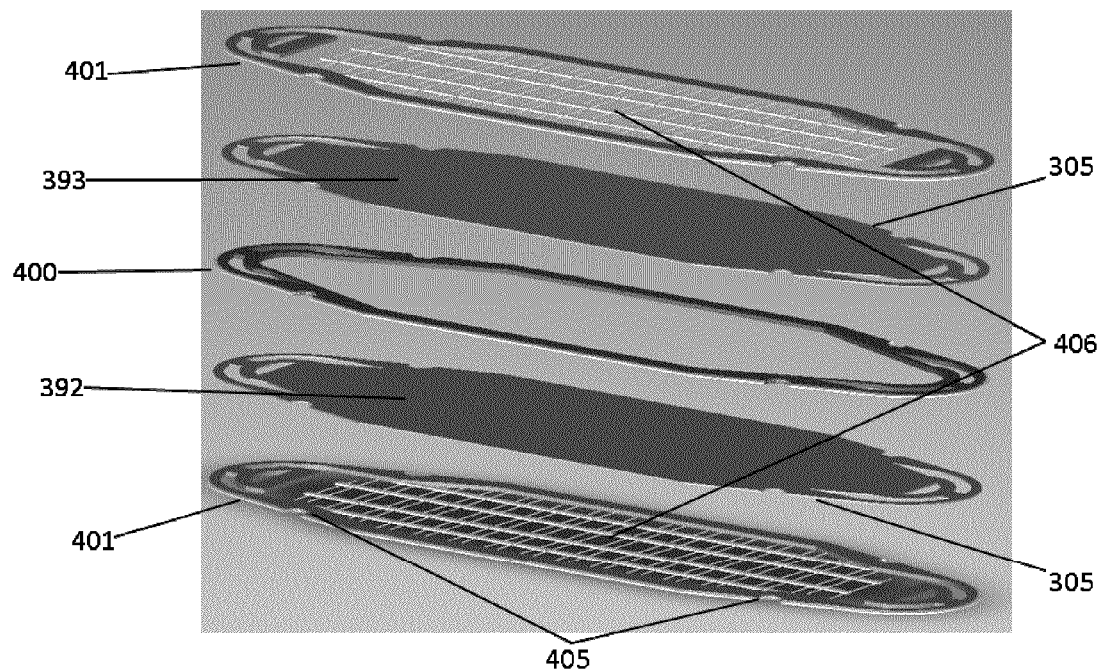
FIG. 45 is an exploded view of the layers of the membrane filter element.

One embodiment of the single membrane filter element 390 is shown separated into layers in FIG. 45. A blood layer 400 represents blood in a blood membrane channel on a blood interface side 392 of a membrane 305. A dialysate layer 401 represents dialysate in a dialysate membrane channel on a dialysate interface side 393 of a membrane 305. In certain embodiments, a membrane support matrix 406 supports the dialysate layer 401 and promotes turbulence of dialysate flowing therein. Alignment notches 405 promote alignment of the separated layers of membrane filter elements during, manufacturing.

Figure 46:
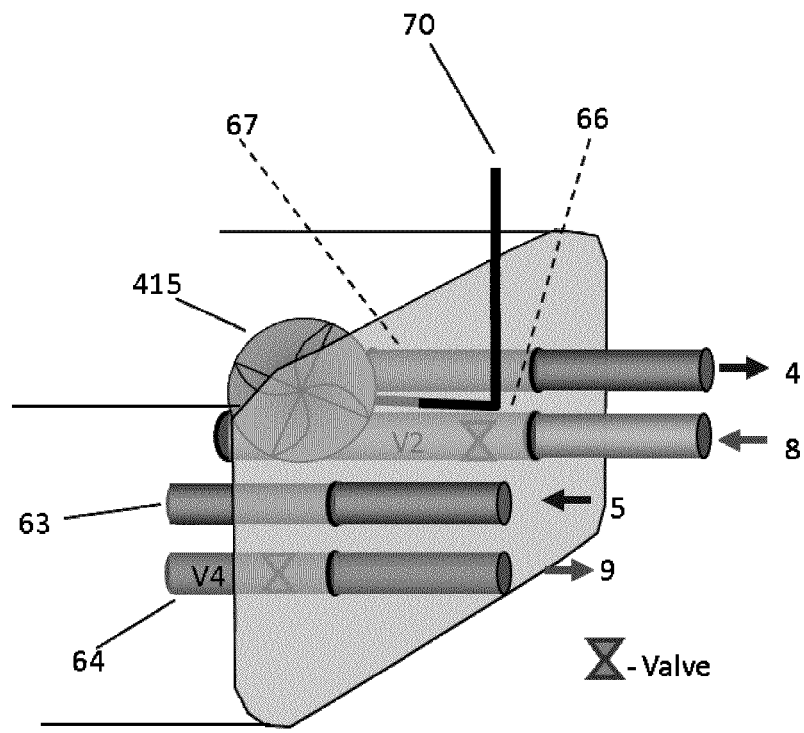
FIG. 46 is a transparent perspective view of the implantable module having a blood pump and two internal valves.

Referring to FIG. 46, a simplified view of a pump and valve arrangement of one possible embodiment of the implantable module is shown. Valve V2 is located on the blood feed manifold 66 within the implantable module 25. Valve V4 is located on the blood return manifold 64 within the implantable module 25. A blood pump 415 is located on the blood feed manifold 66. The blood pump 415 is driven and controlled by pump electrical cable 70. The blood pump 415 may also be powered by a rechargeable battery within the implantable module 25. Alternatively, the blood pump 415 may be driven by an externally supplied magnetic field, or hydraulic power.

Figure 47:
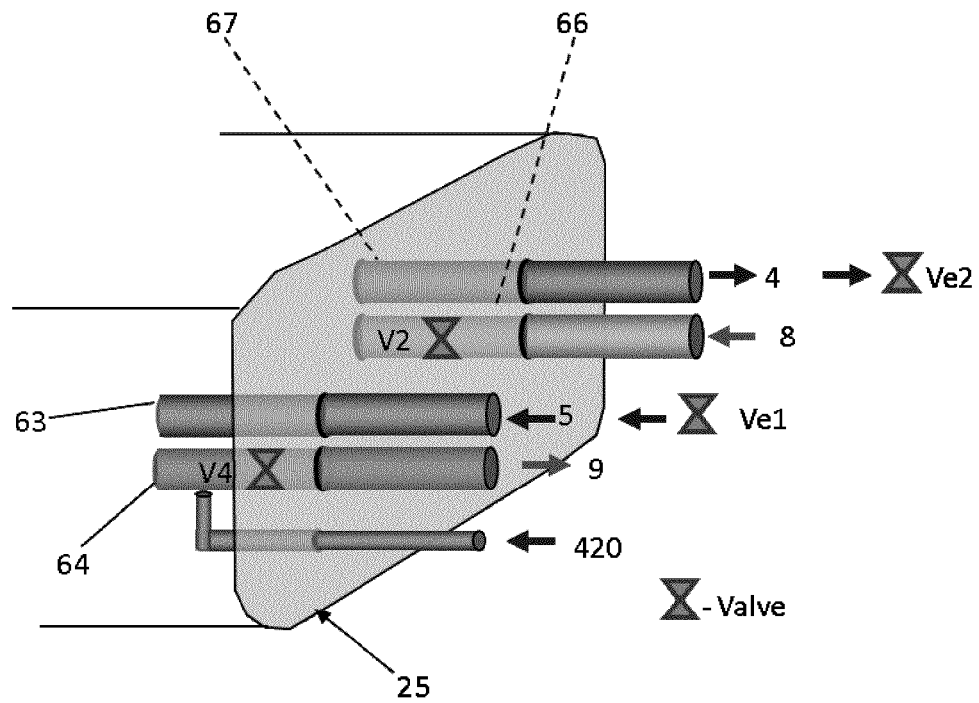
FIG. 47 is a transparent perspective view of the implantable module having two internal valves, two external valves, and a blood infusion line.

Referring to FIG. 47, a simplified view of a valve arrangement of one possible embodiment of the implantable module is shown with a blood infusion line 420. Valve V2 is located on the blood feed manifold 66 within the implantable module 25. Valve V4 is located on the blood return manifold 64 within the implantable module 25. External valve Ve1 is located outside of the implantable module 25 and can be disposed on the dialysate feed-in 5. External valve Ve2 is located outside of the implantable module 25 and can be disposed on the dialysate feed-out 4.

Figure 48:
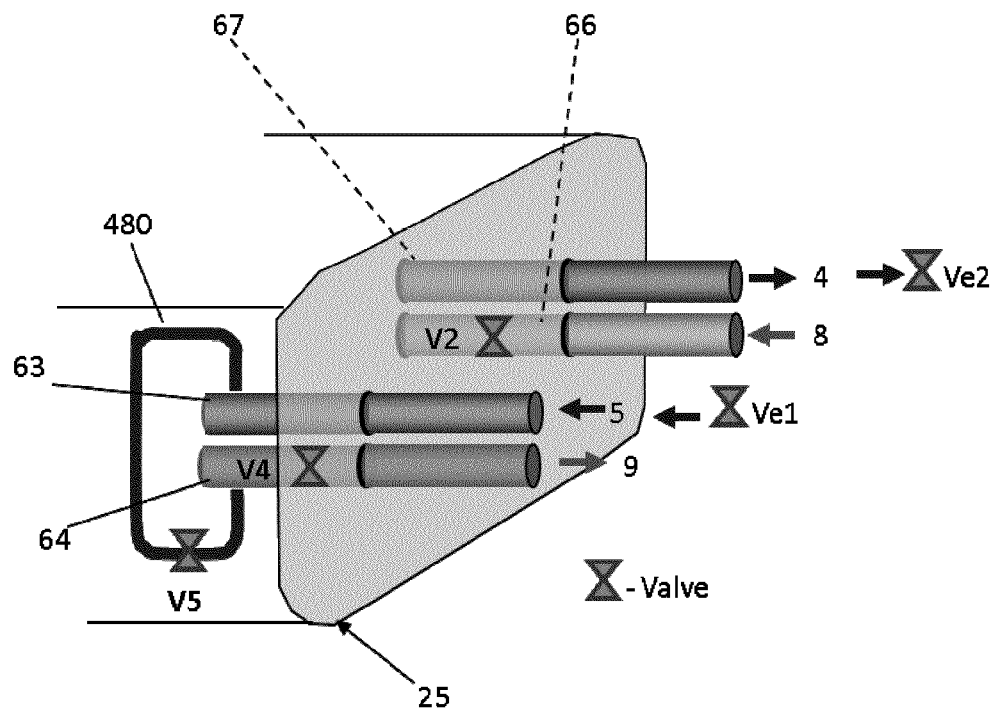
FIG. 48 is a transparent perspective view of the implantable module having three internal valves, two external valves, and a shunt.

Referring to FIG. 48, a simplified view of another valve arrangement of one possible embodiment of the implantable module is shown. Valve V2 is located on the blood feed manifold 66 within the implantable module 25. Valve V4 is located on the blood return manifold 64 within the implantable module 25. External valve Ve1 is located outside of the implantable module 25 controlling dialysate feed-in 5. External valve Ve2 is located outside of the implantable module 25 and can control dialysate feed-out 4. Shunt A 480 connects the dialysate feed manifold 63 and the blood return manifold 64. Valve V5 is located on shunt A 480.

Figure 49:
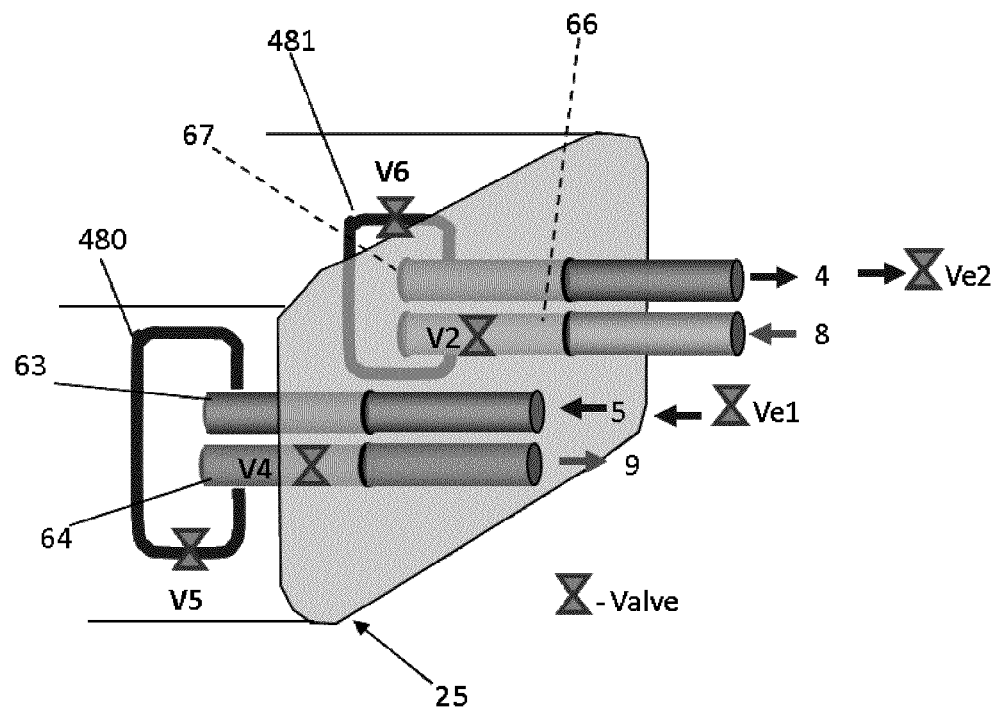
FIG. 49 is a transparent perspective view of the implantable module having four internal valves, two external valves, and two shunts.

Referring to FIG. 49, a simplified view of yet another valve arrangement of one possible embodiment of the implantable module is shown. Valve V2 is located on the blood feed manifold 66 within the implantable module 25. Valve V4 is located on the blood return manifold 64 within the implantable module 25. External valve Ve1 is located outside of the implantable module 25. External valve Ve2 is located outside of the implantable module 25. Shunt A 480 connects the dialysate feed manifold 63 and the blood return manifold 64. Shunt B 481 connects the blood feed manifold 66 and the dialysate return manifold 67. Valve V5 is located on shunt A 480. Valve V6 is located on shunt B 481.

Figure 50:
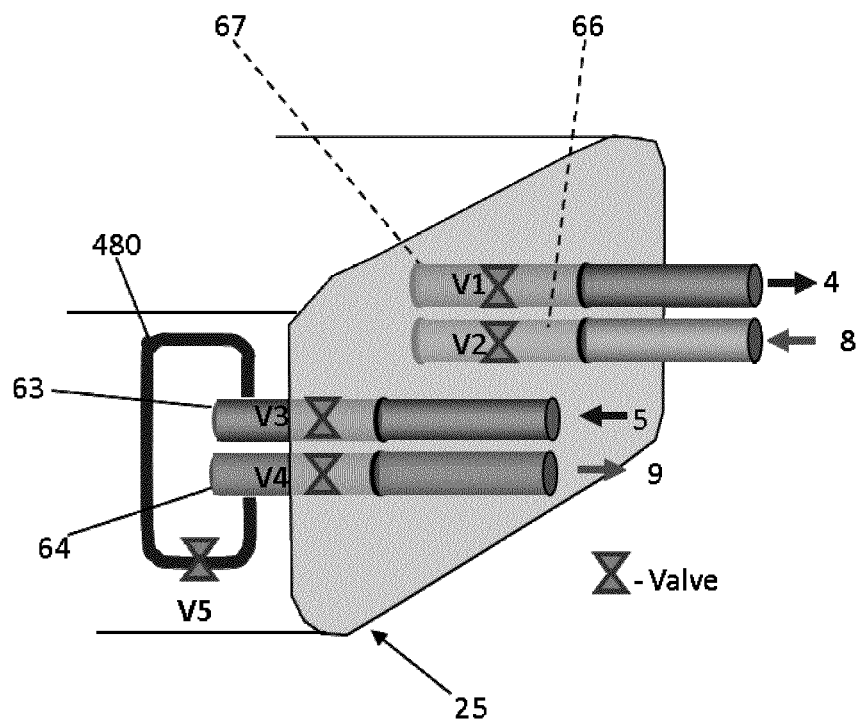
FIG. 50 is a transparent perspective view of the implantable module having five internal valves and a shunt.

Referring to FIG. 50, a simplified view of yet another valve arrangement of yet another possible embodiment of the implantable module is shown. Valve V2 is located on the blood feed manifold 66 within the implantable module 25. Valve V4 is located on the blood return manifold 64 within the implantable module 25. Valve V1 is located on the dialysate return manifold 67 within the implantable module 25. Valve V2 is located on the dialysate feed manifold 63 within the implantable module 25. Shunt A 480 connects dialysate feed manifold 63 and blood return manifold 64. Valve V5 is located on shunt A 480.

Figure 51:
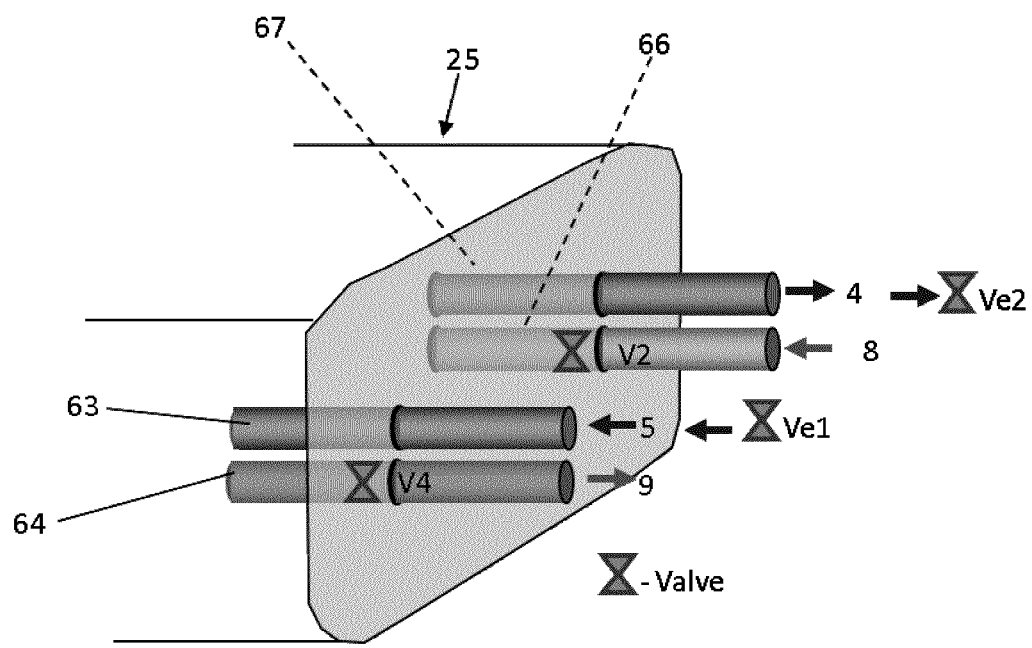
FIG. 51 is a transparent perspective view of the implantable module having two internal valves, and two external valves.

Referring to FIG. 51, a simplified view of a valve arrangement of one possible embodiment of the implantable module is shown. Valve V2 is located on the blood feed manifold 66 within the implantable module 25. Valve V4 is located on the blood return manifold 64 within the implantable module 25. External valve Ve1 is located outside of the implantable module 25. External valve Ve2 is located outside of the implantable module 25.

In certain embodiments, the functions of the hemodialysis system are controlled by a control system including a programmable control unit on the extracorporeal module. An electrical or wireless data link between the extracorporeal module and the implantable module forms a closed-loop feedback system. Systems and methods for establishing communication between an external device and an implanted medical device have been developed, such as those described in U.S. Pat. No. 7,023,359, Goetz et al., the subject matter of which is incorporated herein by reference.

The control unit may trigger a system safety shut-off in the event of blood or dialysate leakage in other embodiments. In the event of a safety shut-off, valves are closed to isolate the implantable module from the patient's vasculature. The control unit closes valves depending on the type of leakage. For example, referring to FIG. 49, if blood is leaking, valves V2 and V4 are closed by the control system. Similarly, if dialysate is leaking, valves Ve1, V2, Ve2, and V4 are closed by the control system.

In other embodiments, the cleansing function of the device is conducted via control of the system valves by the control unit. In general, cleansing of the hemodiafiltration system is accomplished by feeding a cleaning agent through the dialysate flow path of the system. The cleaning agent can also be directed through the blood flow path of the system via shunts, such as those shown in FIGS. 48-50, which connect the dialysate flow path and the blood flow path of the system. Preset programs direct the control unit on the extracorporeal module to operate the valves in the implantable module via an electrical or wireless connection between the extracorporeal module and implantable module.

System cleansing can be accomplished in two stages. The first stage is the flushing stage, and the second stage is the cleansing stage. During the flushing stage, the blood flow path is filled with a solution of dialysate and an anticoagulant, such as heparin. The dialysate-anticoagulant solution loosens weakly-bound protein and blood clot deposits accumulated within the blood flow path and on the filter media. After the flushing stage, the cleansing stage begins wherein the extracorporeal module pumps a cleaning agent through the blood flow path in place of the dialysate-anticoagulant solution of the flushing stage. Examples of cleaning agents include enzymes such as plasmin, matrix metalloproteinase ("MMP"), trypsin, and lipase, or any other enzyme having protein cleaving properties. Other cleaning agents include, detergents such as sodium dodecyl sulfate ("SDS"), polyethylene oxide ("PEO"), and polyethylene oxide-polypropylene oxide copolymer ("PEO-PPO"). Still other cleaning agents include acids, bases, and peroxides. In other embodiments, the anti-coagulant solution is advantageously not required due to controlled flushing of the device.

For the valve configuration shown in FIG. 47, the valves are operated according to Table 6.

TABLE 6

| Mode | V2 | V4 | Ve1 | Ve2 |
| --- | --- | --- | --- | --- |
| Hemodialysis | on | on | on | on |
| Ultrafiltration | on | on | off | on |
| Blood path flushing (NA) | | | | |
| Blood path soaking | on | off | off | off |
| Dialysate path flushing | off | off | on | on |
| Idle | off | off | off | off |
| Blood leaking shut-off | off | off | on | on |
| Contamination shut-off | off | off | off | off |

For the valve configuration shown in FIG. 48, the valves are operated according to Table 7.

TABLE 7

| Mode | V2 | V4 | V5 | Ve1 | Ve2 |
| --- | --- | --- | --- | --- | --- |
| Hemodialysis on | on | on | off | on | on |
| Ultrafiltration on | on | on | off | off | on |
| Blood path flushing (NA) | | | | | |
| Blood path soaking | on | off | on | on | off |
| Dialysate path flushing | off | off | off | on | on |

TABLE 7-continued

| Mode | V2 | V4 | V5 | Ve1 | Ve2 |
|---|---|---|---|---|---|
| Idle | off | off | off | off | off |
| Blood leaking shut-off | off | off | off | on | on |
| Contamination shut-off | off | off | off | off | off |

For the valve configuration shown in FIG. 49, the valves are operated according to Table 8.

TABLE 8

| Mode | V2 | V4 | V5 | V6 | Ve1 | Ve2 |
|---|---|---|---|---|---|---|
| Hemodialysis | on | on | off | off | on | on |
| Ultrafiltration | on | on | off | off | off | on |
| Blood path flushing | off | off | on | on | on | on |
| Blood path soaking | off | off | on | on | on | on |
| Dialysate path flushing | off | off | off | off | on | on |
| Idle | off | off | off | off | off | off |
| Blood leaking shut-off | off | off | on | on | on | on |
| Contamination shut-off | off | off | off | off | off | off |

For the valve configuration shown in FIG. 50, the valves are operated according to Table 9.

TABLE 9

| Mode | V1 | V2 | V3 | V4 | V5 |
|---|---|---|---|---|---|
| Hemodialysis | on | on | on | on | off |
| Ultrafiltration | on | on | off | on | off |
| Blood path flushing (NA) | | | | | |
| Blood path soaking | off | on | on | off | on |
| Dialysate path flushing | on | off | on | off | off |
| Idle | off | off | off | off | off |
| Blood leaking shut-off | on | off | on | off | off |
| Contamination shut-off | off | off | off | off | off |

The control unit on the extracorporeal module operates system valves based on a preset program. The control unit communicates with system valves via connection through electrical wires. Alternatively, the control unit can communicate with valves using a wireless connection.

In the six valve arrangement shown in FIG. 49, the control unit executes system cleansing by operating the valves as follows. During the flushing stage, valves V2, Ve1, and shunt valve V5 are open. Valves V4, Ve2, and shunt valve V6 are closed. The blood flow path is filled with the dialysate-anticoagulant solution pumped from a reservoir on the extracorporeal module via the dialysate flow path and shunt A 480. Residual blood remaining in the blood flow path is pushed out of the implantable module 25 by the dialysate-anticoagulant solution through V2, back to the arterial graft at the patient's artery. In the next step of the flushing procedure, valve V2 is closed and valve V4 is opened. The extracorporeal module continues to pump the dialysate-anticoagulant solution into the blood flow path, and any residual blood remaining in the implantable module 25 is pushed out through V4, back to the venous graft at the patient's vein. Once all residual blood is flushed out of the implantable module 25 back to the arterial and venous grafts, valve V4 is closed. Valve Ve2 and shunt valve V6 are then opened. The extracorporeal module circulates the dialysate-anticoagulant solution via pump through the blood flow path segment residing within the implantable module 25, and the entire dialysate flow path.

During the cleansing stage, the valve states remain unchanged from the end of the flushing stage to allow for circulation of the cleaning agent through the blood flow path segment residing within the implantable module 25, and the entire dialysate flow path. Once circulation of the cleaning agent is complete, the extracorporeal module circulates a blood-compatible dialysate through the blood and dialysate flow paths in place of the cleaning agent in order to remove residual cleaning agent from the flow paths and filter media. Once the system resumes hemodialysis, the flushing dialysate remaining in the blood flow path is pushed out through shunt A 480.

The valve configurations described may be suitable for other device functions and metrics as well.

In certain embodiments, the control unit can also assess device performance, and regulate dosing in certain embodiments. The control unit can assess device patency and membrane fouling based on blood pressure. Device performance can be assessed based on blood composition and blood pressure and blood flow. Device performance can also be assessed based on solute permeability rates during a treatment cycle. The control unit can determine dialysis and filtration progress by calculating blood osmolality based on blood or colloid osmotic pressure. Blood osmolality can also be used to alter dosing during treatments. The control unit can also alter dialysate composition and flow rate, and regulate trans-membrane pressure within the implantable module to control filtration rate.

It will be apparent to one skilled in the art that various combinations and/or modifications and variations can be made in implantable dialyzer and medical system depending upon the specific needs for operation. Moreover, features illustrated or described as being part of one embodiment may be used on another embodiment to yield a still further embodiment.

We claim:

1. An implantable dialyzer, comprising:
    a filter pack for hemodialysis and/or ultrafiltration having two or more membranes forming a membrane stack that has alternating dialysate and blood membrane channels interposed between each membrane;
    a first manifold assembly connected to a first side of the filter pack containing both a blood and a dialysate manifold, each manifold having a specified cross-sectional geometry, wherein the blood manifold is in fluid communication with the blood membrane channels and the dialysate manifold is in fluid communication with the dialysate membrane channels;
    a second manifold assembly connected to a second side of the filter pack containing both a blood and a dialysate manifold, each manifold having a specified cross-sectional geometry, wherein the blood manifold is in fluid communication with the blood membrane channels and the dialysate manifold is in fluid communication with the dialysate membrane channels;
    a blood feed-in and a blood feed-out in fluid communication with the blood membrane channels via the blood manifolds;
    a dialysate feed-in and a dialysate feed-out in fluid communication with the dialysate membrane channels via the dialysate manifolds; and
    a housing encasing the filter pack.

2. The implantable dialyzer of claim 1, wherein any one of the blood and dialysate manifolds has a cross-sectional geometry selected from a substantially C-shape, U-shape, D-shape, circle, rectangle, triangle or semicircle.

3. The implantable dialyzer of claim 2, wherein the cross sectional geometry of a blood or dialysate manifold can transition to another cross-sectional geometry that is a substantially C-shape, U-shape, D-shape, circle, rectangle, triangle or semicircle.

4. The implantable dialyzer of claim 2, wherein a flow path of a blood or dialysate manifold is constant from a top-most part to a bottom-most part of the first or second manifold assembly or is constant from the bottom-most part to the top-most part of the first or second manifold assembly.

5. The implantable dialyzer of claim 2, wherein a flow path of a blood or dialysate manifold linearly tapers from a top-most part to a bottom-most part of the first or second manifold assembly or linearly tapers from the bottom-most part to the top-most part of the first or second manifold assembly.

6. The implantable dialyzer of claim 2, wherein a flow path of a blood or dialysate manifold non-linearly tapers from a top-most part to a bottom-most part of the first or second manifold assembly or non-linearly tapers from the bottom-most part to the top-most part of the first or second manifold assembly.

7. The implantable dialyzer of claim 2, wherein a flow path of a blood or dialysate manifold varies from a top-most part to a bottom-most part of the first or second manifold assembly or varies from the bottom-most part to the top-most part of the first or second manifold assembly.

8. The implantable dialyzer of claim 2, wherein the cross sectional geometry or area of a blood or dialysate manifold is constant from a top-most part to a bottom-most part.

9. The implantable dialyzer of claim 1, wherein the cross sectional geometry or area of a blood manifold tapers from wide to narrow in the direction of flow into the membrane stack and the dialysate manifold tapers from narrow to wide in the direction of flow out of the implantable module in the first manifold assembly.

10. The implantable dialyzer of claim 1, wherein the cross sectional geometry or area of a dialysate manifold tapers from wide to narrow in the direction of flow into the membrane stack and the blood manifold tapers from narrow to wide in the direction of flow out of the implantable module in the second manifold assembly.

11. The implantable dialyzer of claim 1, wherein the area of the cross-section of the blood manifold decreases in the direction of flow into the membrane stack and the area of the cross-section of the dialysate manifold increases in the direction of flow out of the implantable module in the first manifold assembly.

12. The implantable dialyzer of claim 1, wherein the area of the cross-section of the dialysate manifold decreases in the direction of flow into the membrane stack and the area of the cross-section of the blood manifold increases in the direction of flow out of the implantable module in the second manifold assembly.

13. The implantable dialyzer of claim 1, wherein the area of the cross-section of the blood and dialysate manifolds is constant.

14. The implantable dialyzer of claim 1, wherein the membranes have a hydraulic permeability equal to or greater than about 0.5 mL/min/m$^2$/mmHg, a diffusive permeability equal to or greater than about 0.00015 cm/s, and an albumin sieve coefficient equal to or less than about 0.01.

15. The implantable dialyzer of claim 1, further comprising:
   a shunt A connecting the dialysate manifold in the second manifold assembly defined as a dialysate feed manifold with the blood manifold in the second manifold assembly defined as a blood return manifold;
   a shunt B connecting the blood manifold in the first manifold assembly defined as a blood feed manifold with the dialysate manifold in the first manifold assembly defined as a dialysate return manifold;
   a valve V2 disposed on the blood feed manifold;
   a valve V4 disposed on the blood return manifold;
   a valve V1 disposed on the dialysate return manifold;
   a valve V3 disposed on the dialysate feed manifold;
   an external valve Ve1 disposed on the dialysate feed-in;
   an external valve Ve2 disposed on the dialysate feed-out;
   a valve V5 disposed on the shunt A; and
   a valve V6 disposed on the shunt B.

16. The implantable dialyzer of claim 1, further comprising suturing holes disposed on the housing.

17. The implantable dialyzer of claim 1, further comprising a pump.

18. The implantable dialyzer of claim 1, wherein the housing is formed in a clamshell.

19. The implantable dialyzer of claim 1, wherein the housing is constructed of a biocompatible material.

20. The implantable dialyzer of claim 1, wherein spaces are formed in the housing at a top side or a bottom side.

21. The implantable dialyzer of claim 1, wherein the housing is contoured for ergonomic fit to a patient's anatomy.

22. The implantable dialyzer of claim 1, wherein the housing is contoured for ergonomic fit to a patient's anatomy, and a perimeter shape of the membranes is shaped to fit the housing.

23. The implantable dialyzer of claim 22, wherein the perimeter shape of an individual membrane is different from at least another membrane to fit the housing.

24. The implantable dialyzer of claim 22, wherein an individual membrane is stacked at relative offsets from another individual membrane to fit the housing.

25. The implantable dialyzer of claim 1, wherein the blood feed-in and blood feed-out are counter-flowing relative to the dialysate feed-in and dialysate feed-out.

26. The implantable dialyzer of claim 1, wherein the blood feed-in and blood feed-out are co-flowing relative to the dialysate feed-in and dialysate feed-out.

27. The implantable dialyzer of claim 1, wherein the blood feed-in is tapered inwardly and the blood feed-out is tapered outwardly.

28. The implantable dialyzer of claim 1, wherein the dialysate feed-in is tapered inwardly, and the dialysate feed-out is tapered outwardly.

29. The implantable dialyzer of claim 1, wherein the dialysate and blood membrane channels are configured for counter-flow.

30. The implantable dialyzer of claim 1, wherein the dialysate and blood membrane channels are configured for co-flow.

31. The implantable dialyzer of claim 1, wherein the membrane stack elements have offset cavities to allow room for separate feed flow paths.

32. The implantable dialyzer of claim 1, wherein the membranes are curve shaped.

33. The implantable dialyzer of claim 1, wherein the stacked membrane layers are angled with respect to the housing.

34. The implantable dialyzer of claim 1, further comprising a membrane support matrix disposed on the membranes supporting the dialysate layer and promoting turbulence.

35. The implantable dialyzer of claim 1, wherein the first and second manifold assembly is connected to the first side of the filter pack by welding, gluing, bonding, or clamping.

36. An implantable dialyzer, comprising:
   a bundled fiber filter comprising a plurality of hollow fibers for hemodialysis and/or ultrafiltration contained in a dialysate compartment surrounding the hollow fibers;
   a blood flow distributor that can distribute blood to the hollow fibers using blood from a blood inlet;

a blood flow collector that can collect dialyzed blood out from the hollow fibers and exit the dialyzer via a blood outlet;

a dialysate inlet that can direct dialysate into the dialysate compartment and a dialysate outlet that can direct dialysate out of the dialysate compartment; and a housing encasing the dialysate compartment.

\* \* \* \* \*